United States Patent
Li et al.

(10) Patent No.: US 10,660,917 B2
(45) Date of Patent: *May 26, 2020

(54) ENGINEERING AND DELIVERY OF THERAPEUTIC COMPOSITIONS OF FRESHLY ISOLATED CELLS

(71) Applicant: Maxcyte, Inc., Gaithersburg, MD (US)

(72) Inventors: Linhong Li, North Potomac, MD (US); Madhusudan V. Peshwa, Boyds, MD (US)

(73) Assignee: Maxcyte, Inc., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/602,536

(22) Filed: May 23, 2017

(65) Prior Publication Data

US 2017/0258837 A1 Sep. 14, 2017

Related U.S. Application Data

(63) Continuation of application No. 14/834,932, filed on Aug. 25, 2015, now Pat. No. 9,669,058, which is a continuation of application No. 13/902,444, filed on May 24, 2013, now Pat. No. 9,132,153, which is a continuation of application No. 12/421,352, filed on Apr. 9, 2009, now Pat. No. 8,450,112.

(60) Provisional application No. 61/043,653, filed on Apr. 9, 2008.

(51) Int. Cl.
| | |
|---|---|
| A61K 35/17 | (2015.01) |
| A61K 39/00 | (2006.01) |
| C12N 5/078 | (2010.01) |
| C12N 5/0783 | (2010.01) |
| A61K 39/395 | (2006.01) |
| C12N 13/00 | (2006.01) |
| C12N 15/85 | (2006.01) |
| A61K 35/12 | (2015.01) |

(52) U.S. Cl.
CPC .......... *A61K 35/17* (2013.01); *A61K 39/0011* (2013.01); *A61K 39/39558* (2013.01); *C12N 5/0634* (2013.01); *C12N 5/0646* (2013.01); *C12N 13/00* (2013.01); *C12N 15/85* (2013.01); *A61K 2035/124* (2013.01); *A61K 2039/5156* (2013.01); *A61K 2039/5158* (2013.01); *C12N 2501/599* (2013.01); *C12N 2510/00* (2013.01)

(58) Field of Classification Search
CPC .............. A61K 35/17; A61K 39/39558; A61K 39/0011; A61K 2035/124; A61K 2039/5156; A61K 2039/5158; C12N 13/00; C12N 15/85; C12N 5/0634; C12N 5/0646; C12N 2501/599; C12N 2510/00
USPC ............... 424/93.21; 435/461, 372
See application file for complete search history.

(56) References Cited

U.S. PATENT DOCUMENTS

| | | | |
|---|---|---|---|
| 5,612,207 A | 3/1997 | Nicolau et al. | |
| 5,720,921 A | 2/1998 | Meserol | |
| 6,074,605 A | 6/2000 | Meserol et al. | |
| 6,090,617 A | 7/2000 | Meserol | |
| 6,485,961 B1 | 11/2002 | Meserol | |
| 6,617,154 B1 | 9/2003 | Meserol | |
| 6,773,669 B1 | 8/2004 | Holaday et al. | |
| 7,029,916 B2 | 4/2006 | Dzekunov et al. | |
| 7,141,425 B2 | 11/2006 | Dzekunov et al. | |
| 8,450,112 B2 * | 5/2013 | Li ...................... | A61K 39/0011 424/93.21 |
| 9,132,153 B2 * | 9/2015 | Li ...................... | A61K 39/0011 |
| 9,669,058 B2 * | 6/2017 | Li ...................... | A61K 39/0011 |
| 2003/0026790 A1 | 2/2003 | Hwu et al. | |
| 2004/0038886 A1 | 2/2004 | Finney et al. | |
| 2004/0115784 A1 | 6/2004 | Dzekunov | |
| 2004/0214333 A1 | 10/2004 | Liu | |

FOREIGN PATENT DOCUMENTS

| | | | |
|---|---|---|---|
| WO | WO 1996/024671 | | 8/1996 |
| WO | WO 2002/077029 | | 10/2002 |
| WO | WO 2003/018751 | | 3/2003 |
| WO | WO 2004/031353 | | 4/2004 |
| WO | WO 2006/063301 | | 6/2006 |
| WO | WO 2007/065957 | | 6/2007 |
| WO | WO2008/097926 | * | 8/2008 |
| WO | WO 2008/097926 | | 8/2008 |
| WO | WO2008/121420 | * | 9/2008 |

OTHER PUBLICATIONS

Chowdhury et al. (1999) Nat. Biotech., vol. 17, 568-572.*
Zhao et al. (2006) Mol. Ther., vol. 13, 151-159.*
"Guidance for FDA Reviews and Sponsors. Content and Review of Chemistry, Manufacturing, and Control (CMC) Information for Human Somatic Cell Therapy Investigational New Drug Applications (INDs)," U.S. Department of Health and Human Services, Food and Drug Administration, Center for Biologics Evaluation and Research, Apr. 2008.
Abbott, "Recent advances in chronic lymphocytic leukemia," *Cancer Invest.*, 24:302-309, 2006.

(Continued)

*Primary Examiner* — Anne Marie S Wehbe
(74) *Attorney, Agent, or Firm* — Michele M. Wales; Inhouse Patent Counsel, LLC

(57) ABSTRACT

The present invention relates to the transient modification of cells. In particular embodiments, the cells are immune systems, such as PBMC, PBL, T (CD3+ and/or CD8+) and Natural Killer (NK) cells. The modified cells provide a population of cells that express a genetically engineered chimeric receptor which can be administered to a patient therapeutically. The present invention further relates to methods that deliver mRNA coding for the chimeric receptor to unstimulated resting PBMC, PBL, T (CD3+ and/or CD8+) and NK cells and which delivers the mRNA efficiently to the transfected cells and promotes significant target cell killing.

30 Claims, 60 Drawing Sheets

(56) References Cited

OTHER PUBLICATIONS

Bahceci et al., "Immunotherapy of B cell malingnancies using transiently redirected cytotoxic T cells," Blood (ASH Meeting Abstracts), 110(11):Abstract No. 2750, 2007.
Baxevanis and Papamichail, "Targeting of tumor cells by lymphocytes engineered to express chimeric receptor genes," Cancer Immunol. Immunother., 53:893-903, 2004.
Boissel et al., "Transfection with mRNA for CD19 specific chimeric antigen receptor restores NK cell mediated killing of CLL cells," Leukemia Research, 33(9):1255-1259, 2009.
Boissel et al., "Transfection with mRNA for CD19 specific chimeric antigen receptor restores natural killer cell mediated killing of CLL cells," Database Biosis, Accession No. PREV200800218382, 2007.
Boissel et al., "Transfection with mRNA for CD19 Specific Chimeric Antigen Receptor Restores Natural Killer Cell Mediated Killing of CLL Cells," Blood, 2007, 110:3110 (Abstract provided).
Bryceson et al., "Synergy among receptors on resting NK cells for the activation of natural cytotoxicity and cytokine secretion," Blood, 2006, vol. 107, No. 1, p. 159-166.
Caligiuri et al., "Immunotherapeutic approaches for hematologic malignancies," Hematology Am. Soc. Hematol. Educ. Program, 337-353, 2004.
Carlsten et al., "DNAX Accessory Molecule-1 Mediated Recognition of Freshly Isolated Ovarian Carcinoma by Resting Natural Killer Cells," Cancer Res., 2007, vol. 67, No. 3, p. 1317-1325.
Chiorean and Miller, "The biology of natural killer cells and implications for therapy of human disease," J. Hematother. Stem Cell Res., 10:451-463, 2001.
Cooper et al., "Development and application of CD19-specific T cells for adoptive immunotherapy of B cell malignancies," Blood Cells, Molecules, and Disease, 33:83-99, 2004.
Extended European Search Report, issued in European Patent Application No. 09731422.3, dated Nov. 21, 2011.
Farag et al., "Natural killer cell receptors: new biology and insights into the graft-versus-leukemia effect," Blood, 100:1935-1947, 2002.
Finney et al., "Activation of resting human primary T cells with chimeric receptors: costimulation from CD28, inducible costimulator, CD134, and CD137 in series with signals from the TCR zeta chain," J. Immunol., 172:104-113, 2004.
Friedmann-Morvinski et al., "Adoptive immunotherapy of cancer using effector lymphocytes redirected with antibody specificity," Update on Cancer Therapeutics, 1(1):25-32, 2006.
Gilboa, "DC-based cancer vaccines," J. Clin. Invest., 117:1195-203, 2007.
Golzio et al., "In vitro and in vivo electric field-mediated permeabilization, gene transfer, and expression," Methods, 33:126-135, 2004.
Hong and Park, "Application of natural killer T cells in antitumor immunotherapy," Crit. Rev. Immunol., 27:511-25, 2007.
Hui and Li, Electrochemotherapy, electrogenetherapy, and transdermal drug delivery: Electrically mediated delivery of molecules to cells, Human Press, Totowa, New Jersey, 2000.
Imai et al., "Chimeric receptors with 4-1BB signaling capacity provoke potent cytotoxicity against acute lymphoblastic leukemia," Leukemia, 18:676-684, 2004.
Imai et al., "Genetic modification of primary natural killer cells overcomes inhibitory signals and induces specific killing of leukemic cells," Blood, 106(1):376-383, 2005.
International Search Report and Written Opinion, issued in Application No. PCT/US2009/040040, dated Dec. 2, 2009.
Jung et al., "Local Immunotherapy of Glioma Patients With a Combination of 2 Bispecific Antibody Fragments and Resting Autologous Lymphocytes: Evidence for in Situ T-cell Activation an Therapeutic Efficacy," Int. J. Cancer, 91:225-230, 2001.
Klingemann, "Natural killer cell-based immunotherapeutic strategies," Cytotherapy, 7:16-22, 2005.
Landi et al., "High transfection efficiency, gene expression, and viability of monocyte-derived human dendritic cells after nonviral gene transfer," J. Leukoc. Biol., 82:849-60, 2007.
Lanier, "Activating and inhibitory NK cell receptors," Adv. Exp. Med. Biol., 452:13-18, 1998.
Le Blanc and Ringdén, "Immunomodulation by mesenchymal stem cells and clinical experience," J. Intern. Med., 262:509-25, 2007.
Leung et al., "Determinants of antileukemia effects of allogeneic NK cells," J. Immunol.., 172:644-650, 2004.
Li et al., "A highly efficient clinically applicable transfection method to redirect the specificity of immune cells and enhance their anti-tumor capacity," Database Biosis, Accession No. PREV200900260574, 2008.
Li et al., "Apoptosis induced by DNA uptake limits transfection efficiency," Exp. Cell. Res., 253:541-550, 1999.
Li et al., "Expressioin of chimeric antigen receptors in natural killer cells with a regulatory-compliant non-viral method," Cancer Gene Therapy, 17(3):147-154, 2010.
Li et al., "High-efficiency electrotransfection of human primary hematopoietic stem cells," FASEB J., 15:586-588, 2001.
Li et al., "Highly efficient, large volume flow electroporation," Technol. Cancer Res. Treat., 1:341-350, 2002.
Li et al., "Rapid and efficient nonviral gene delivery of CD154 to primary chronic lymphocytic leukemia cells," Cancer Gene Ther., 13:215-224, 2006.
Maasho et al., "Efficient gene transfer into the human natural killer cell line, NKL, using the Amaxa nucleofection system," J. Immunol. Methods, 284:133-140, 2004.
Manabe et al., "Interleukin-4 induces programmed cell death (apoptosis) in cases of high-risk acute lymphoblastic leukemia," 83:1731-1737, 1994.
Martino and Poccia, "Gamma delta T cells and dendritic cells: close partners and biological adjuvants for new therapies," Curr. Mol. Med., 7:658-73, 2007.
McKenna et al., "Good manufacturing practices production of natural killer cells for immunotherapy: a six-year single-institution experience," Transfusion, 47:520-528, 2007.
Miller et al., "Successful adoptive transfer and in vivo expansion of human haploidentical NK cells in patients with cancer," Blood, 105:3051-3057, 2005.
Mimeault et al., "Stem cells: a revolution in therapeutics-recent advances in stem cell biology and their therapeutic applications in regenerative medicine and cancer therapies," Clin. Pharmacol. Ther., 82:252-64, 2007.
Office Communication issued in European Patent Application No. 09 731 422.3, dated Jul. 2, 2012.
Office Communication issued in Japanese Patent Application No. 2011-504171, dated Jan. 8, 2014.
Passweg and Tyndall, "Autologous stem cell transplantation in autoimmune diseases," Semin. Hematol., 44:278-85, 2007.
Passweg et al., "Purified donor NK-lymphocyte infusion to consolidate engraftment after haploidentical stem cell transplantation," Leukemia, 18:1835-1838, 2004.
Pinthus et al., "Adoptive Immunotherapy of Prostate Cancer Bone Lesions Using Redirected Effector Lymphocytes," The Journal of Clinical Investigation, 114:1774-1781, 2004.
Rabinovich et al., "Synthetic messenger RNA as a tool for gene therapy," Hum. Gene Ther., 17:1027-35, 2006.
Ruggeri et al., "Effectiveness of donor natural killer cell alloreactivity in mismatched hematopoietic transplants," Science, 295:2097-2100, 2002.
Ruggeri et al., "Natural killer cell alloreactivity in allogeneic hematopoietic transplantation," Curr. Opin. Oncol., 19:142-147, 2007.
Serrano et al., "Differentiation of naïve cord-blood T cells into CD19-specific cytolytic effectors for posttransplantation adoptive immunotherapy," Blood, 107:2643-2652, 2006.
Simmons et al., "Use of recombinant lentivirus pseudotyped with vesicular stomatitis virus glycoprotein G for efficient generation of human anti-cancer chimeric T cells by transduction of human peripheral blood lymphocytes in vitro," J. Virol., 3:8, 2006.
Srivastava et al., "Development of a Rapid, Closed, Large-Scale Cell Loading Process for the Manufacture of Telomerase mRNA-Transfected Dendritic Cell Cancer Vaccine GRNVAC1," J. Immunother., 2006, vol. 29, No. 6, p. 656 (Abstract provided).

(56) References Cited

OTHER PUBLICATIONS

Teufel et al., "Human peripheral blood monuclear cells transfected with messenger RNA stimulate antigen-specific cytotoxic T-lymphocytes in vitro," *CMLS Cellular and Molecular Life Sciences*, 62(15):1755-1762, 2005.
Trompeter et al., "Rapid and highly efficient gene transfer into natural killer cells by nucleofection," *J. Immunol. Methods*, 274:245-256, 2003.
Van De Parre et al.,"mRNA but not plasmid DNA is efficiently transfected in murine J774A.1 macrophages," *Biochem. Biophys. Res. Comm.*, 327:356-360, 2005.
Van Tendeloo et al., "Highly efficient gene delivery by mRNA electroporation in human hematopoietic cells: superiority to lipofection and passive pulsing of mRNA and to electroporation of plasmid cDNA for tumor antigen loading of dendritic cells," *Blood*, 98:49-56, 2001.
Ward et al., "Endothelial progenitor cell therapy for the treatment of coronary disease, acute MI, and pulmonary arterial hypertension: current perspectives," *Catheter. Cardiovasc. Interv.*, 70:983-98, 2007.
Xie et al., "Study of mechanisms of electric field-induced DNA transfection. I. DNA entry by surface binding and diffusion through membrane pores," *Biophys. J.*, 58:13-19, 1990.
Zhao et al., "High-efficiency transfection of primary human and mouse T lymphocytes using RNA electroporation," *Mol. Ther.*, 13:151-159, 2006.
Zimmermann, "Electrical breakdown, electropermeabilization and electrofusion," *Rev. Physiol. Biochem. Pharmacol.*, 105:176-256, 1986.
Non-Final Office Action dated Dec. 26, 2019 received in corresponding U.S. Appl. No. 15/726,740.

\* cited by examiner

CD3

ENGINEERING AND DELIVERY OF THERAPEUTIC COMPOSITIONS OF FRESHLY ISOLATED CELLS

This application is a continuation of U.S. patent application Ser. No. 14/834,932, filed Aug. 25, 2016, which is a continuation of U.S. patent application Ser. No. 13/902,444 filed May 24, 2013, now issued as U.S. Pat. No. 9,132,153 on Sep. 15, 2015, which is a continuation of U.S. patent application Ser. No. 12/421,352, filed on Apr. 9, 2009, now issued as U.S. Pat. No. 8,450,112 on May 28, 2013, which claims the benefit of United States Provisional Patent Application Serial No. 61/043,653, filed on Apr. 9, 2008. The entirety of each of the above-referenced disclosures is incorporated herein by reference.

BACKGROUND OF THE INVENTION

1. Field of the Invention

The present invention relates generally to the fields of cell biology, cancer biology, and immunology. More particularly, it concerns cells that have been engineered by loading them with chemical and biological agents and the resultant entities used as therapeutics in the treatment of multiple indications, including cancer.

2. Description of Related Art

Mononuclear cells, encompassing for example hematopoietic stem cells, mesenchymal stem cells, endothelial progenitor cells, adipose derived stem cells, and peripheral blood mononuclear cells (PBMC), have been used in multiple applications for treatment of immune diseases and in regenerative medicine applications (Passweg J and Tyndall A., Semin Hematol. 2007 October 44(4):278-85; Le Blanc K and Ringdén O. Intern Med. 2007 November 262(5):509-25; Ward et al. Catheter Cardiovasc Interv. 2007 Dec. 1 70(7):983-98; Mimeault et al., Clin Pharmacol Ther. 2007 September 82(3):252-64 Epub 2007 Aug. 1).

Peripheral blood mononuclear cells (PBMC) are comprised of cells of myeloid and lymphoid lineages. Myeloid cells, such as monocytes, macrophages, dendritic cells (DC), when loaded with antigens have been demonstrated to be effective antigen presenting cells for generation of tumor-antigen specific immune responses for treatment of cancer or for modulation of self-antigen specific T cells and regulatory T cells in control of autoimmunity (Gilboa E., J Clin Invest. 2007 May 117(5):1195-203). Lymphoid cells, such as T cells, NK cells, B cells, lymphoid DC, are effective mediators of immune responses and can be further harnessed to also present antigen and stimulate naïve and memory responses (Hong C and Park S H. Crit Rev Immunol. 2007 27(6):511-25; Martino A and Poccia F, Curr Mol Med. 2007 November 7(7):658-73).

Antigen Presenting Cells (APC) are important sentinels for detecting and presenting antigens to the immune effector cells. They have been extensively studied for becoming the effective therapeutic agents. Factors of antigen-loading, process and presentation in the context of state of maturity of APC to engage effector cells are major concerns in the design and development of APC-based immunotherapies and vaccines. Electroloading of tumor antigens, provided in the form of nucleotides (DNA, mRNA) or proteins/lysates or multimeric antigenic formulations, allows for effective uptake and processing of antigens in freshly isolated cells without requiring efficient maturation of APC antigen uptake mechanisms. Further other chemical and/or biological agents can be electro-loaded into APC to affect antigen-processing, processed antigen presentation, or immuno-regulatory environment in subject/patient such that the effective biological activity of electro-loaded APC is engineered to be superior to that of naïve freshly isolated APC. Such antigen-loading or antigen-loading combined with enhancement of biological activity for freshly isolated (naïve) APC is a unique attribute of the composition of PBMC thus loaded allowing for rapid formulation and delivery of product to subject/patient. Such biological activity otherwise would only be imparted following processes that require elaborate cell culture, expansion, differentiation, maturation of other manipulation processes that do not lend themselves to delivery of a therapeutic composition of APC immunotherapy and vaccine products in clinically relevant time-frame for administration to subject/patient in a hospital/physician's office setting.

NK and T cells are important mediators of viral and tumor immune responses. They have been extensively studied for becoming the efficient therapeutic agents. Factors of efficient and specific target cell killing, procedure simplicity, cell availability and low graft versus host disease (GvHD) are the major concerns. Chimeric receptor constructs have been described which, when expressed in cells of the immune system, can enhance the immunological specific response to tumor cells and thereby bring clinical benefit to cancer patients. Expanded NK and T cells expressing a chimeric receptor can overcome HLA-type-related inhibition of the expanded NK cell killing and T cell receptor (TCR)-required T cell killing of targeted tumor cells (Imai et al. 2004). However, considering the simplicity of using resting NK or T cells, if the resting NK or T cells, either autologous or allogeneic, could be engineered to have both efficient and specific target cell killing, it will be the desired for the tumor therapy. Furthermore, if resting peripheral blood lymphocytes (PBL) or even peripheral blood mononuclear cells (PBMC) could be engineered to have both efficient and specific target cell killing, it will be the most desired for the tumor therapy because of procedural simplicity and cell availability. Regular retroviral vectors could not infect resting NK or T cells. Lentiviral vectors have been used to transfect resting peripheral blood lymphocytes (Simmons et al. 2006). Unfortunately, use of viral vectors entails safety and practical problems for clinical application.

Electroporation is a well recognized method for loading nucleic acids into cells to achieve transfection of the loaded cells. The terminology of electroporation, electrotransfection and electroloading have been interchangablly used in the literature with emphasis on general meaning of this technology, the transgene expression and the transference of molecules into cytoplasm, respectively. Hereinafter this method of transfecting cells is referred to as electroloading that is the method using electroporation with no transfecting reagent or biologically based packaging of the nucleic acid being loaded, such as a viral vector or viral-like particle, relying only on a transient electric field being applied to the cell to facilitate loading of the cell. Within electroporation, nucleofection is a special one involving a transfection reagent helping the transferred DNA in the cytoplasm to the nucleus. Nucleofection has been reported to transfect resting T cells and NK cells using plasmid DNA treated with a proprietary nucleofection agent (Maasho et al., 2004). It was also demonstrated that resting T cell nucleofection of chimeric receptor could lead to specific target cell killing (Finney, et al, 2004). Many reports showed that nucleofection or electroloading with DNA resulted in cell toxicity to resting hematopoietic cells including lymphocytes, dendritic cells and NK cells (Trompeter et al. 2003; Li et al. 2006; Li et al. 2001; Li et al. 1999; Landi et al., 2007; Van De Parre et al. 2005; Maasho et al. 2004; Abbott et al. 2006). Nucleofected resting NK cells or electrotransfected resting hematopoietic cells showed good transient viability and efficient transgene expression within a few hours after transfection and low viability after approximated 28 and 52 hours post-nucleofection and much decreased expression of a transgene at these times (Trompeter et al. 2003). Accordingly, this method of transient DNA transfection would not provide for a clinically useful preparation of transiently modified resting NK and T cells. Moreover, the transfection efficiency of fresh resting NK cells was about half that of growing NK cell lines.

Loading of cells with mRNA brings several advantages, and potentially could overcome problems associated with DNA transfection, especially in respect to resting cells and cells that will be infused into a patient. First, mRNA, especially when loaded by electroloading results in minimal cell toxicity relative to loading with plasmid DNA, and this is especially true for electroloading of resting cells such as resting NK and peripheral blood mononuclear cells (PBMC) cells. Also, since mRNA need not enter the cell nucleus to be expressed resting cells readily express loaded mRNA. Further, since mRNA need not be transported to the nucleus, or transcribed or processed it can begin to be translated essentially immediately following entry into the cell's cytoplasm. This allows for rapid expression of the gene coded by the mRNA. Moreover, mRNA does not replicate or modify the heritable genetic material of cells and mRNA preparations typically contain a single protein coding sequence, which codes for the protein one wishes to have expressed in the loaded cell. Various studies on mRNA electroloading have been reported (Landi et al., 2007; Van De Pane et al. 2005; Rabinovich et al. 2006; Zhao et al., 2006).

For a number of medical reasons autologous immunotherapy with resting unstimulated NK, T, PBL, and PBMC and allogeneic immunotherapy for resting unstimulated NK cells can be advantageous for treatment of cancer. In this context a method that allows removal of cells from the patient, their treatment outside the body, and their subsequent infusion in to the patient in minimal time, with minimal intervening procedure, and with minimal addition of foreign materials, particularly materials that contain replicating genetic information, or are antigenic, is desired for safety, and reasons of cost and efficiency. A method that allows modification of these cells without need of extensive cell culture, more specifically without the need for the cells to undergo cell division outside the body, comprises loading only of a nucleic acid that codes for only the therapeutic protein and which is not capable of replicating in the cells or modifying the genome of the cell that has been removed from the patient, and which will be returned to the patient, and which additionally does not involve the use of any other biologically or immunologically active components is desired.

SUMMARY OF THE INVENTION

The ability to load freshly prepared unsitmulated resting PBMCs using a method that only employs nucleic acids (DNA, mRNA, microRNA or RNAi), proteins and small molecules without requiring additional synthetic transfection reagents or viral vectors provides for a transfusion-medicine approach to development of immunotherapy products whereby PBMCs are removed from a patient or allogenic donor, electroloaded, a process defined herein as electrotransfection, and soon thereafter reinfused into the patient to effect enhanced biological activity in PBMC cell populations leading to enhanced therapeutic effects for treatment of patients. This therapeutic approach simplifies the procedure of obtaining therapeutic compositions of cells that otherwise could only be obtained following extensive manipulation, including culture, activation, expansion and genetic modification of the expanded cells. As used herein, a peripheral blood mononuclear cell (PBMC) refers to a blood cell having a nucleus, such as a lymphocyte or monocyte. An "unstimulated" PBMC refers to a PBMC that has not been activated, such as by a cytokine or antigen.

Certain embodiments of the present invention provide methods whereby a nucleic acid, such as a DNA or a mRNA, coding for a genetically engineered receptor is loaded into NK cells, including resting primary NK cells, by means of electroloading to provide transiently transfected NK cells that express the chimeric receptor encoded by the nucleic acid. Also disclosed are methods for transfection of NK cells with nucleic acids, such as DNAs or mRNAs, encoding for more than one chimeric receptor or a combination of a chimeric receptor with other chemical and/or biological agents. In some embodiments, the present invention also provides for engineering NK cells by loading with a nucleic acid, such as a DNA or a mRNA, encoding for a chimeric receptor which can be used as an immunotherapeutic cell therapy for the treatment of cancer or disease of the immune system.

In one embodiment, the present invention provides a method for transiently modifying a resting primary peripheral blood mononuclear cell (PBMC) to expresses a chimeric receptor on its surface comprising: isolating resting primary PBMCs; and electroloading the PBMCs with a nucleic acid, such as a DNA or an mRNA, encoding a chimeric receptor, whereby the electroloaded PBMCs express the chimeric receptor on its surface. In certain aspects of the invention the PBMCs are monocytes. In some aspects of the invention, the PBMCs are peripheral blood lymphocytes (PBLs). In some embodiments, the lymphocytes are natural killer (NK) cells, CD3+ T cells, and/or CD8+ T cells. Resting PBMCs are PBMCs directly collected from peripheral blood or are thawed PBMCs that were frozen directly after collection from peripheral blood. Resting PBMCs may be cultured for a short time (e.g., less than 2 days) with or without specific stimulation of cytokines or ligands to stimulate cell activation for cell number expansion.

In one embodiment, the present invention provides a method for transiently modifying a natural killer (NK) cell to expresses a chimeric receptor on its surface comprising: isolating an NK cell; and electroloading the NK cell with a nucleic acid, such as a DNA or an mRNA, encoding a chimeric receptor, whereby the electroloaded NK cell expresses the chimeric receptor on its surface.

The NK cell may be a resting NK cell or a growing NK cell line. Resting NK cells are NK cells directly collected from peripheral blood or are thawed NK cells that were frozen directly after collection from peripheral blood. Resting NK cells may be cultured for a short time (e.g., less than 2 days) with or without specific stimulation of cytokines or ligands to stimulate cell activation for cell number expansion. Growing NK cells are cells that have undergone cell stimulation/activation with a cytokine and ligand to activate cells to expand in cell number.

An "isolated" NK cell or "isolating" an NK cell refers to separating NK cells from non-NK cells such as red blood cells, monocytes, T cells, and B cells. A variety of methods are known for the isolation of NK cells and kits are commercially available for this purpose. When NK cells are being isolated from whole blood, it may be desirable to first separate (by centrifugation, for example) the red blood cells from immune-system cells, and then to further separate the NK cells from other types of immune-system cells. One approach for separating NK cells from other cells is based on the expression of different surface markers on different cell types. For example, one can select for NK cells with antibodies that bind CD56 or CD16, which are expressed on the surface of NK cells, for positive selection. Thus, in one aspect of the invention, isolating NK cells comprises separation of CD56+ cells from CD56− cells. In another aspect of the invention, isolating NK cells comprises separation of CD16+ cells from CD16− cells. In a further aspect of the invention, isolating NK cells comprises separation of CD56+ and CD16+ cells from CD56− and CD16− cells. Antibodies used for isolating NK cells will generally be attached to a solid support and/or magnetic particles (e.g., magnetic beads) to facilitate the separation of the captured cells from those cells that were not bound by the antibody. Isolation of NK cells may also comprise depletion (i.e., negative selection) of non-NK cells from the sample by binding surface markers, such as CD14, CD3, and/or CD19, which are not expressed on the surface of NK cells. Thus, in one aspect of the invention, isolating NK cells comprises depleting CD14+, CD3+, and/or CD19+ cells from the sample.

An "isolated" T cell or "isolating" a T cell refers to separating T cells from non-T cells such as red blood cells, monocytes, NK cells, and B cells. A variety of methods are known for the isolation of T cells and kits are commercially available for this purpose. When T cells are being isolated from whole blood, it may be desirable to first separate (by centrifugation, for example) the red blood cells from immune-system cells, and then to further separate the T cells from other types of immune-system cells. One approach for separating T cells from other cells is based on the expression of different surface markers on different cell types. For example, one can select for T cells with antibodies that bind CD3, which is expressed on the surface of T cells, for positive selection. Isolation of T cells may also comprise depletion (i.e., negative selection) of non-T cells from the sample by binding surface markers, such as CD56 and CD16, which are not expressed on the surface of T cells. PBLs, may be isolated from other non-PBL PBMCs by culturing the PBMCs in a container (e.g., flask) and removing the cells that attach to the surface of the container after about 1-2 hours.

The purity of isolated cells may be determined by, for example, fluorescence-activated cell sorting (FACS). In one embodiment of the invention, isolating NK cells or T cells comprises isolating peripheral blood lymphocytes (PBLs) from other cells, such as red blood cells and monocytes. In certain aspects, the PBLs comprise at least 70%, 80%, 90%, 95%, 97%, 99%, or 99.5% of the cells in a composition. In another embodiment of the invention, isolating NK cells comprises isolating the NK cells from all other types of cells, including other PBLs. In certain aspects, the NK cells comprise at least 20%, 30%, 40%, 50%, 60%, 70%, 80%, 90%, 95%, 97%, 99%, or 99.5% of the cells in a composition. In another embodiment of the invention, isolating T cells comprises isolating the T cells from all other types of cells, including other PBLs. In certain aspects, the T cells comprise at least 90%, 95%, 97%, 99%, or 99.5% of the cells in a composition.

The terms "transient transfection" and "transiently modifying" refer to the introduction of a nucleic acid molecule into a cell using a transfection process that does not usually result in the introduced nucleic acid molecule being inserted into the nuclear genome, the introduced nucleic acid molecule is, therefore, lost as the cells undergo mitosis. In contrast, "stable transfection" refers to a transfection process in which cells that have integrated the introduced nucleic acid molecule into their genome are selected. In this way, the stably transfected nucleic acid remains in the genome of the cell and its daughter cell after mitosis. The term "transiently expressing" refers to the transient expression of a nucleic acid molecule in a transiently transfected cell.

In one embodiment, the present invention provides a method of treating a hyperproliferative disease in a subject comprising: obtaining isolated resting primary peripheral blood mononuclear cells (PBMCs); electroloading the PBMCs with a nucleic acid, such as a DNA or an mRNA, coding for a chimeric receptor, whereby the electro-loaded PBMCs express the chimeric receptor on its surface; and administering the transfected PBMCs to the subject to treat the hyperproliferative disease in the subject. In certain embodiments, the PBMCs are obtained from a donor other than the subject being treated. In other embodiments, the PBMCs are obtained from the subject with the hyperproliferative disease.

In one embodiment, the present invention provides a method of treating a hyperproliferative disease in a subject comprising: obtaining isolated NK cells from a subject with a hyperproliferative disease or from a donor; electroloading the NK cells with a nucleic acid, such as a DNA or an mRNA, coding for a chimeric receptor, whereby the electroloaded NK cells express the chimeric receptor on their surfaces; and administering the transfected NK cells to the subject to treat the hyperproliferative disease in the subject. In certain embodiments, the NK cells are freshly collected primary NK cells. In one aspect, the freshly collected primary NK cells are isolated and electro-loaded immediately after they are obtained from the subject.

In some embodiments, the freshly collected primary PBMCs are collected, isolated, and transfected within about 0.5 to 3 hours, 0.5 to 2 hours, or 0.5 to 1 hour. In some embodiments, the freshly collected primary PBMCs are frozen immediately after being collected from patient. The PBMCs may be frozen in peripheral blood or they may be isolated and then frozen or they may be isolated, transfected and then frozen. Thus, in certain aspects of the invention, fresh primary PBMCs may be thawed cells that were frozen immediately after collection from a patient/donor or immediately after isolation following collection. In some embodiments, the transfected cells are administered to the patient within about 1 to 48 hours, 1 to 24 hours, 1 to 15 hours, 1 to 10 hours, or 1 to 5 hours from the time the cells were originally obtained from the patient or donor. In some aspects, freshly collected cells are cells that have been collected from a subject but have not undergone cell division outside of the subject; thus, administering freshly collected cells to a subject would refer to administering cells that have not undergone cell division outside of a subject.

In certain embodiments, the subject is a human. In one embodiment, the hyperproliferative disease is cancer. It is contemplated that any type of cancer can be treated with the methods and compositions disclosed herein, including, for example, breast cancer, lung cancer, prostate cancer, ovarian cancer, brain cancer, liver cancer, cervical cancer, colon cancer, renal cancer, skin cancer, head & neck cancer, bone cancer, esophageal cancer, bladder cancer, uterine cancer, lymphatic cancer, stomach cancer, pancreatic cancer, testicular cancer, or leukemia. The leukemia may be, for example, acute lymphocytic leukemia (ALL), acute myelogenous leukemia (AML), chronic lymphocytic leukemia (CLL), chronic myelogenous leukemia (CML), or mantle cell lymphoma (MCL).

The transfected cells may be administered to the subject by methods well known to those of skill in the art. For example, the transfected cells may be administered by intravenous injection, intraarterial injection, intralymphatic injection, intramuscular injection, intratumoral injection, or subcutaneous injection. It is also contemplated that the transfected cells may be administered intraperitoneally. The transfected cells may be administered to the subject at or near a tumor in the subject, or to a site from which a tumor has been surgically removed from the subject. However, it is not necessary that the transfected cells be administered at the tumor site to achieve a therapeutic effect. Thus, in certain embodiments the transfected cells may be administered at a site distant from the tumor site. A medical practitioner will be able to determine a suitable administration route for a particular subject based, in part, on the type and location of the hyperproliferative disease. The transfected cells may be administered locally to a disease site, regionally to a disease site, or systemically. In one embodiment, the cells are administered by intravenous injection or intralymphatic injection. In another embodiment, the transfected cells are administered locally to a tumor site, such as by intratumoral injection. In some embodiments, the transfected cells are administered back in to the patient in less than 48 hours, less than 24 hours, or less than 12 hours from the time from when the peripheral blood is collected from the donor. In certain aspects of the invention, the transfected cells are administered back in to the patient within about 1 to 48 hours, 1 to 24 hours, 1 to 15 hours, 1 to 12 hours, 1 to 10 hours, or 1 to 5 hours from the time the NK cells were originally obtained from the donor. The donor and the subject being treated may be the same person or different people. Thus, in some embodiments the cells are autologous to the subject; and in other embodiments, the cells are allogenic to the subject.

The chimeric receptor will generally be selected based on the cell being targeted for killing. Thus, in one embodiment of the invention, the chimeric receptor is a chimeric receptor that binds a tumor antigen. CD19 is expressed on B-lineage cells. Accordingly, to kill leukemic B cells an anti-CD19 chimeric receptor could be expressed on the surface of a PBMC, such as a NK cell, which would enhance interaction between the modified NK cells and B cells. Thus, in one embodiment of the invention, the chimeric receptor is an anti-CD19 chimeric receptor. In one aspect, the anti-CD19 chimeric receptor is an anti-CD19BBz encoding a single chain antibody conjugated with the 4-1 BB intercellular domain and the CD3 domain. In certain embodiments, the chimeric receptor is an anti-CD20, anti-FBP, anti-TAG-72, anti-CEA, anti-carboxyanhydrase IX, nati-CD171, anti-IL-13 receptor, anti-G(D)2, anti-PSMA, anti-mesothelin, anti-Lewis-Y, or anti-CD30 chimeric receptor. CARs directed to these antigens may be used to treat the diseases associated with the cells that express these antigens. For example, these antigens have been associated with at least the following tumors: CD-19 (leukemia), FBP (ovarian), TAG-72 (colorectal), CEA (colorectal, breast, gastric), carboxyanhydrase IX (renal), CD171 (neuroblastoma), IL-13 receptor (glioblastoma), G(D)2 (neuroblastoma), PSMA (prostate), mesothelin (pancreatic), Lewis-Y (myeloma), or CD30 (cutaneous lymphoma). In certain aspects of the invention, the chimeric receptor does not contain an intracellular domain. In certain embodiments, the chimeric receptor does not contain a CD28 intracellular domain.

In another embodiment, the present invention provides a composition comprising: an electroloaded PBMC transiently expressing transgene encoded by a nucleic acid, such as a DNA or an mRNA, coding for a chimeric receptor, whereby the chimeric receptor is expressed on the surface of the electro-loaded PBMC; and a pharmaceutically acceptable carrier. In one aspect of the invention, the PBMC is a resting PBMC. In another aspect of the invention, the composition is frozen. The chimeric receptor may be, for example, an anti-CD19 chimeric receptor. In some embodiments, the composition does not contain a DNA, such as a DNA plasmid, encoding the chimeric receptor. In certain embodiments, the composition is free or substantially free of viral vectors and viral-like particles.

In one embodiment, the present invention provides a composition comprising: an electrotransfected NK cell transiently expressing transgene encoded by a mRNA coding for a chimeric receptor, whereby the chimeric receptor is expressed on the surface of the electrotransfected NK cell; and a pharmaceutically acceptable carrier. In one aspect of the invention, the NK cell is a resting NK cell. In another aspect of the invention, the composition is frozen. The chimeric receptor may be, for example, an anti-CD19 chimeric receptor. In some embodiments, the composition does not contain a DNA, such as a DNA plasmid, encoding the chimeric receptor. In certain embodiments, the composition is free or substantially free of non-NK cells. In certain aspects, at least 60%, 80%, 90%, 95%, 96%, 96%, 98%, 99%, 99.5%, or 99.9% of the cells in the composition are NK cells.

The present invention also provides for loading antigens into PBMCs, and in particular in to antigen presenting cells (APCs), or for loading said antigens along with other chemical or biological agents that enhance effectiveness of antigen processing, antigen presentation, cell trafficking and localization, and control of immunoregulatory environment in a subject/patient, to facilitate use of freshly isolated (naïve) and electro-loaded PBMCs as therapeutic compositions and methods for treatment of cancer and immune diseases.

Those of skill in the art are familiar with methods of electroporation. The electroporation may be, for example, flow electroporation or static electroporation. In one embodiment, the method of transfecting the cancer cells comprises use of an electroporation device as described in U.S. patent application Ser. No. 10/225,446, incorporated herein by reference. Methods and devices for electroporation are also described in, for example, published PCT Application Nos. WO 03/018751 and WO 2004/031353; U.S. patent application Ser. Nos. 10/781,440, 10/080,272, and 10/675,592; and U.S. Pat. Nos. 5,720,921, 6,074,605, 6,773,669, 6,090,617, 6,485,961, 6,617,154, 5,612,207, all of which are incorporated by reference.

It is contemplated that any method or composition described herein can be implemented with respect to any other method or composition described herein.

Any embodiment of any of the present methods, devices, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value.

Following long-standing patent law, the words "a" and "an," when used in conjunction with the word "comprising" in the claims or specification, denotes one or more, unless specifically noted.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A shows that FITC-dextran (500 k MW) could be efficiently loaded into expanded NK cells. FIG. 1B shows that FITC-siRNA (21-mer) could be efficiently loaded into expanded NK cells. FIG. 1C shows that DNA plasmid encoding eGFP driven by CMV promoter could be transfected into 6-day expanded NK cells. FIG. 1D shows that mRNA encoding eGFP could be efficiently transfected into expanded NK cells with no significant viability lose. FIG. 1E shows proliferation of eGFP-mRNA transfected cells.

FIG. 2A shows that 65% of viable cells could express anti-CD19 chimeric receptor. FIG. 2B shows that the anti-CD19 chimeric receptor expression was mRNA concentration dependent, and could express up to 4-5 days.

FIG. 3A shows NK cell phenotype after Miltenyi bead isolation. FIG. 3B shows that resting NK cells could be efficiently transfected with mRNA encoding eGFP or anti-CD19 chimeric receptor. FIG. 3C shows the expression duration of the anti-CD19 chimeric receptor in resting NK cells. FIG. 3D shows a summary of viability and expression level of resting NK cells from two donors.

FIG. 4A shows that CD3+ cells could be efficiently depleted with Dynal bead from 28% to 0.4%. FIG. 4B shows that either depletion or no depletion of CD3+ cells from expanded NK cells did not affect the NK cell killing of OP-1 cells.

FIG. 5A shows that proper transfection resulted in expression of the transgene. FIG. 5B shows typical FACS data that GFP-expressed NK cells did not kill CD19-PE+ OP-1 cells (3rd panels from left). Only anti-CD19 chimeric receptor-expressed NK cells killed OP-1 significantly (4th panels from left). FIG. 5C shows a summary of anti-CD19 chimeric receptor-specific OP-1 killing. Electroporation alone (calcein-AM method) and GFP-transfected NK cells (antibody staining) did not kill OP-1. Anti-CD19 chimeric receptor-expressed NK cells significantly killed OP-1.

FIG. 7A shows that NK cells expanded from two different donors led to similar and significant OP-1 cell killing. FIG. 7B shows that resting NK cells from two different donors led to similar and significant OP-1 cell killing.

FIG. 8A shows significantly higher cell killing of B-CLL cells by expanded NK cells with anti-CD19 chimeric receptor expression than that by naïve expanded NK cells. B-CLL cells were from two donors. FIG. 8B shows that B-CLL cells could be specifically killed by resting NK cells with anti-CD19 chimeric receptor expression. The killing was efficient for at least 2 days after transfection.

FIG. 9A shows typical FACS analysis data. FIG. 9B shows dependence of viability on time post transfection. FIG. 9C shows dependence of viable cell numbers on time post transfection. FIG. 9D shows dependence of expression on time post transfection.

FIG. 12A shows dependence of viability of transfected PBL on time post transfection. FIG. 12B shows dependence of viable cell recovery on time post transfection. FIG. 12C shows expansion of transfected PBL analyzed with CFSE. FIG. 12D shows expansion of CD3+ cells analyzed with CFSE.

FIG. 13A shows typical FACS analysis result of OP-1 cell line killing. FIG. 13B shows specific OP-1 killing by 2 donors of transfected PBL. FIG. 13C shows non-specific K562 cell killing by transfected PBL. FIG. 13D shows specific CLL cell killing.

DESCRIPTION OF ILLUSTRATIVE EMBODIMENTS

Figure 1A:
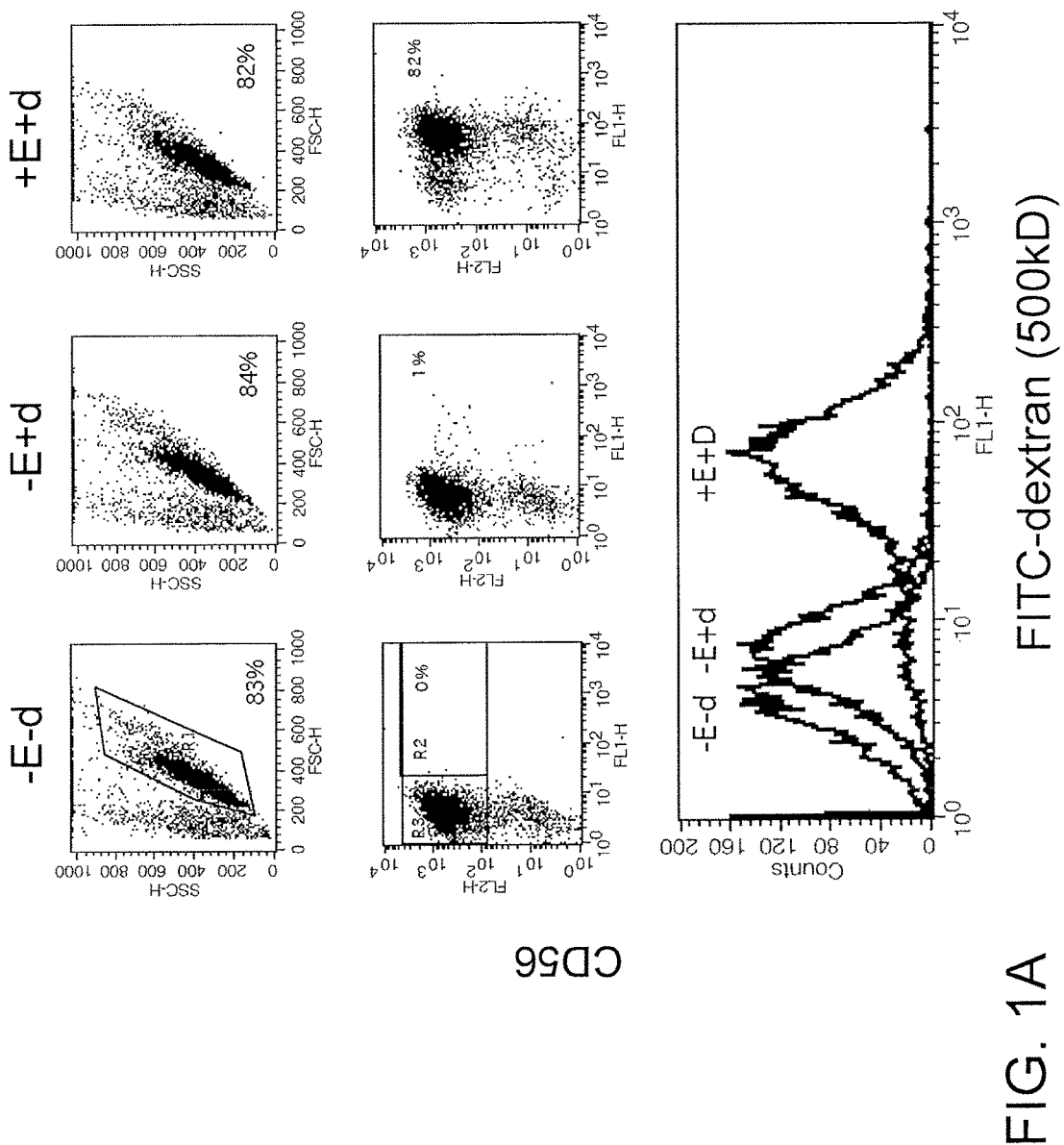
FIGS. 1A-1E. Macromolecule loading/transfection in expanded NK cells.
Figure 1B:
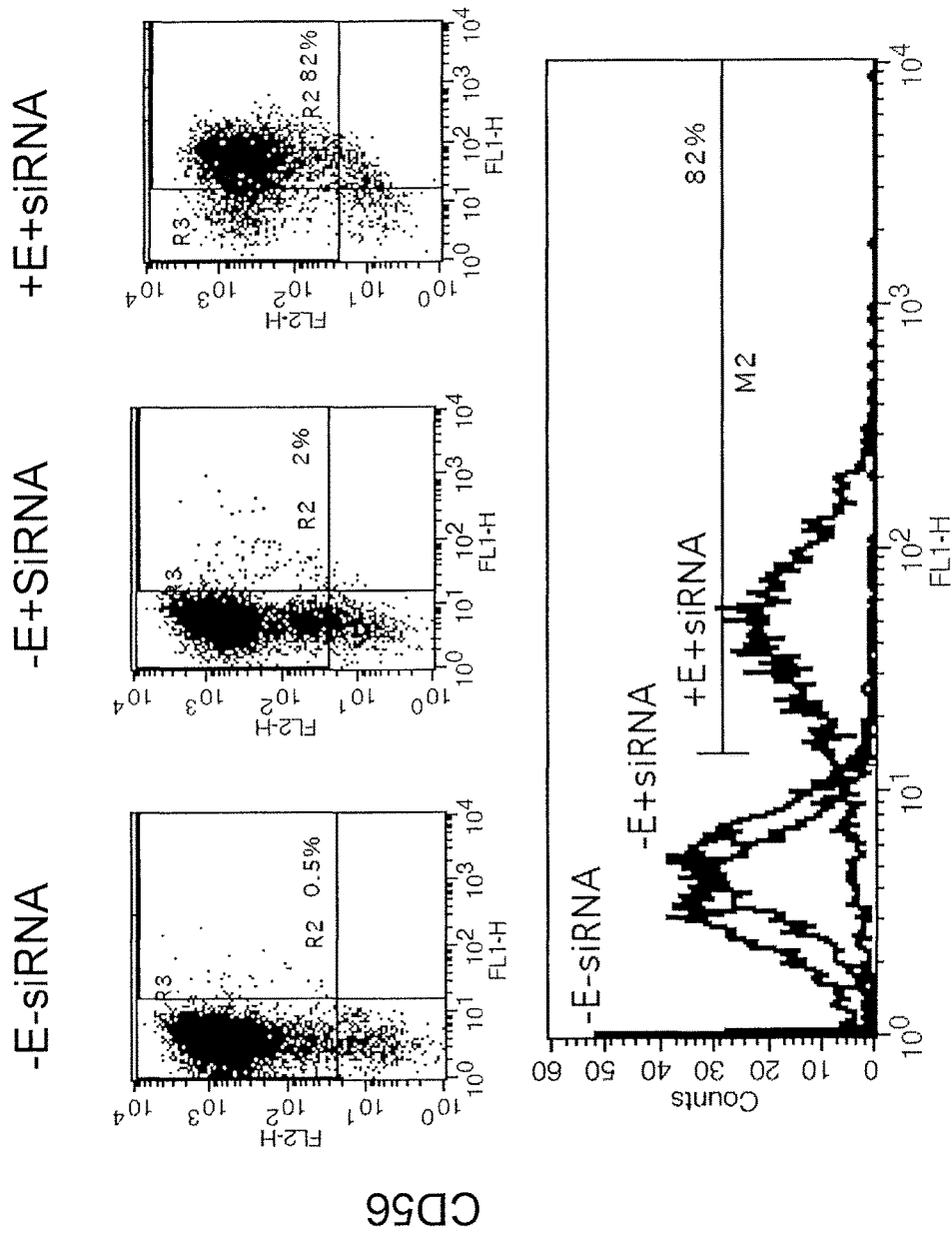

The present invention provides methods and compositions for the prevention and treatment of diseases, such as cancer and other hyperproliferative diseases. In certain embodiments, present invention provides methods for the preparation of transiently modified NK, T, PBL, and/or PBMC cells that provide previously unattained levels of cell viability following transfection, expression of a chimeric receptor that enhances specific anti-tumor activity by the modified cells, convenience and clinical applicability in autologous and allogeneic immunotherapeutic regimen, and improved precision in the transient modification, and safety in terms of risk of engineering of transfected cells. The methods are applicable to a wide range of chimeric receptor constructs and therapeutic proteins.

The ability to load freshly obtained resting unstimulated cells, from sources such as, for example peripheral blood, bone marrow, fat or other organ/tissue sources, using a method that employs transient energy delivery to facilitate transfer of chemical and/or biological agents, such as for example nucleotides (DNA, mRNA, microRNA or RNAi), proteins and small molecules, across a lipid bi-layer to affect the biological activity of desired cells within the freshly isolated cell population, wherein the affected biological activity is enhanced compared to the freshly isolated (non-loaded) cell compositions, and wherein the said composition of engineered cells can be safely delivered within a clinically relevant time-frame to a patient within a hospital and/or physician's office setting without requiring extensive needs for culture, expansion, differentiation or manipulation of cells, provides for unique therapeutic compositions of cells, in the context of a transfusion-medicine like approach to the development and delivery of novel therapeutic products, as effective treatment for multiple immune diseases.

Specifically, an approach to development of immunotherapy products whereby unstimulated mononuclear cells obtained from peripheral blood are obtained from a patient, loaded with relevant chemical or biological agents using transient delivery of energy, such as electrical, light, sound, heat, waves, and chemical and/or biological mediation, to affect the biological activity of freshly isolated mononuclear cells, and soon thereafter reinfused into the patient to effect enhanced biological activity in specific mononuclear cell populations contained with the freshly isolated cells leading to enhanced therapeutic effects for treatment of patients. This therapeutic approach may provide an alternative to the use of purified, isolated, or enriched cells, that need to be expanded/activated and transformed to impact their biological activity (potency) and thus may be preferred in multiple situations requiring medical interventions.

Mononuclear cells obtained from multiple sources (peripheral blood, bone marrow aspirates, lipo-aspirates, tissue-specific perfusates/isolates) can be effectively loaded with chemical and/or biological agents in a controlled manner using electrical energy, thereafter referred to as electroloading, to obtain desired level and duration of modulation of molecular pathways. Controlled intervention of molecular pathways provides means for affecting biological activity of cells when administered back to subject/patient, thus enhancing the ability to mitigate potency and efficacy that is otherwise not provided for in the administration of unmodified, freshly isolated cells.

A. NATURAL KILLER CELLS

In certain embodiments, the present invention employs genetically modified natural killer cells in the treatment of hyperproliferative diseases. Natural killer cells (NK cells) are a type of cytotoxic lymphocyte. NK cells are activated in response to interferons or macrophage-derived cytokines, and they play a major role in the rejection of tumors and cells infected by viruses. NK cells kill cancer cells and virally infected cells by releasing small cytoplasmic granules called perforin and granzyme that cause the target cell to die.

NK cells are characterized by their lack of the T cell receptor (CD3) and their expression of CD56 on their surface. Accordingly, these characteristics may be used to separate NK cells from other cell types. In contrast to cytotoxic T lymphocytes (CTL), NK cells do not require antigen activation and are not MHC restricted.

Cancer cells may evade killing by NK cells because self HLA molecules on the cancer cells can bind to the killer immunoglobulin-like receptors (KIRs) and inhibit the NK cell killing. The present invention provides methods and compositions that overcome this inhibition and promotes NK cell killing of cancer cells.

B. T CELLS

In some embodiments, the present invention employs genetically modified T cells in the treatment of hyperproliferative diseases. T cells play a role in cell-mediated immunity. One way in which T cells can be distinguished from other lymphocytes, such as B cells and NK cells, is by the presence on their cell surface of the T cell receptor (TCR). Activation of CD8+ T cells and CD4+ T cells occurs through the engagement of both the T cell receptor and CD28 on the T cell by the major histocompatibility complex (MHC) peptide and B7 family members on an antigen presenting cell (APC). Engagement of the T cell receptor for antigen (TCR) in the absence of CD28 costimulation can result in a long-term hyporesponsive state termed clonal anergy (Schwartz, 2003). Anergic T cells show defective IL-2 production and proliferation upon restimulation via the TCR and CD28, and produce other cytokines at reduced levels. Anergy may represent one mechanism of peripheral tolerance (Ramsdell et al., 1989), and has been reported to occur in the setting of non-productive anti-tumor immunity in vivo (Staveley-O'Carroll et al., 1998).

C. CHIMERIC RECEPTORS

Chimeric receptors generally comprise an extracellular antibody to specific antigen on the target cell surface and an activation/stimulation domain in the cytoplasm. chimeric receptor expression in NK, T, PBL, or PBMC cells directly links the NK, T, PBL, or PBMC cells to target cells and consequently allow NK or T cells to kill the target cells. Under this mechanism, the target cell killing can avoid the HLA-type-related NK cell killing inhibition and T cell receptor (TCR)-requirement for T cell-induced target cell killing. In one embodiment of the invention, the chimeric receptor is an anti-CD19 chimeric receptor comprising a single chain antibody conjugated with the 4-1 BB intracellular domain and the CD3ζ domain. Chimeric receptor molecules are described in US 2004/0038886, which is incorporated herein by reference.

D. HYPERPROLIFERATIVE DISEASES

The invention may be used in the treatment and prevention of hyperproliferative diseases including, but not limited to, cancer. A hyperproliferative disease is any disease or condition which has, as part of its pathology, an abnormal increase in cell number. Included in such diseases are benign conditions such as benign prostatic hypertrophy and ovarian cysts. Also included are premalignant lesions, such as squamous hyperplasia. At the other end of the spectrum of hyperproliferative diseases are cancers. A hyperproliferative disease can involve cells of any cell type. The hyperproliferative disease may or may not be associated with an increase in size of individual cells compared to normal cells.

Another type of hyperproliferative disease is a hyperproliferative lesion, a lesion characterized by an abnormal increase in the number of cells. This increase in the number of cells may or may not be associated with an increase in size of the lesion. Examples of hyperproliferative lesions that are contemplated for treatment include benign tumors and premalignant lesions. Examples include, but are not limited to, squamous cell hyperplastic lesions, premalignant epithelial lesions, psoriatic lesions, cutaneous warts, periungual warts, anogenital warts, epidermdysplasia verruciformis, intraepithelial neoplastic lesions, focal epithelial hyperplasia, conjunctival papilloma, conjunctival carcinoma, or squamous carcinoma lesion. The lesion can involve cells of any cell type. Examples include keratinocytes, epithelial cells, skin cells, and mucosal cells.

E. CANCER

The present invention provides methods and compositions for the treatment and prevention of cancer. Cancer is one of the leading causes of death, being responsible for approximately 526,000 deaths in the United States each year. The term "cancer" as used herein is defined as a tissue of uncontrolled growth or proliferation of cells, such as a tumor.

Cancer develops through the accumulation of genetic alterations (Fearon and Vogelstein, 1990) and gains a growth advantage over normal surrounding cells. The genetic transformation of normal cells to neoplastic cells occurs through a series of progressive steps. Genetic progression models have been studied in some cancers, such as head and neck cancer (Califano et al., 1996). Treatment and prevention of any type of cancer is contemplated by the present invention. The present invention also contemplates methods of prevention of cancer in a subject with a history of cancer. Examples of cancers have been listed above.

F. ELECTROPORATION

Certain embodiments involve the use of electroporation to facilitate the entry of one or more nucleic acid molecules into cells of the immune system, such as natural killer (NK) cells.

As used herein, "electroporation" refers to application of an electrical current or electrical field to a cell to facilitate entry of a nucleic acid molecule into the cell. One of skill in the art would understand that any method and technique of electroporation is contemplated by the present invention. However, in certain embodiments of the invention, electroporation may be carried out as described in U.S. patent application Ser. No. 10/225,446, filed Aug. 21, 2002, the entire disclosure of which is specifically incorporated herein by reference.

In other embodiments of the invention, electroloading may be carried out as described in U.S. Pat. No. 5,612,207 (specifically incorporated herein by reference), U.S. Pat. No. 5,720,921 (specifically incorporated herein by reference), U.S. Pat. No. 6,074,605 (specifically incorporated herein by reference); U.S. Pat. No. 6,090,617 (specifically incorporated herein by reference); and U.S. Pat. No. 6,485,961 (specifically incorporated herein by reference).

Other methods and devices for electroloading that may be used in the context of the present invention are also described in, for example, published PCT Application Nos. WO 03/018751 and WO 2004/031353; U.S. patent application Ser. Nos. 10/781,440, 10/080,272, and 10/675,592; and U.S. Pat. Nos. 6,773,669, 6,090,617, 6,617,154, all of which are incorporated by reference.

G. PHARMACEUTICAL PREPARATIONS

1. Formulations

Pharmaceutical preparations of transfected cells for administration to a subject are contemplated by the present invention. One of ordinary skill in the art would be familiar with techniques for administering cells to a subject. Furthermore, one of ordinary skill in the art would be familiar with techniques and pharmaceutical reagents necessary for preparation of these cell prior to administration to a subject.

In certain embodiments of the present invention, the pharmaceutical preparation will be an aqueous composition that includes the transfected cells that have been modified to express genetically engineered receptor. In certain embodiments, the transfected cell is prepared using cells that have been obtained from the subject (i.e., autologous cells).

Pharmaceutical compositions of the present invention comprise an effective amount of a solution of the transfected cells in a pharmaceutically acceptable carrier or aqueous medium. As used herein, "pharmaceutical preparation" or "pharmaceutical composition" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the transfected cancer cells, its use in the therapeutic compositions is contemplated. Supplementary active ingredients can also be incorporated into the compositions. For human administration, preparations should meet sterility, pyrogenicity, general safety and purity standards as required by the FDA Center for Biologics.

The transfected cancer cells may be formulated for administration by any known route, such as by subcutaneous injection, intramuscular injection, intravascular injection, intratumoral injection, or application by any other route. A person of ordinary skill in the art would be familiar with techniques for generating sterile solutions for injection or application by any other route. Determination of the number of cells to be administered will be made by one of skill in the art, and will in part be dependent on the extent and severity of cancer, and whether the transfected cells are being administered for treatment of existing cancer or prevention of cancer. The preparation of the pharmaceutical composition containing the transfected cells will be known to those of skill in the art in light of the present disclosure. The transfected cells may be administered with other agents that are part of the therapeutic regiment of the subject, such as other immunotherapy or chemotherapy. In some embodiments, about 1e7, 1e8, 1e9, or 1e10, or any range derivable therein, of transfected cells are administered per dose. In certain aspects, multiple doses may be administered over a period of days, weeks, months, or year. A subject may receive, for example, 1, 2, 3, 4, 5, 6, 7, 8, 9, 10, 11, 12, 13, 14, 15, 16, 17, 18, 19, or 20 doses.

H. Examples

The following examples are included to demonstrate certain embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

EXAMPLE 1

Electroloading of NK Cells with a DNA Plasmid Encoding a Marker Gene

Figure 1C:
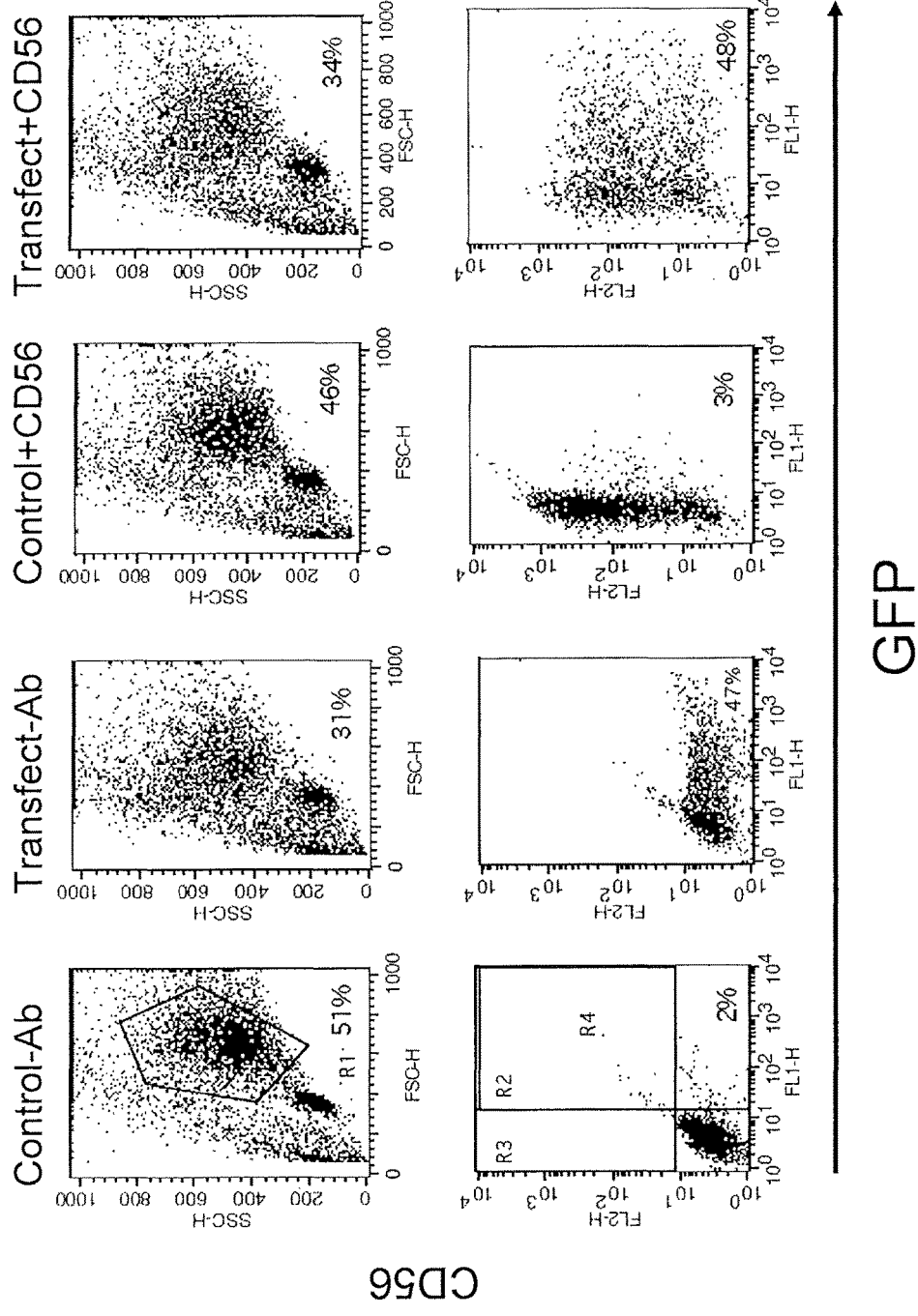

NK cells were transfected using electroporation with a DNA plasmid carrying an eGFP marker gene. One day after transfection, the viable and transfected NK cells were assayed and found to be about 50% and 30% respectively, as shown in FIG. 1C. When normalized to untransfected control cells, the viability of transfected NK cells using this plasmid DNA was about 60%. Approximately 50% of the viable NK cells expressed the eGFP marker gene. No significant change in phenotype was observed. Even though NK cells could be transfected well 1 day post transfection, the transfected NK cells lost their proliferation ability and viability because of DNA-uptake mediated cytotoxicity. DNA transfection of NK cells, therefore, would not result in meaningful clinical application.

EXAMPLE 2

Electroloading of Expanded NK Cells with mRNA Coding for a Marker Gene

Figure 1D:
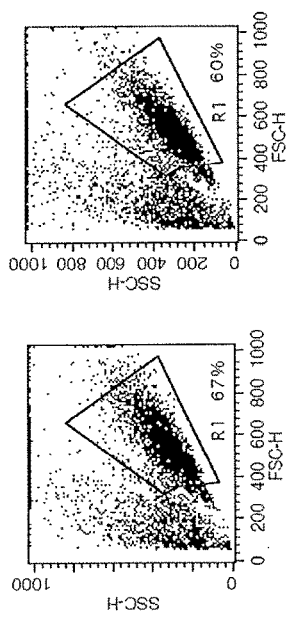
Figure 1D:
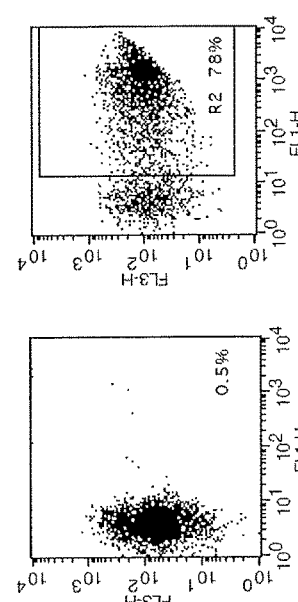
Figure 1D:
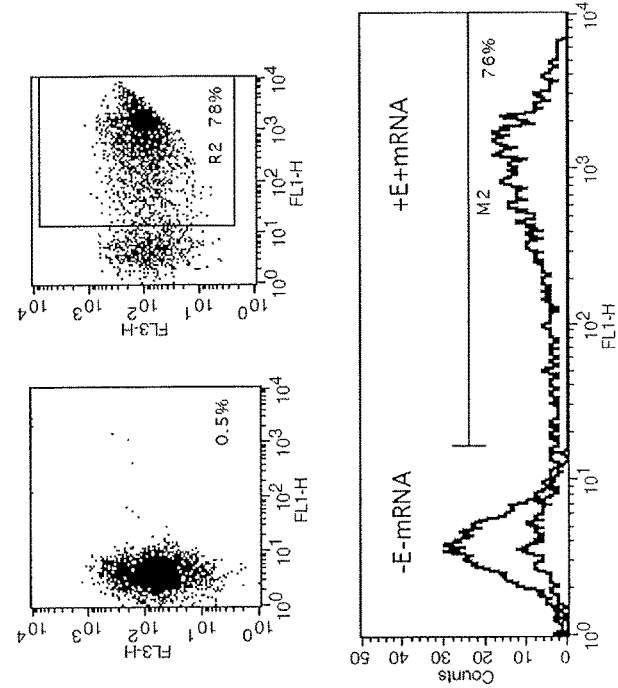
Figure 1E:
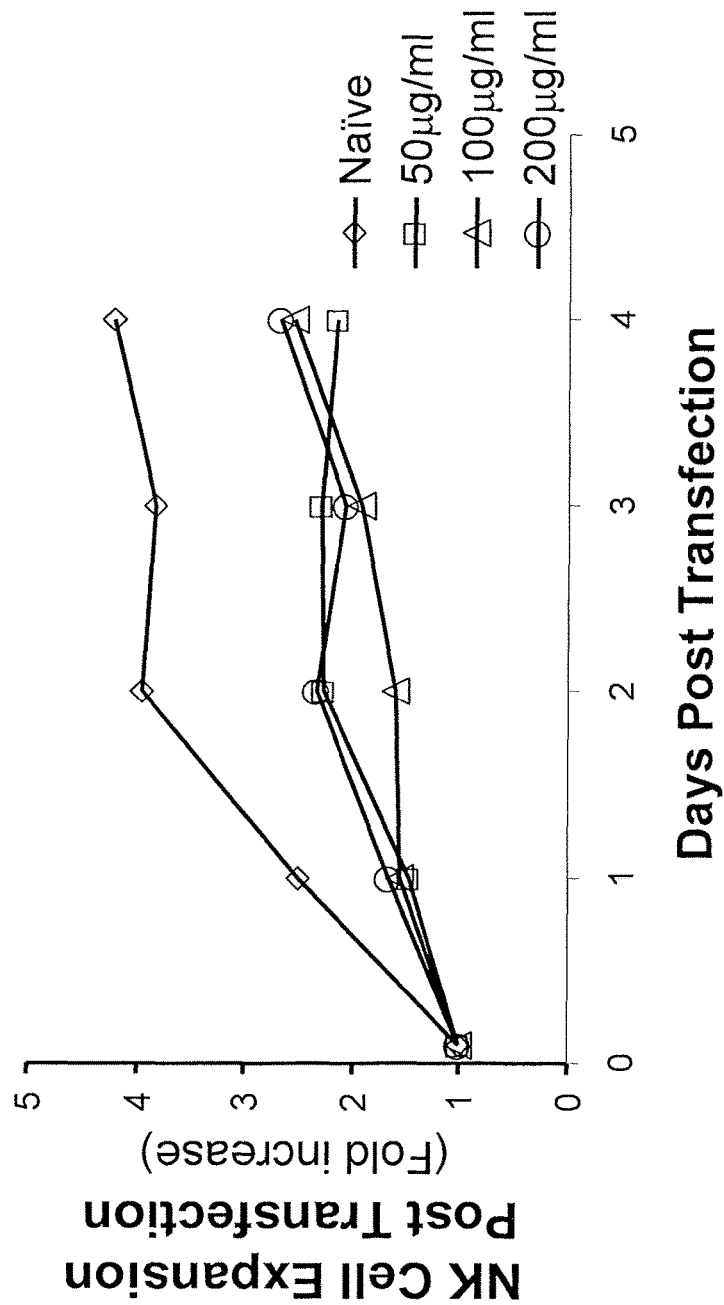

As shown in FIG. 1D, mRNA coding for eGFP was electrotransfected into expanded NK cells. About 80% of the viable cells expressed GFP. At the same time, the viability of NK cells was 67% in the untransfected control and 60% in the transfected cells. When normalized to the untransfected control cells, the viability of the transfected cells was 90%. The mRNA-transfected cells exhibited a reduced rate of cell division for one day post-transfection, but they regained the normal cell division rate subsequently. The transfected NK cells maintained approximately half of the cell number relative to control untransfected cells 4 days post-transfection (FIG. 1E).

EXAMPLE 3

Electroloading of Expanded NK Cells with mRNA Coding for a Chimeric Receptor

Figure 2A:
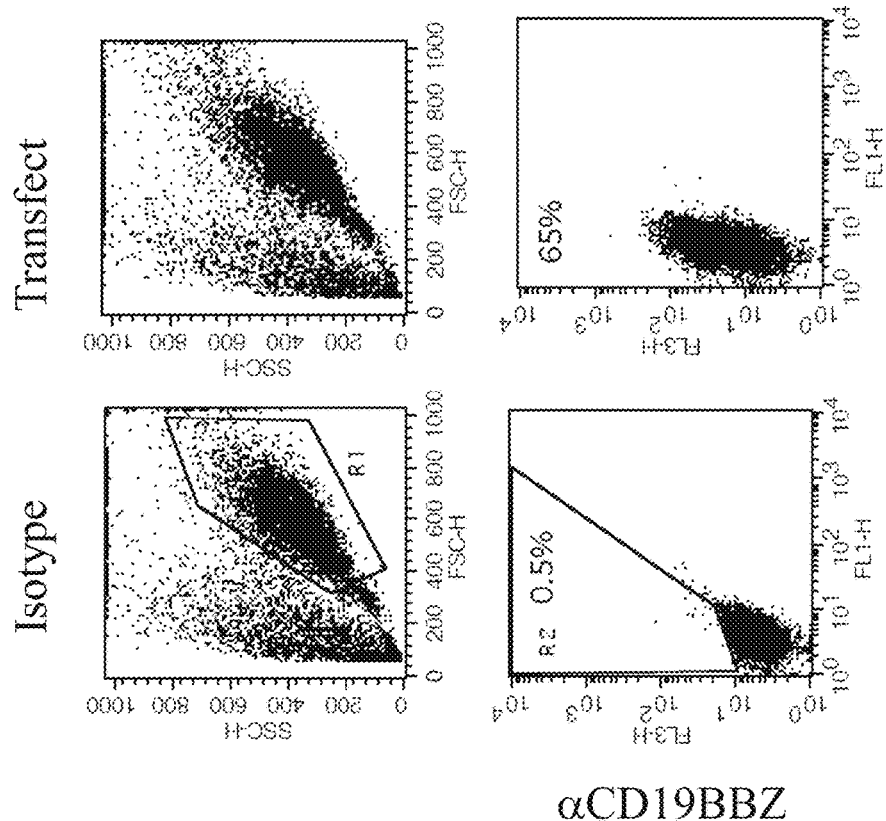
FIGS. 2A-2B. Transfection of mRNA encoding anti-CD19 chimeric receptor in expanded NK cells.
Figure 2B:
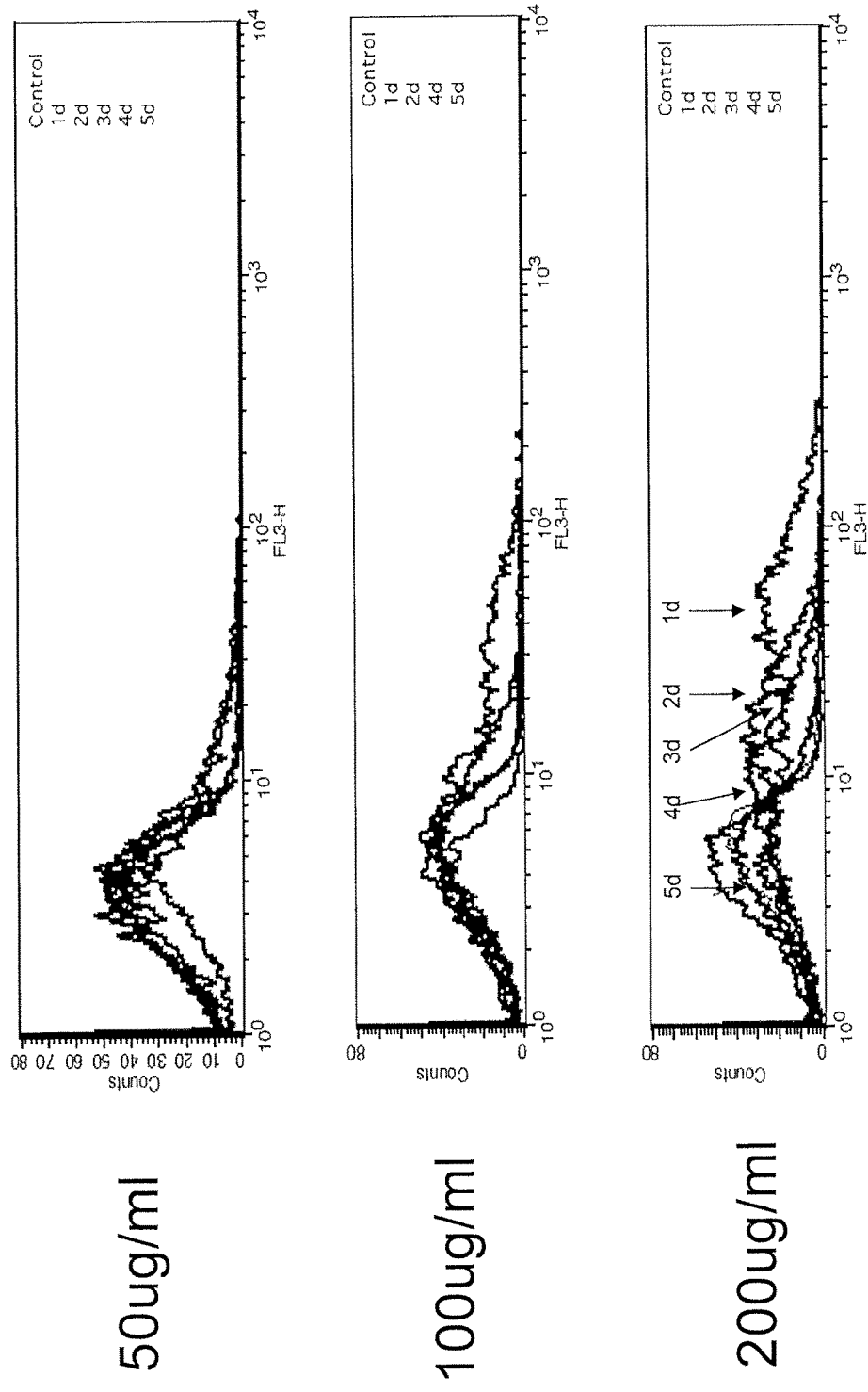

An mRNA coding for an anti-CD19 chimeric receptor was loaded into NK cells by electroloading. As shown in FIG. 2A, 65% of all the viable cells expressed the anti-CD19 chimeric receptor as analyzed by flow cytometry one day post-transfection. The expression of the anti-CD19 chimeric receptor increased with the increase of mRNA concentration used in the electroloading. Using an mRNA concentration of 200 µg/ml, expression of anti-CD19 chimeric receptor was observed for 4 days following electroloading (FIG. 2B). Recovery of the anti-CD19 chimeric receptor-modified NK cells was similar to that of cells electrotransfected with an mRNA coding for the marker gene eGFP.

EXAMPLE 4

Electroloading of Unstimulated Resting NK Cells

Figure 3A:
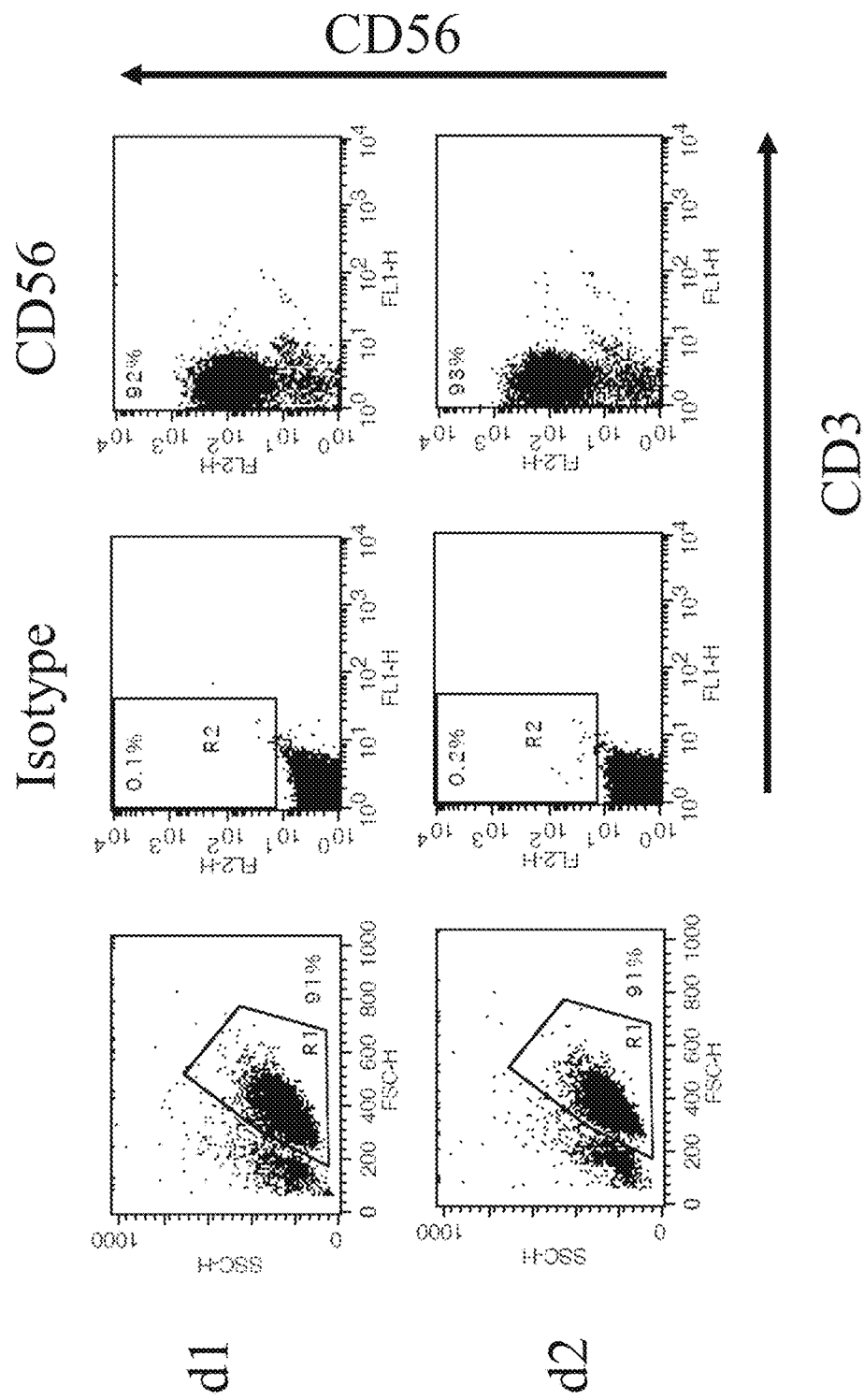
FIGS. 3A-3D. Resting NK cells could be efficiently transfected with mRNA.
Figure 3B:
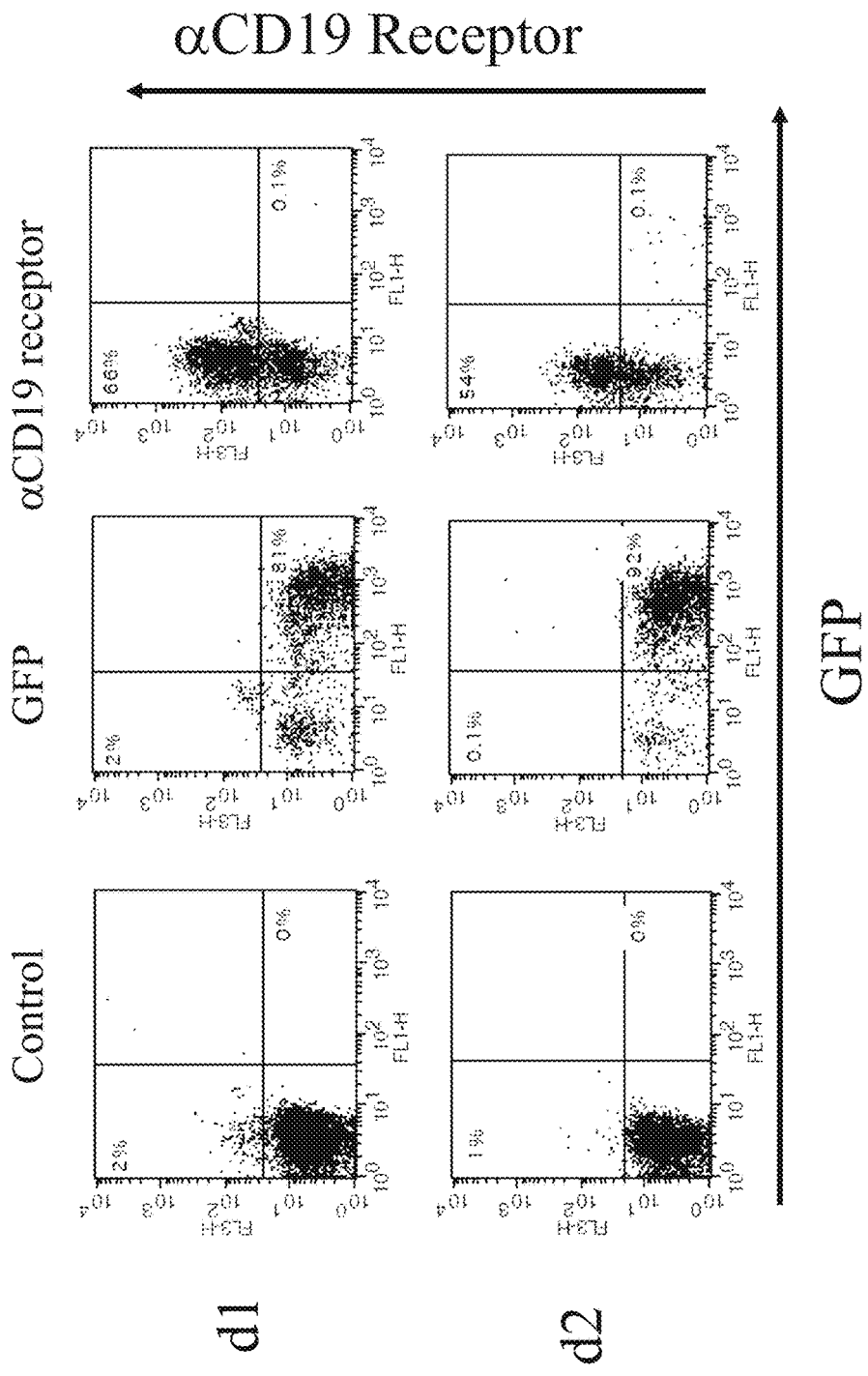
Figure 3C:
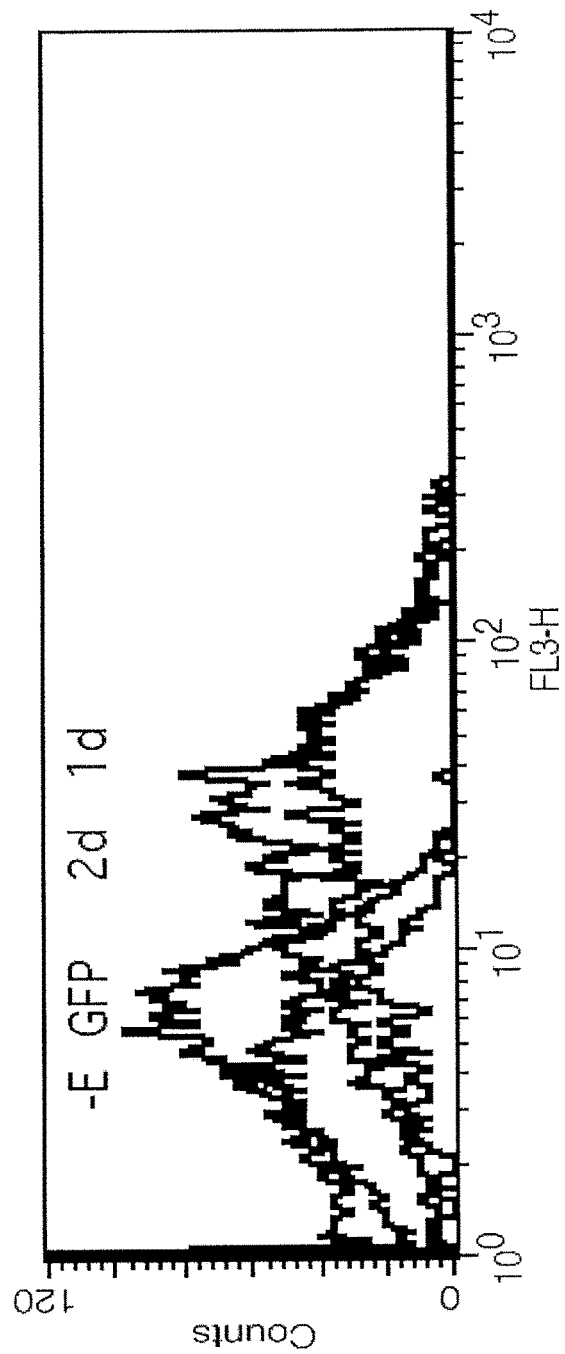
Figure 3D:
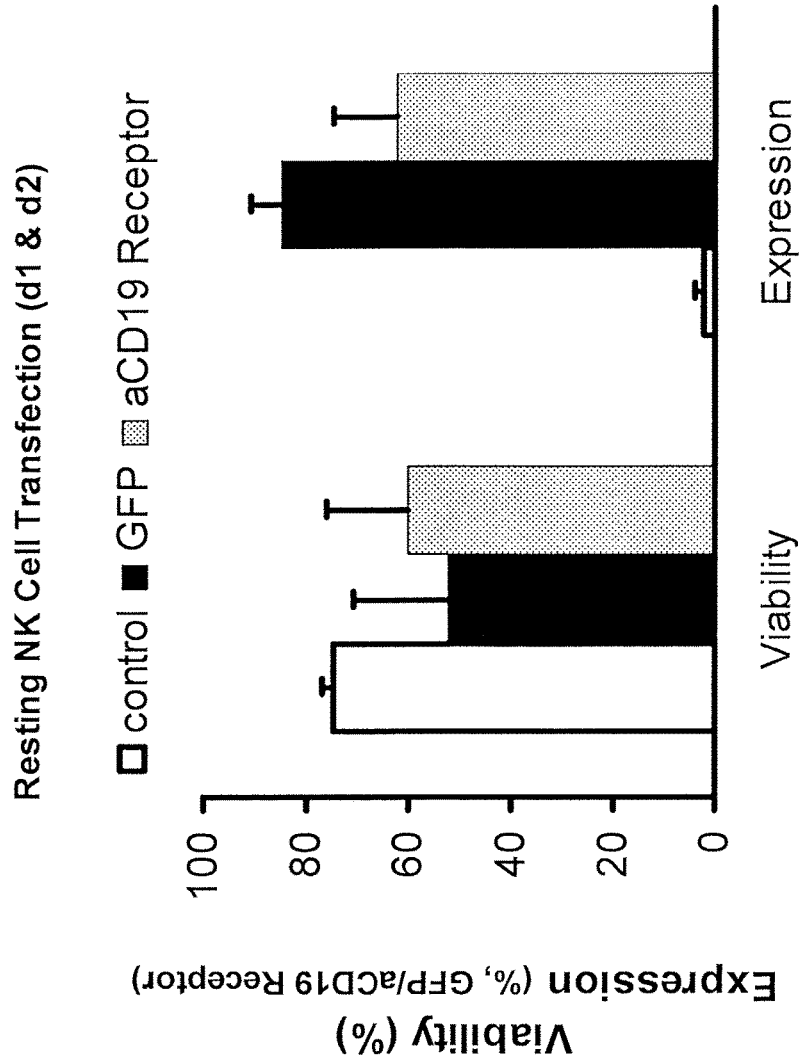

Freshly collected resting NK cells were isolated from a peripheral blood mononuclear cells (PBMC) population using immunoabsorbtion to magnetic beads (Miltenyi Biotec, CD56+ NK Cell Isolation Kit). NK cells were negatively selected attaining >90% purity with representation by minimal CD3+ cells (FIG. 3A). Electroloading of mRNA encoding for anti-CD19 chimeric receptor resulted in expression of anti-CD19 chimeric receptor in between 50 and 60% of electro-loaded resting NK cells (FIG. 3B) 1 day post-transfection. No significant decrease in the expression of anti-CD19 chimeric receptor was observed in the electrotransfected NK cells 2 days post-transfection from 1 day post-transfection (FIG. 3C). The viability of un-electroporated control cells and electrotransfected NK cells at 1 day post-transfection was 75% and 60% respectively, and was about 80% for transfected cells when normalized against un-electroporated control cells (FIG. 3D). GFP expression of resting NK cells (>80%) and expanded NK cells (~80%, see Example 2 above) when electrotransfected with mRNA encoding for eGFP was much more efficient compared to the GFP expression of expanded NK cells (~50%) electrotransfected with DNA plasmid encoding eGFP.

EXAMPLE 5

Figure 4A:
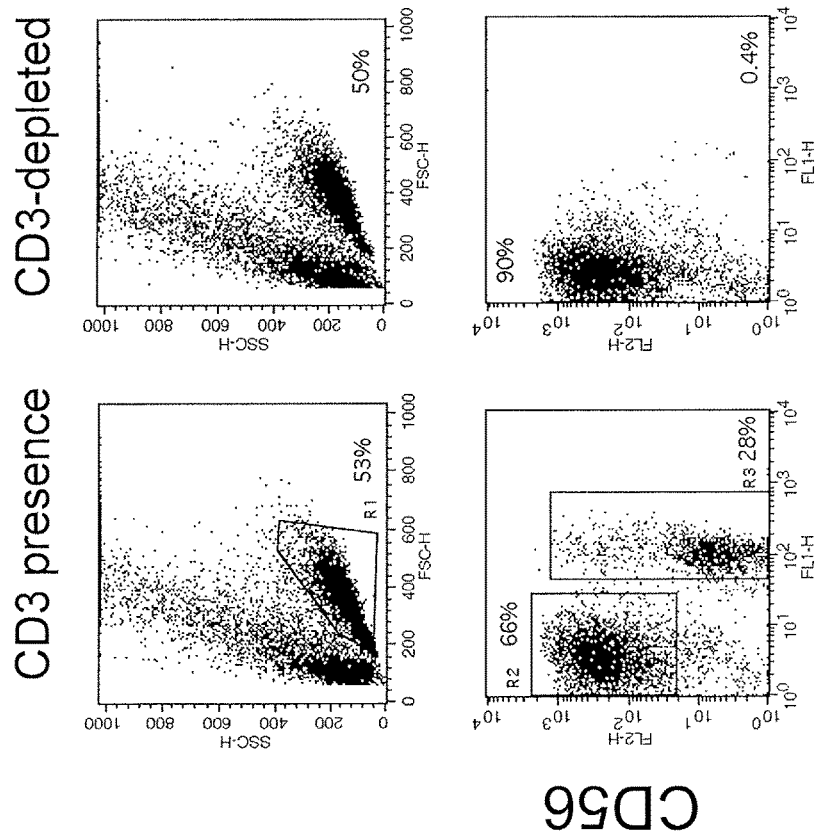
FIGS. 4A-4B. Effect of CD3+ cells on OP-1 killing by transfected NK cells.
Figure 4B:
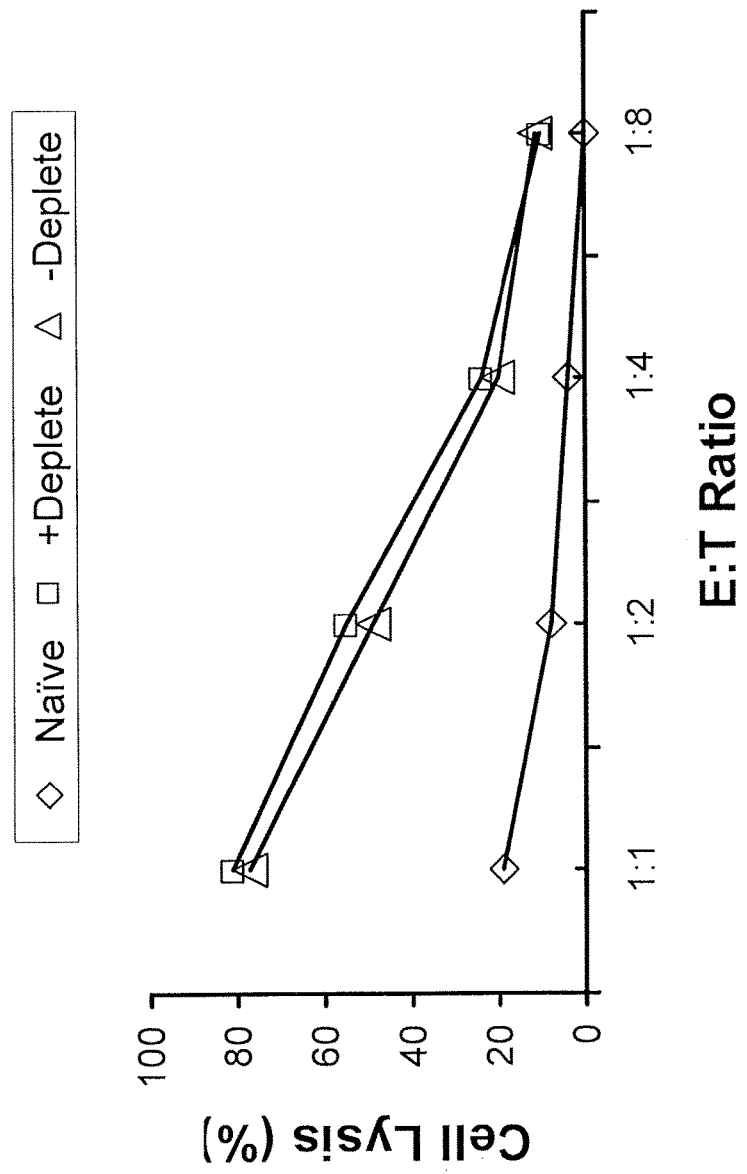

Killing of Leukemia Cells by NK Cells Electrotransfected with mRNA Encoding a Chimeric Receptor To assay specific killing of leukemia cells by NK cells electrotransfected by mRNA coding for a chimeric anti-CD19 receptor the cell line OP-1 was used as a target cell. Lysis was carried out in the presence or absence of CD3+ cells. Depletion of CD3+ cells in the expanded NK cell population using Dynal beads conjugated with anti-CD3 antibody (Invitrogen, Carlsbad, Calif.) designed for removal of CD3+ cells by positive selection following the manufacture's protocol was carried out immediately prior to electroloading with the mRNA encoding for the chimeric anti-CD19 receptor (FIG. 4A). FIG. 4B shows the similar killing curve derived from the samples either with or without CD3+ cell depletion.

Figure 5A:
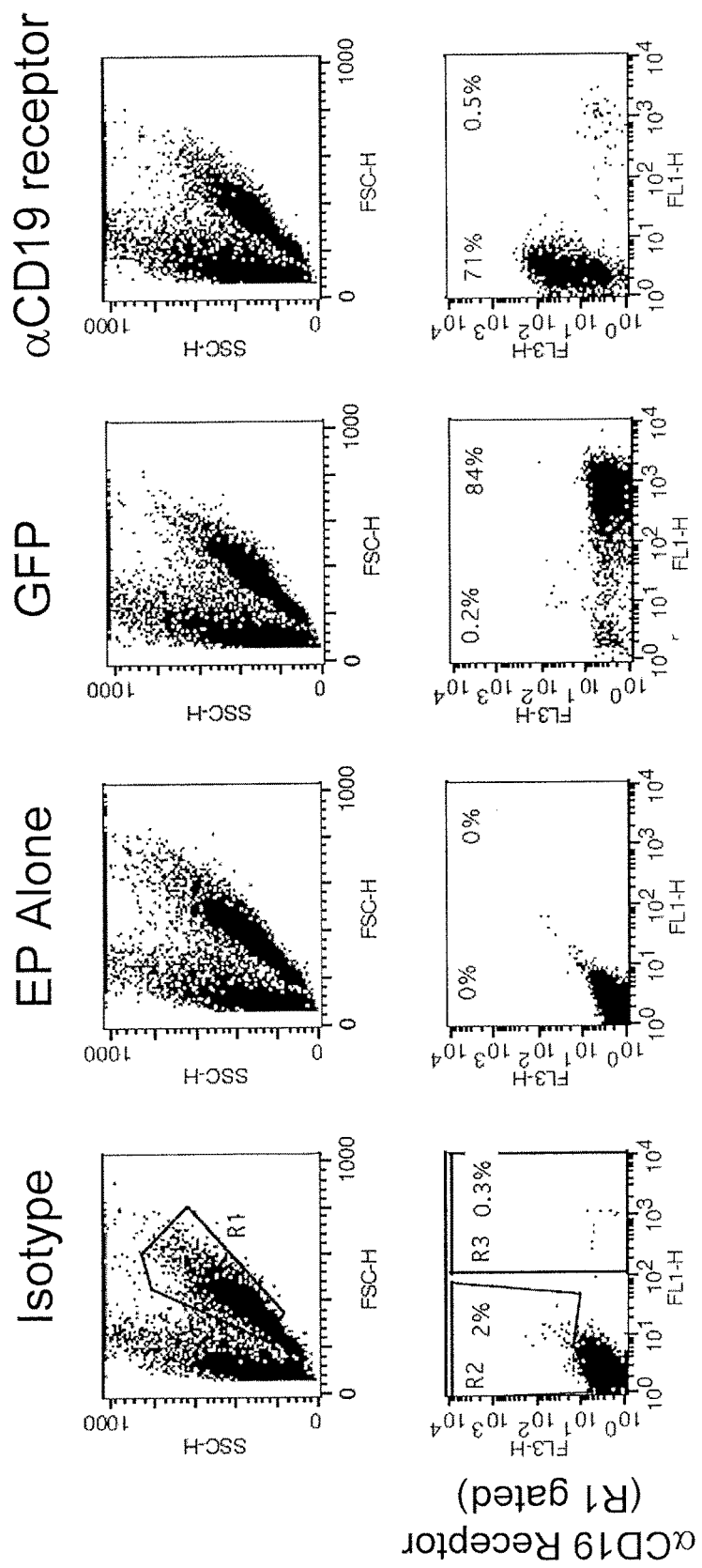
FIGS. 5A-5C. Specificity of NK cell killing.
Figure 5B:
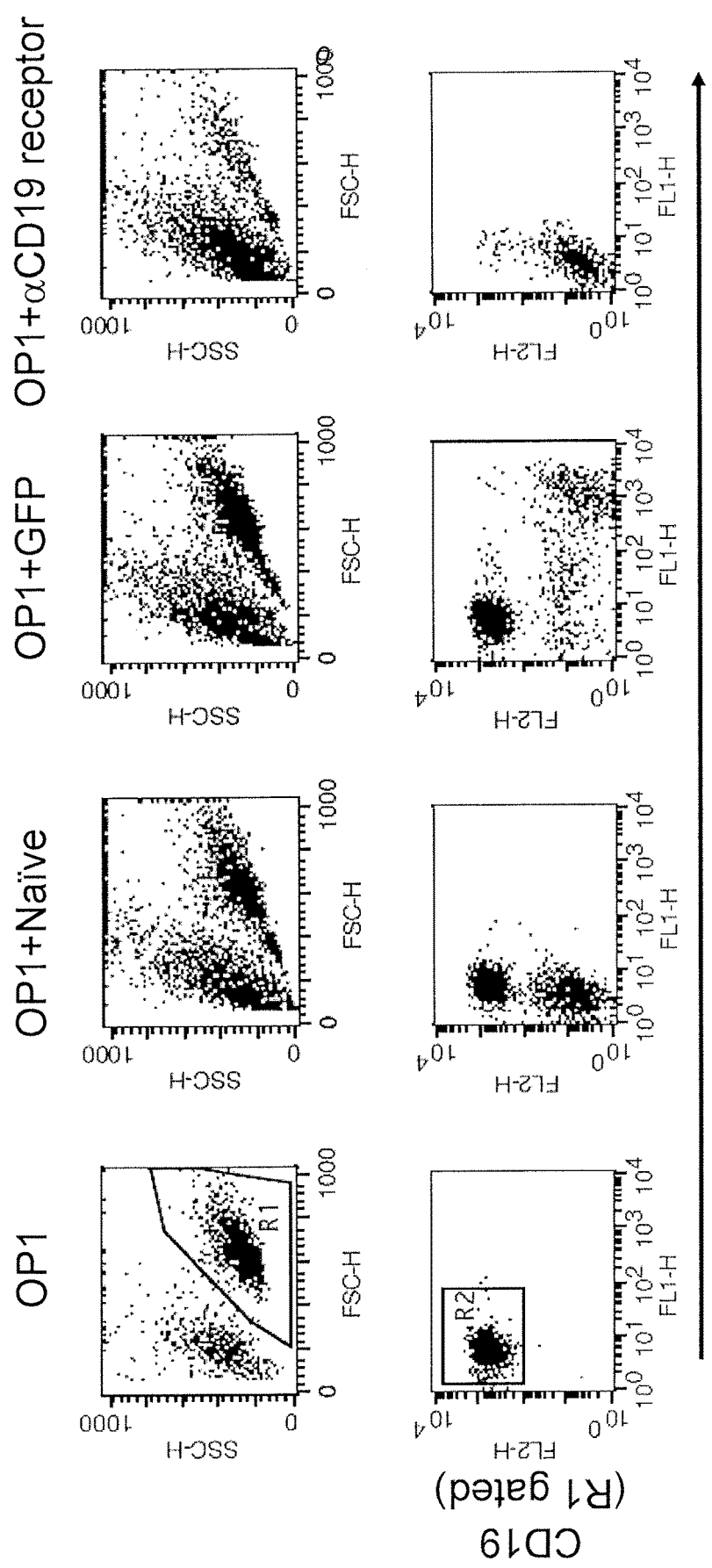
Figure 5C:
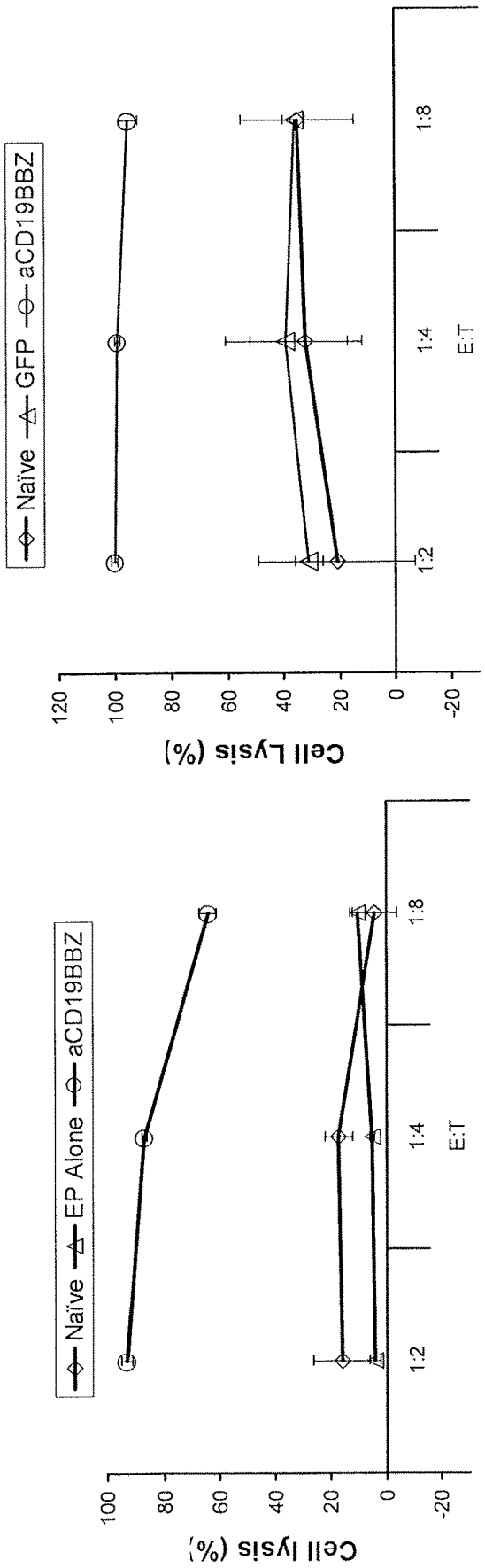

The specificity of anti-CD19 chimeric receptor for killing leukemic cells was confirmed by comparing killing by NK cells electrotransfected using mRNA encoding for the chimeric anti-CD19 receptor to otherwise identical NK cells electrotranfected using mRNA encoding for the marker gene eGFP or cells that received the same electroporation treatment absent any exogenous mRNA. NK cells electroporated in the absence of exogenous mRNA, NK cells electrotransfected using mRNA coding for eGFP and NK cells electrotransfected using mRNA coding for the chimeric anti-CD19 receptor exhibited similar cell viability following electroloading (FIG. 5A). NK cells electroporated in the absence of exogenous mRNA, and NK cells electrotransfected using mRNA coding for eGFP both failed to kill calcein labeled OP-1 leukemia cells (FIGS. 5B and 5C). NK cells electrotransfected using mRNA encoding for the chimeric anti-CD19 receptor when mixed with calcein labeled OP-1 cells resulted in significant lysis of the target labeled OP-1 cells (FIGS. 5B and 5C).

Figure 6A:
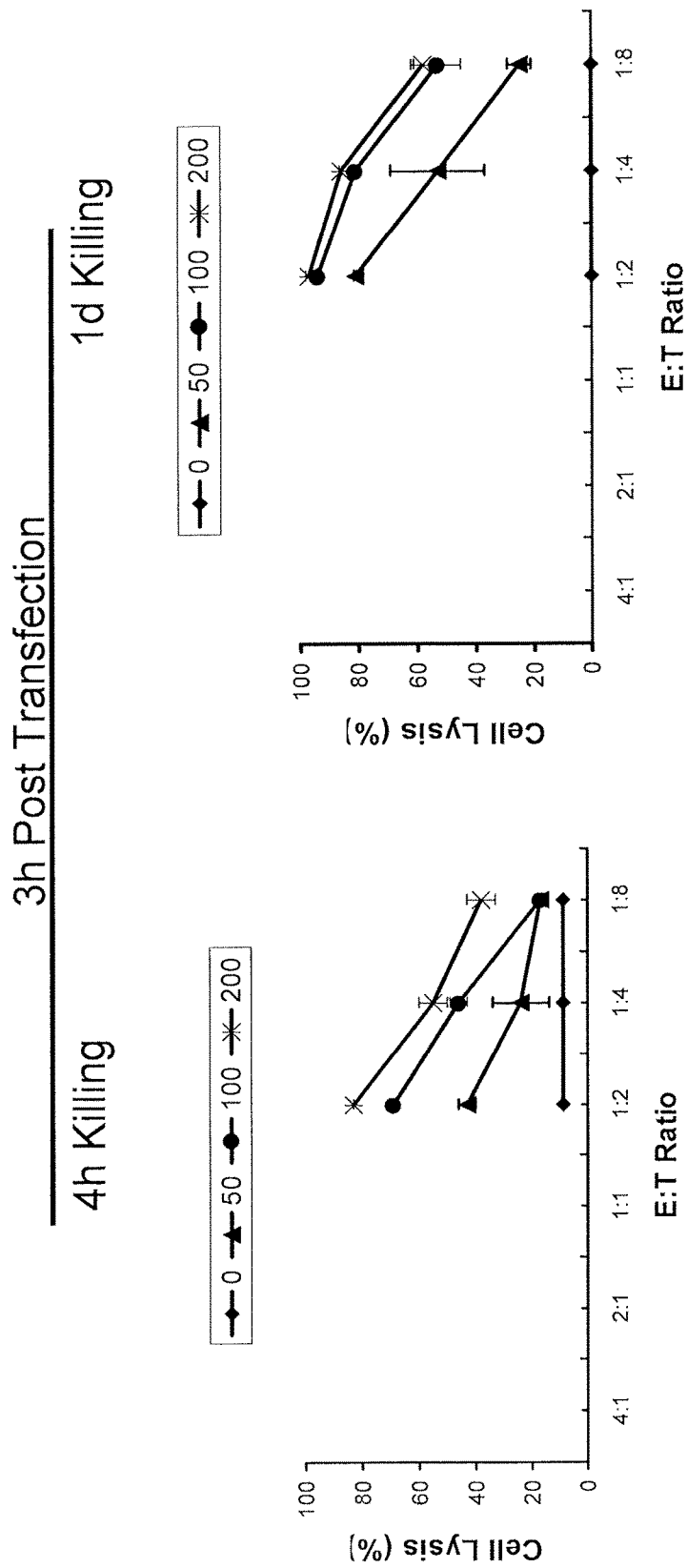
FIGS. 6A-6D. Duration of killing by expanded NK cells transfected with anti-CD19 chimeric receptor. Killing was analyzed by calcein-AM method, set up at 3 h (FIG. 6A), 1 day (FIG. 6B), 2 days (FIG. 6C), and 3 days (FIG. 6D) post transfection, and analyzed after 4 hours or 1 day killing.
Figure 6B:
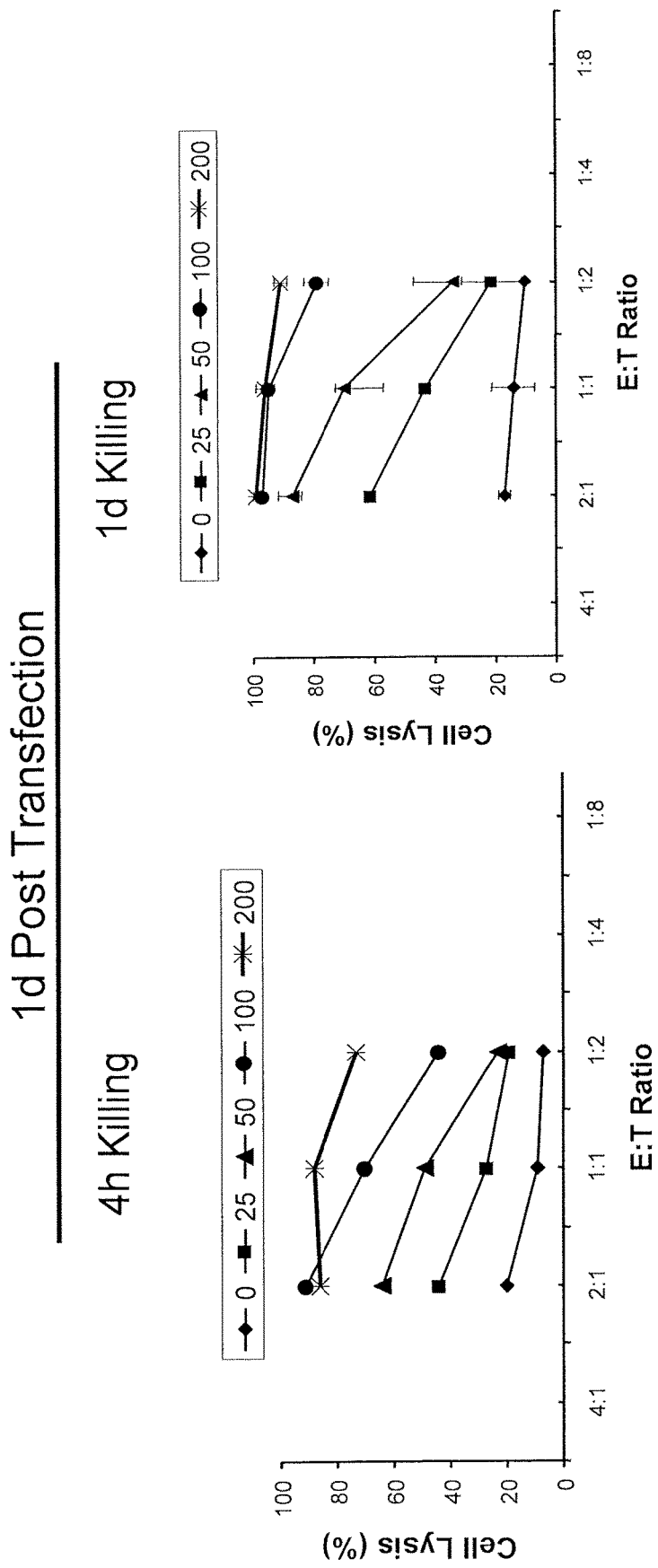
Figure 6C:
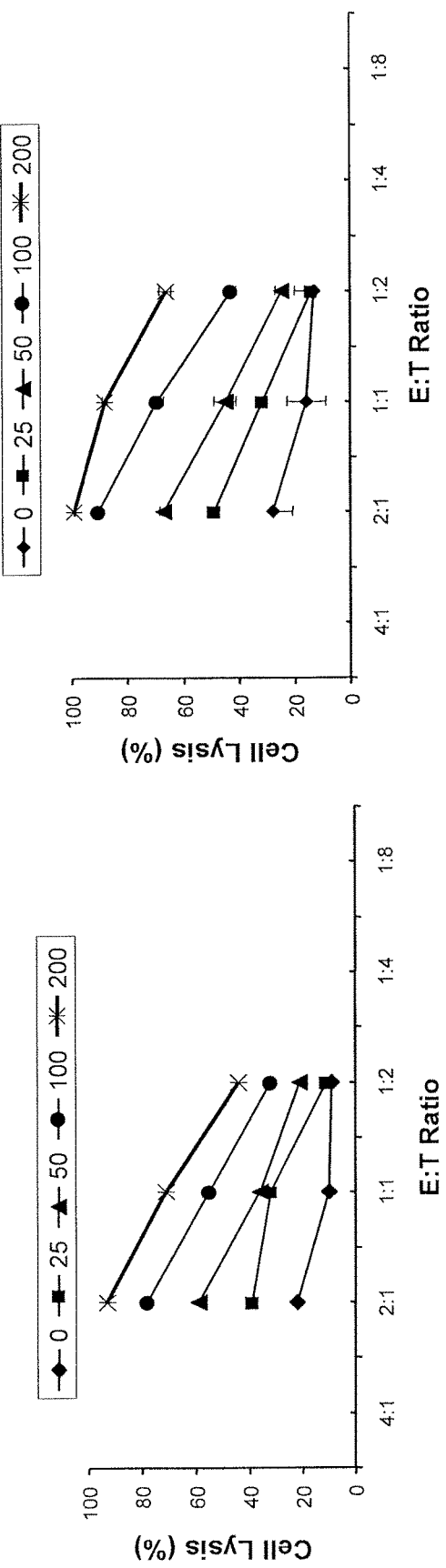
Figure 6D:
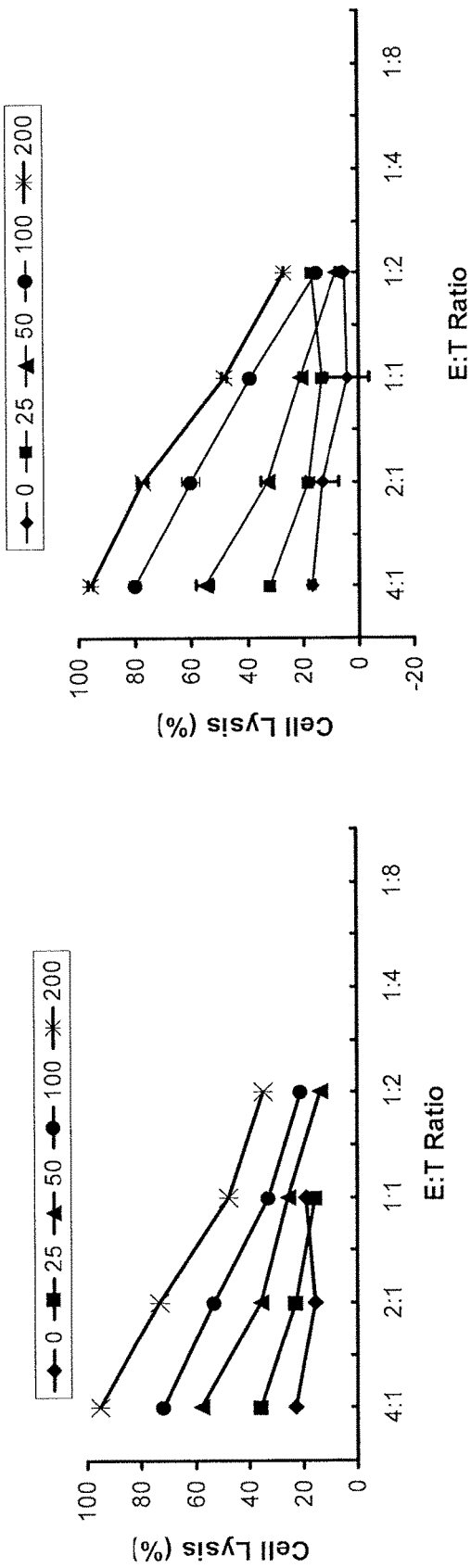
Figure 7A:
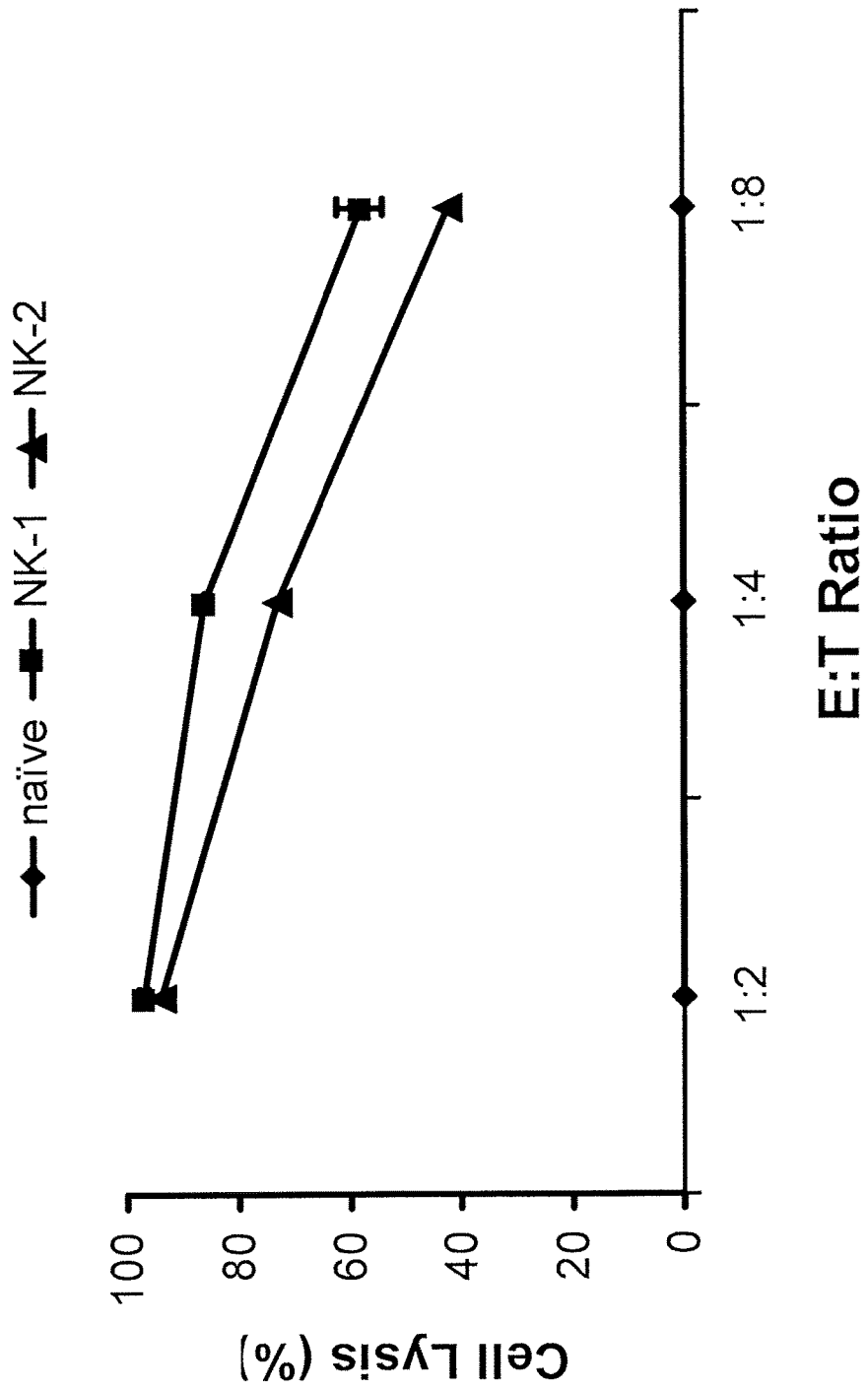
FIGS. 7A-7B. OP-1 cell killing by NK cells from two different donors.

Specific lysis of labeled OP-1 cells by NK cells electrotransfected using mRNA encoding for the chimeric anti-CD19 receptor was proportional to the concentration of the mRNA encoding for the chimeric anti-CD19 receptor. Cell killing was seen as early as 3 hours post transfection (FIG. 6A). Four hours of co-culture resulted in approximately 80% lysis of the OP-1 cells at a ratio of 1:2 (effector:target (E:T)). Overnight co-culture resulted in almost 100% lysis of the OP-1 cells at the same 1:2 ratio. Anti-CD19 chimeric receptor-transfected cells maintained their specific killing activity for 3 days post transfection, as shown in FIGS. 6A-6D. On day 3 post transfection, anti-CD19 chimeric receptor-transfected cells lysed 80% and 100% of the target OP-1 cells after 4 hours of co-culture at 2:1 and 4:1 E:T ratio respectively (FIG. 6D). FIG. 7A summarizes cytotoxicty results of primary NK cells derived from two different donors. Anti-CD19 chimeric receptor electrotransfected NK cells from both donors showed similar target cell lysis efficiency and kinetics.

Figure 7B:
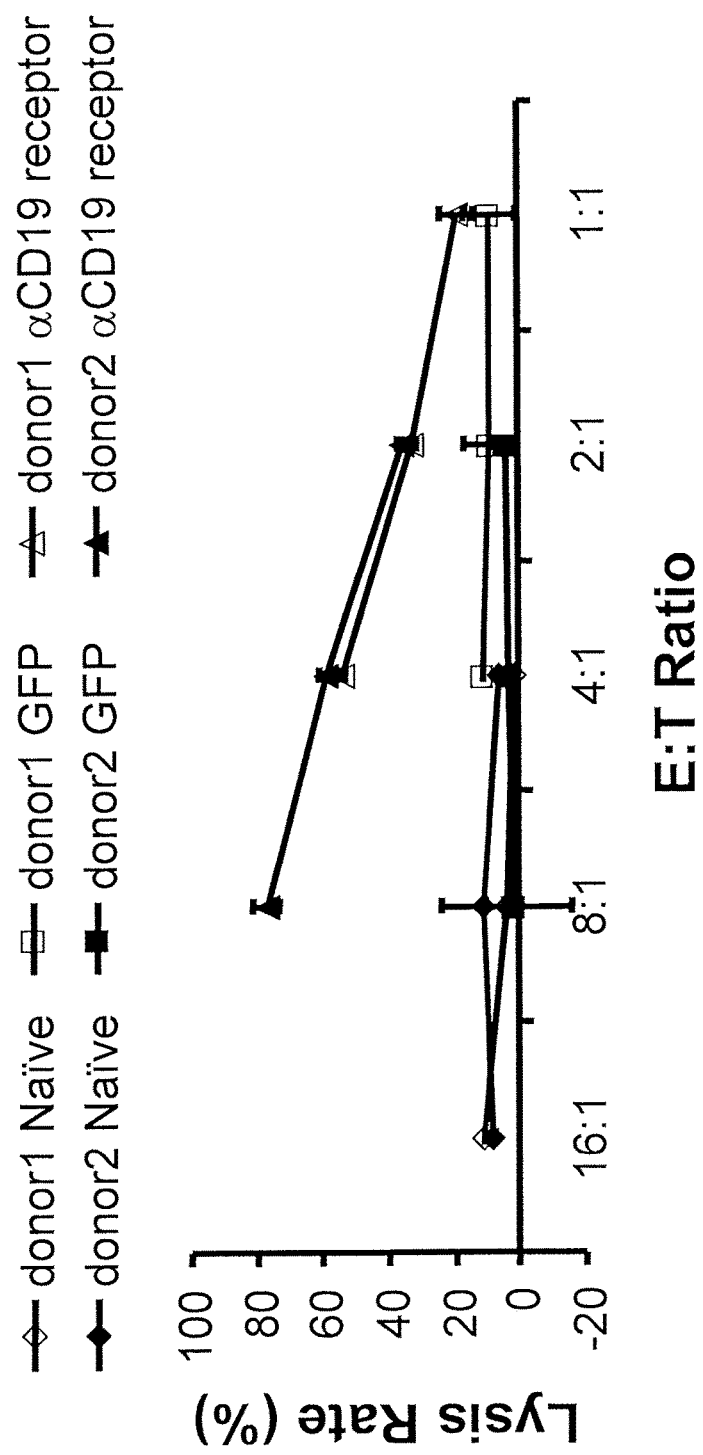

Specific killing of target cell line OP-1 by resting NK cells 1 day after electroloading was assayed. As shown in FIG. 7B, the anti-CD19 chimeric receptor-electro-loaded resting NK cells could efficiently kill OP-1 cells. At an E:T ratio of 8:1, about 80% of the target cells were lysed in the 4 hour co-cultivation killing assay. The naïve and GFP-expressing resting NK cells did not lyse target OP-1 cells. Resting NK cells from both donors demonstrated similar lysis activity.

EXAMPLE 6

Figure 8A:
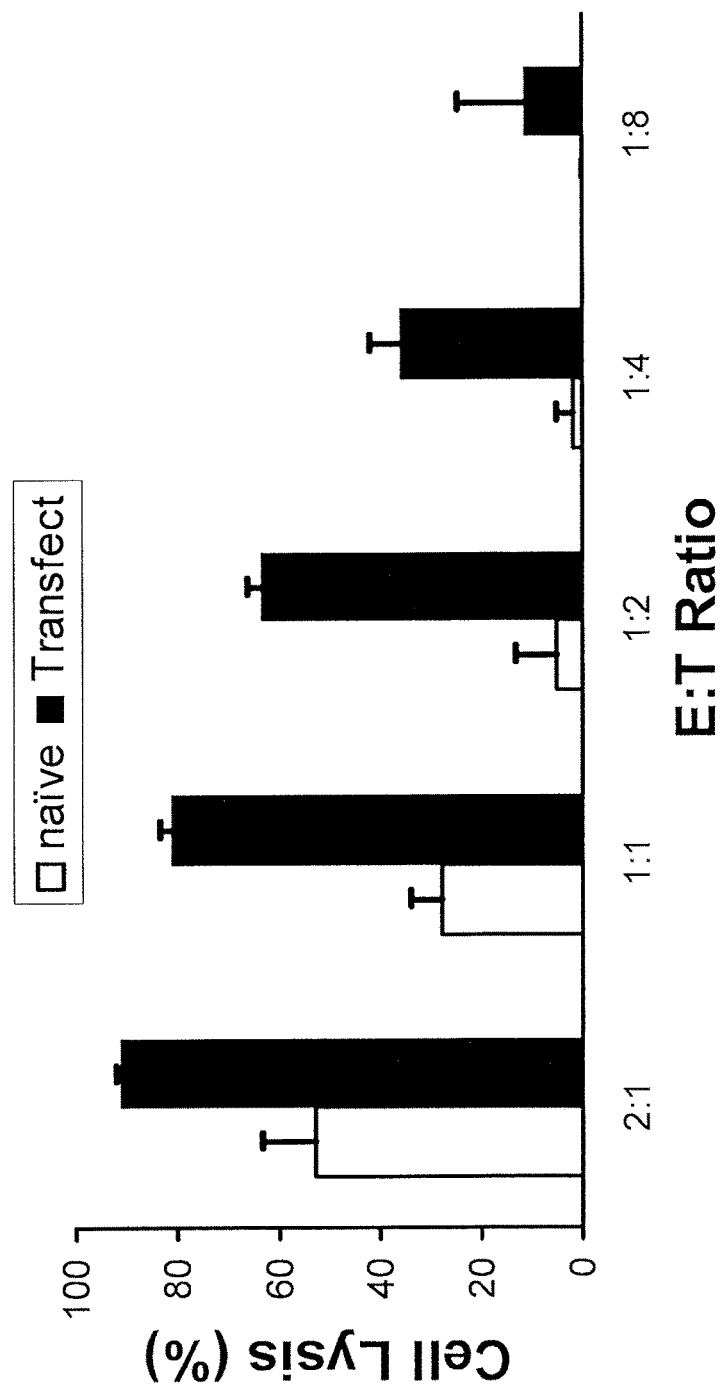
FIGS. 8A-8B. Allogeneic primary B-CLL cell killing by anti-CD19 chimeric receptor-expressed NK cells.
Figure 8B:
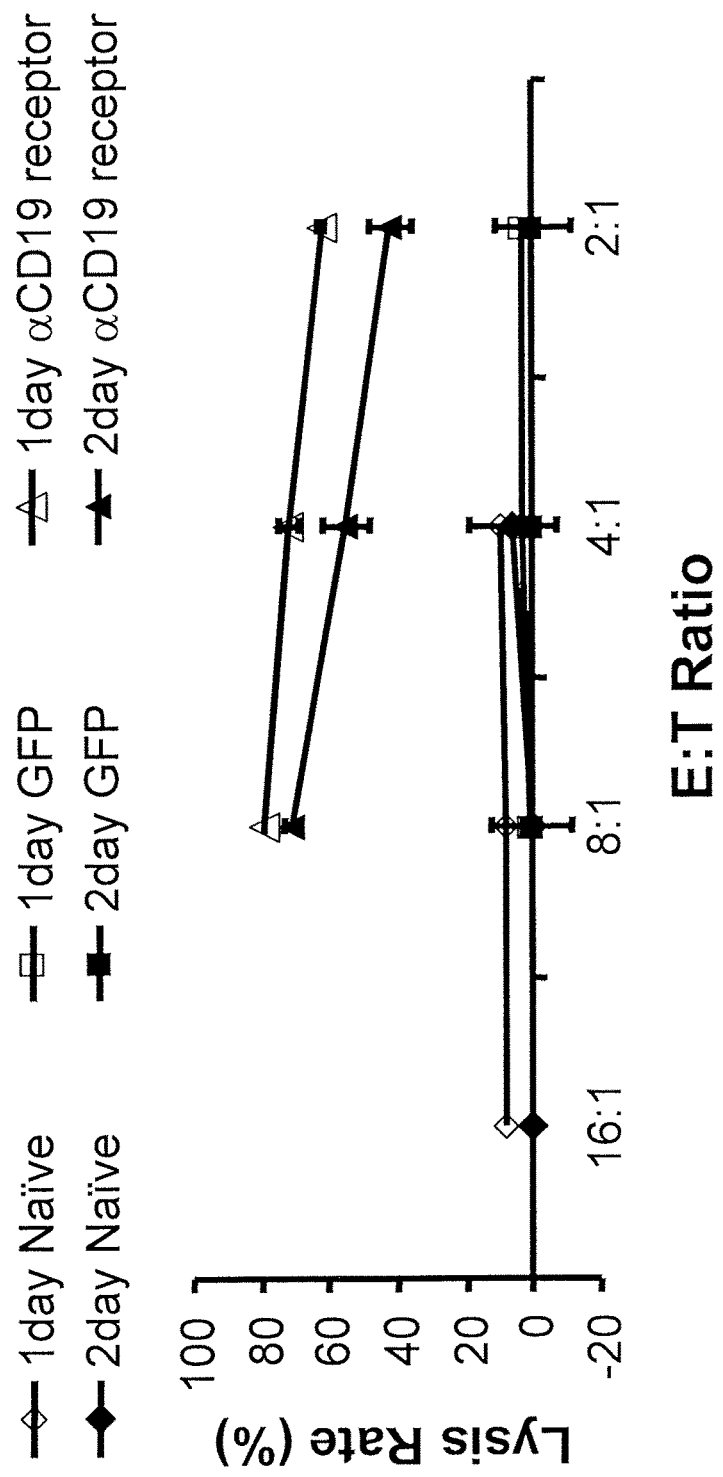

Resting NK Cells Electrotransfected Using mRNA Encoding for the Chimeric Anti-CD19 Showed Specific Killing of Allogeneic Primary B-Lineage Leukemia Cells NK cells were electrotransfected using a mRNA encoding for the chimeric anti-CD19 receptor, mRNA encoding for eGFP, and NK cells electroporated in the absence of exogenous mRNA were assayed for their ability to specifically lyse labeled B-CLL target cells. A significant percentage of B-CLL cells were lysed by NK cells electrotransfected using mRNA encoding for the chimeric anti-CD19 receptor as compared to NK cells electrotransfected using an mRNA encoding for eGFP or NK cells electroporated in the absence of exogenous mRNA. Target B-CLL from two donors were used in these assays and the results were summarized in FIG. 8A. Resting NK cells electrotransfected using a mRNA encoding for the chimeric CD19 receptor could kill B-CLL cells at least for two days after transfection (FIG. 8B) and the killing of these labeled B-CLL cells was significantly higher than by either the NK cells electrotransfected using mRNA encoding for eGFP or NK cells electroporated in the absence of exogenous mRNA.

EXAMPLE 7

DNA Uptake is Toxic to Resting PBLs

Figure 9A:
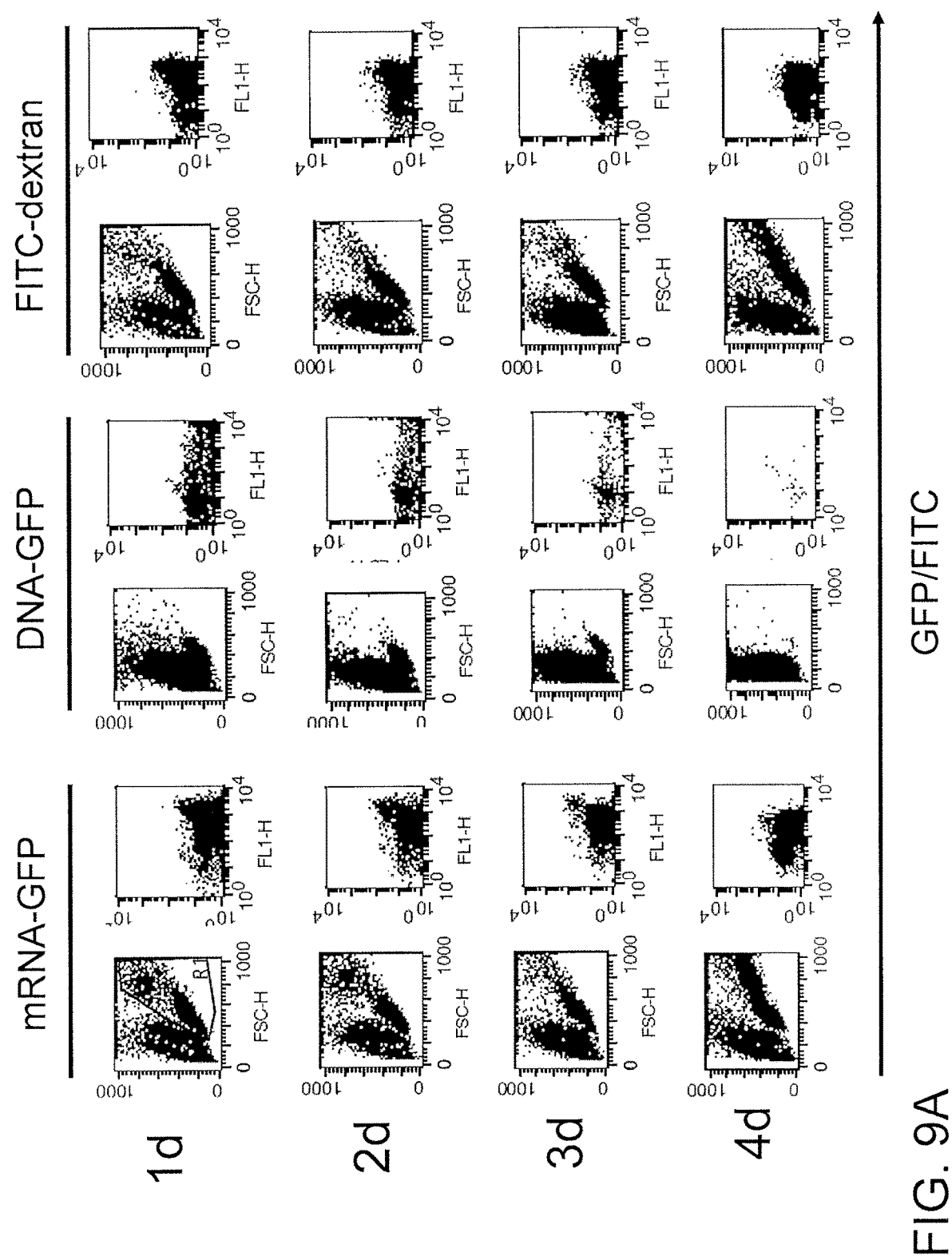
FIGS. 9A-9D. DNA uptake is toxic to resting PBL. Resting PBL was electroporated in the presence of plasmid DNA encoding for eGFP under CMV promoter, mRNA encoding for the eGFP and macromolecule FITC-dextran (500 kD). The viability and the expression level were monitored by trypan blue exclusion and flow cytometry analysis for up to 7 days post transfection.
Figure 9B:
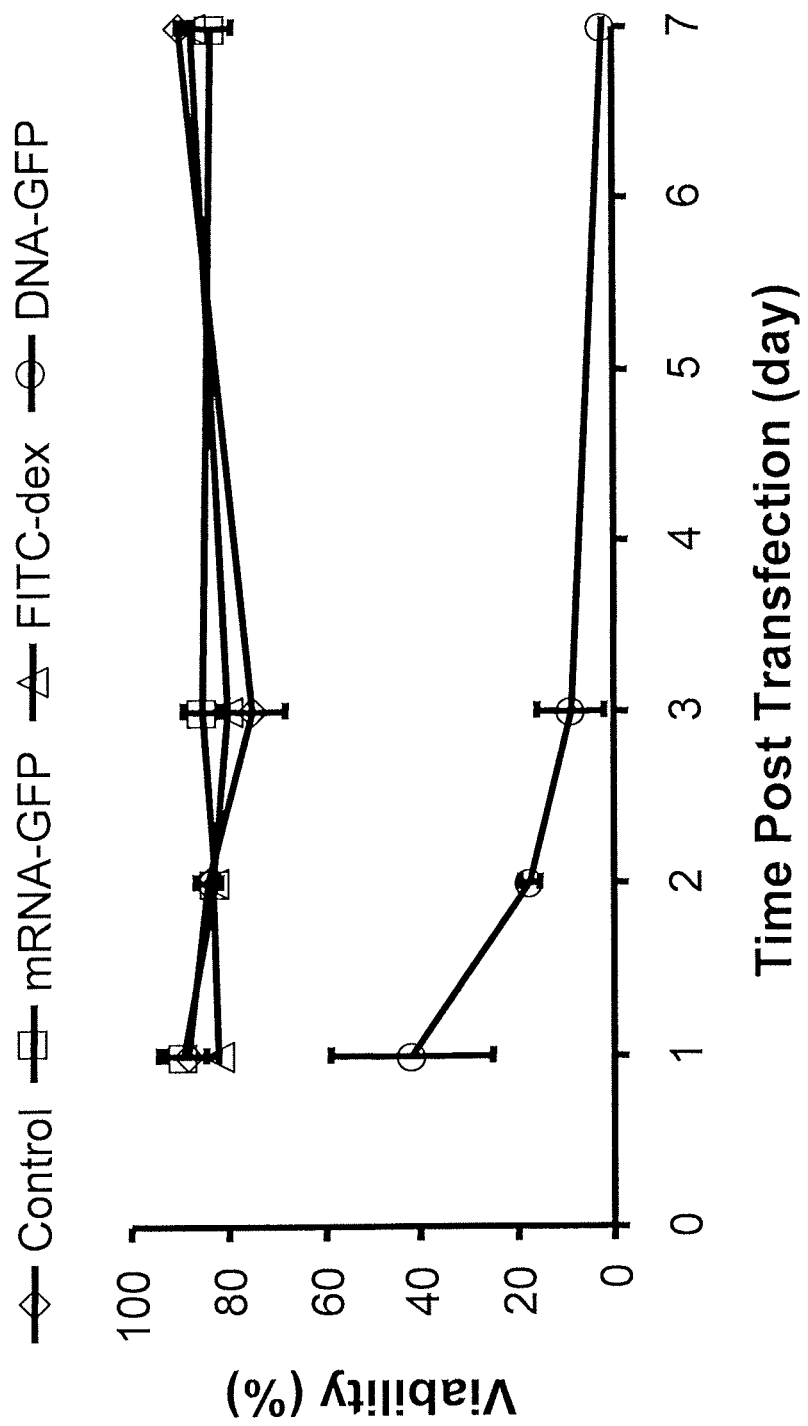
Figure 9C:
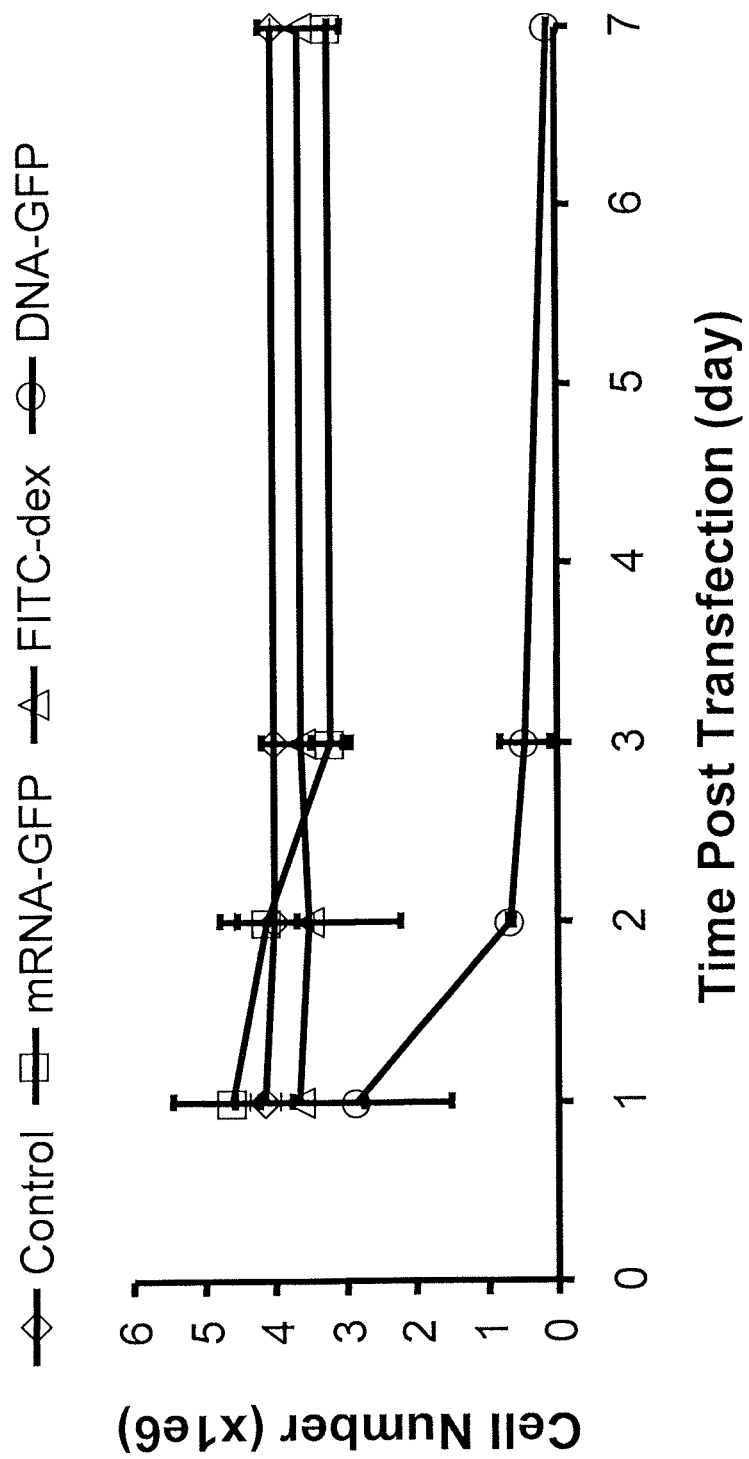
Figure 9D:
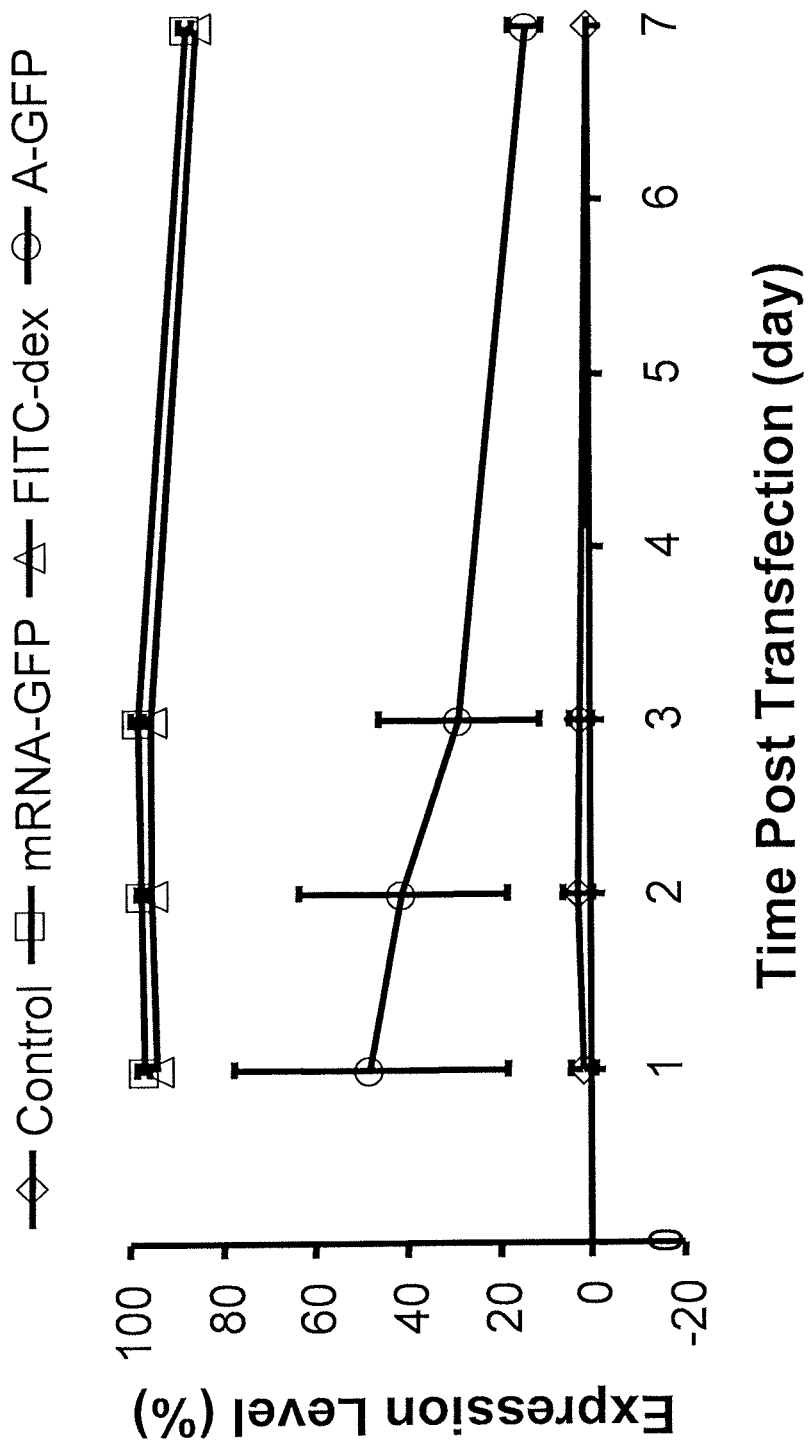

Resting PBLs were electroporated in the presence of plasmid DNA encoding for eGFP under the control of a CMV promoter, mRNA encoding for the eGFP, and macromolecule FITC-dextran (500 kD). The viability and the expression level were monitored by trypan blue exclusion and flow cytometry analysis for up to 7 days post transfection. FIG. 9A shows typical FACS analysis data. As shown in FIGS. 9B and 9C, the viability of cells electroporated in the presence of DNA was much lower in comparison to cells electroporated with mRNA or FITC-dex. In addition, GFP expression was much lower in cells transfected with the DNA-GFP as compared to the mRNA-GFP (FIG. 9D).

Figure 10A:
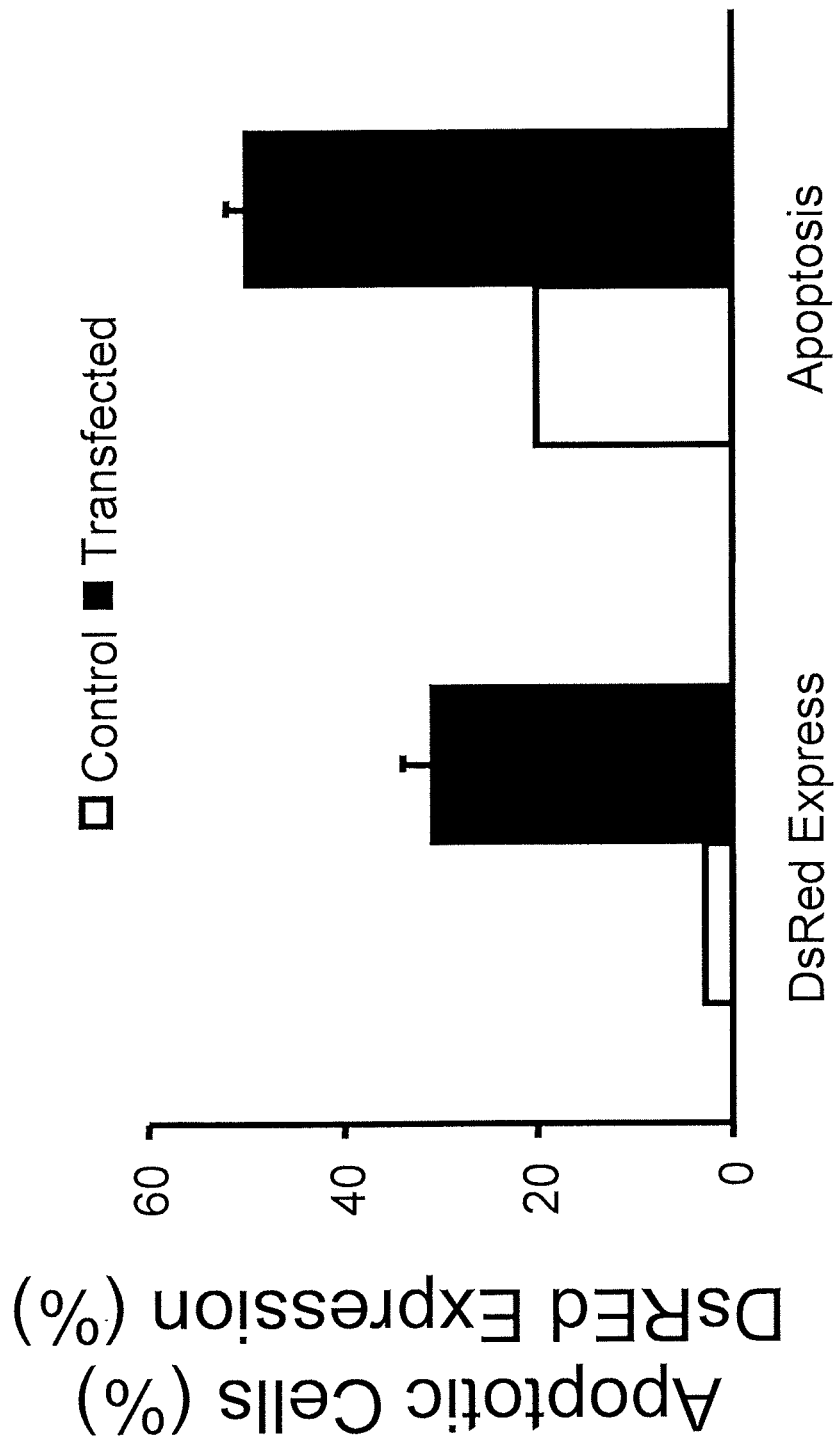
FIGS. 10A-10B. DNA uptake resulted in enhanced apoptosis in resting PBL. Resting PBL was transfected with 200 ug/ml of plasmid DNA encoding for DsRed under CMV promoter and analyzed 1d post transfection. The transfected cells were labeled with apoptosis indicator FITC-VAD-FMK (Promega, Madison, Wis.) following the product instruction. Apoptosis and transgene expression of the transfected cells were analyzed by FACS (FIG. 10A). The transfected cells without EP, DNA or caspase inhibitor (Enzyme System Product, Livermore, Calif.) (-E−D−I), with EP but without DNA or caspase inhibitor (+E−D−I), with EP and caspase inhibitor but without DNA (+E−D+I), with EP and DNA but without caspase inhibitor (+E+D−I), and with EP, DNA and caspase inhibitor (+E+D+I) were analyzed with Cell Death Detection ELISAPLUS kit (Roche, Indianapolis, Ind.) (FIG. 10B). Caspase inhibitor could only slow the cell death of the DNA-transfected resting PBL, not stop it (data not shown).
Figure 10B:
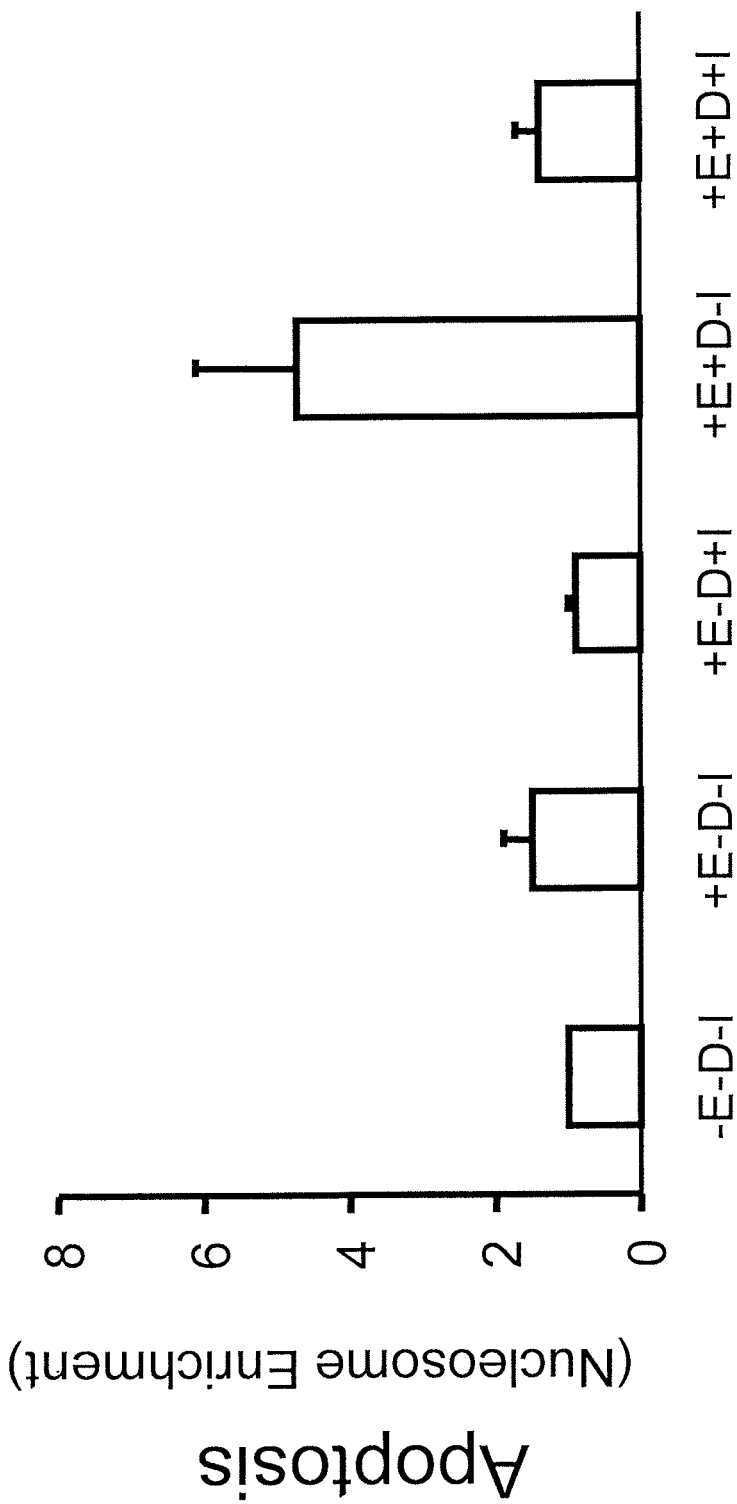

DNA uptake also resulted in enhanced apoptosis in resting PBLs. Resting PBLs were transfected with 200 ug/ml of plasmid DNA encoding for DsRed under the control of a CMV promoter and analyzed 1 day post transfection. The transfected cells were labeled with apoptosis indicator FITC-VAD-FMK (Promega, Madison, Wis.) following the product instructions. Apoptosis and transgene expression of the transfected cells were analyzed by FACS (FIG. 10A). The percentage of apoptotic cells was more than twice as high in the transfected cells as compared to control cells (FIG. 10A). The transfected cells without electroporation, DNA or caspase inhibitor (Enzyme System Product, Livermore, Calif.) (-E-D-I), with electroporation but without DNA or caspase inhibitor (+E-D-I), with electroporation and caspase inhibitor but without DNA (+E-D+I), with electroporation and DNA but without caspase inhibitor (+E+D-I), and with electroporation, DNA and caspase inhibitor (+E+D+I) were analyzed with Cell Death Detection ELISAPLUS kit (Roche, Indianapolis, Ind.) (FIG. 10B). Caspase inhibitor could only slow the cell death of the DNA-transfected resting PBL, not stop it.

EXAMPLE 8

Figure 11A:
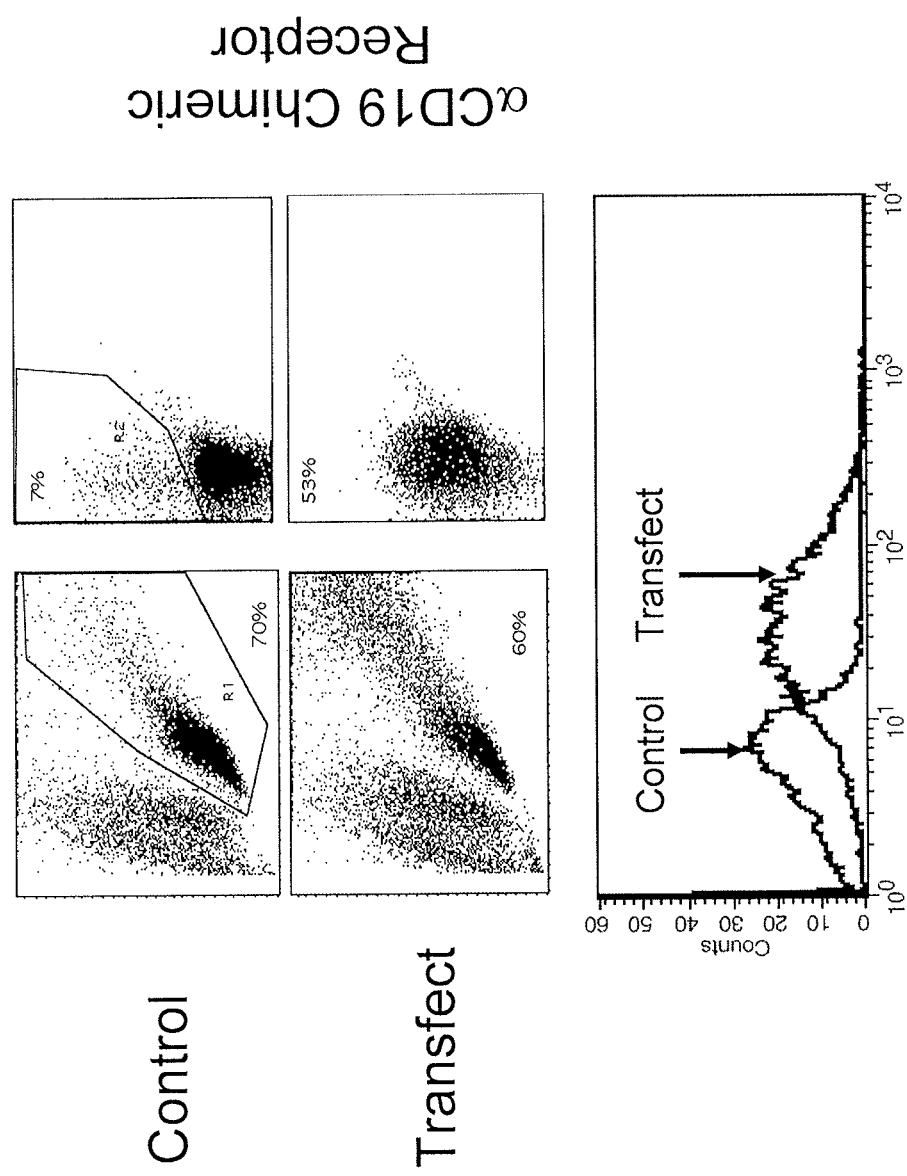
FIG. 11A-11E. αCD19 chimeric expression in resting PBMC (FIG. 11A), resting NK cells (FIG. 11B), resting PBL (FIG. 11C), resting PBMC from CLL patient (FIG. 11D), resting T cells from CLL cells (FIG. 11E). −E or +E denotes the samples with or without transfection. −CD19 or +CD19 represents the samples with or without addition of $5 \times 10^4$/ml (about 3% of the total cells in culture) autologous CD19+ CLL cells. 100 IU/ml hIL-2 was added in the cell culture.
Figure 11B:
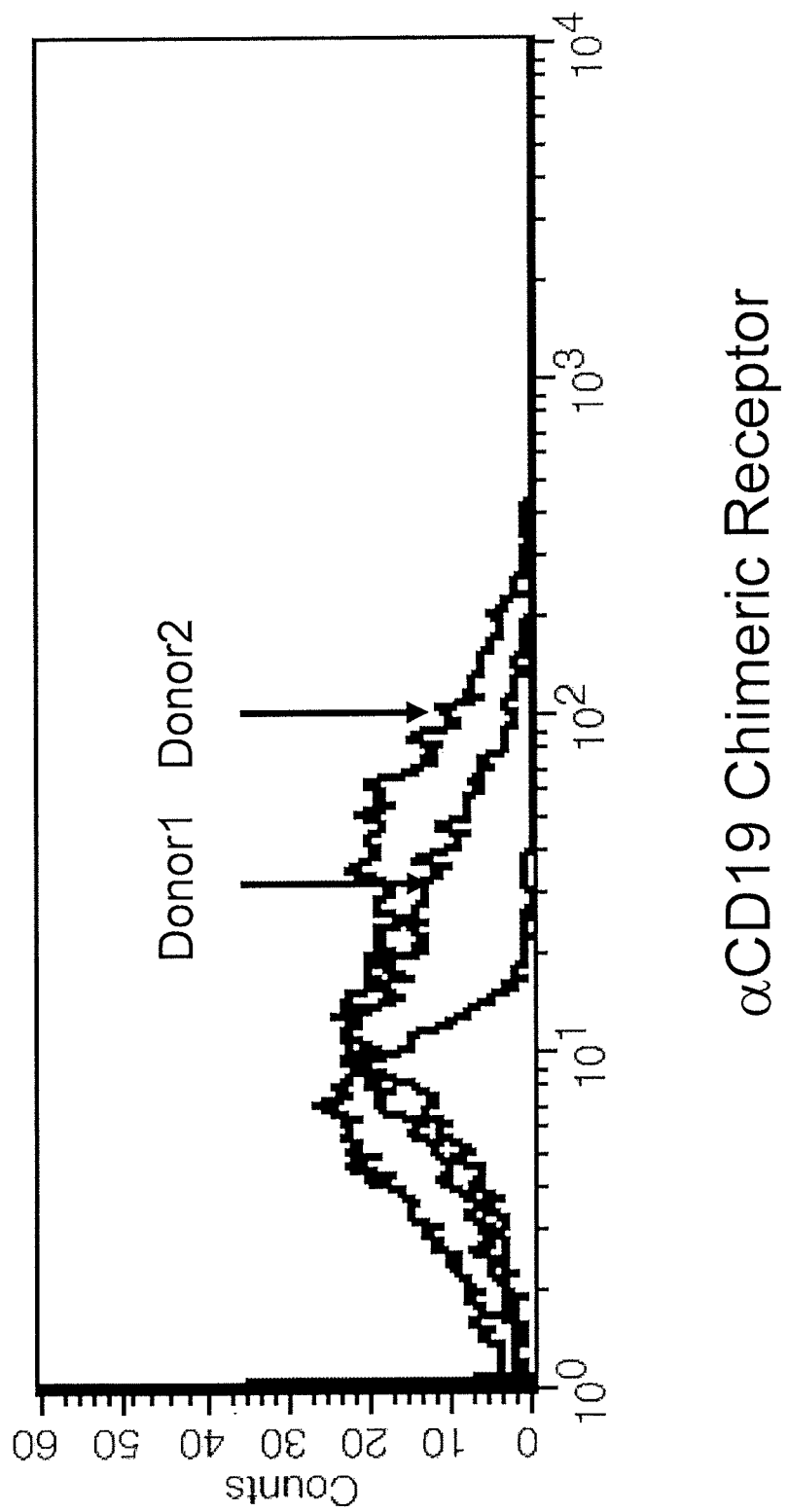
Figure 11C:
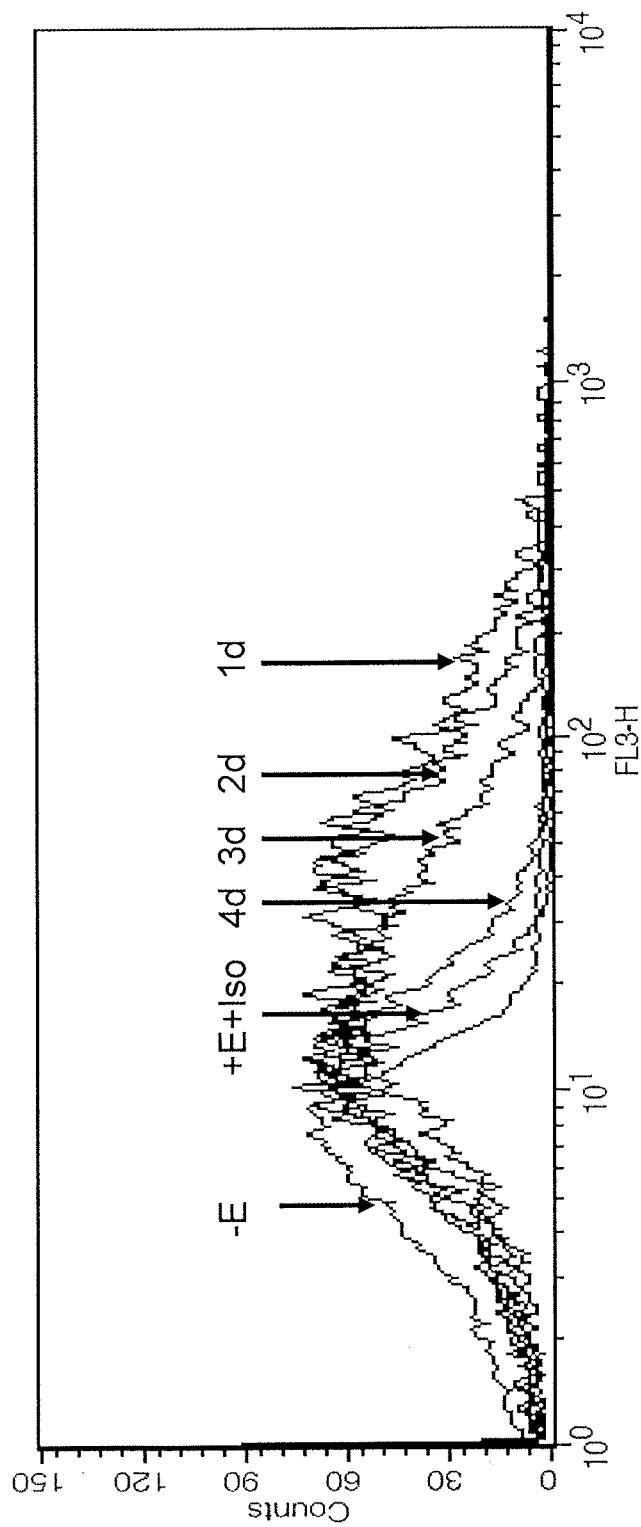
Figure 11D:
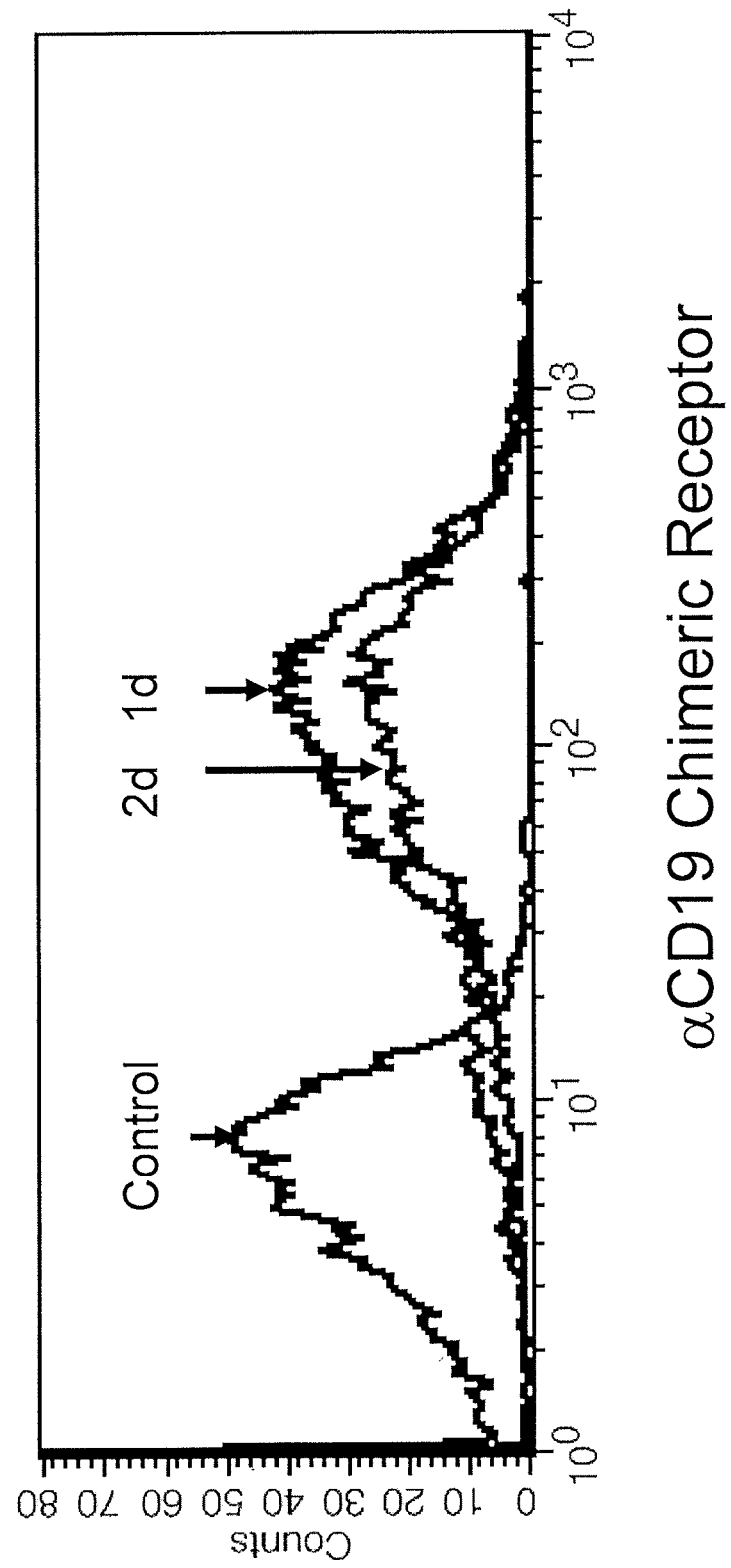
Figure 11E:
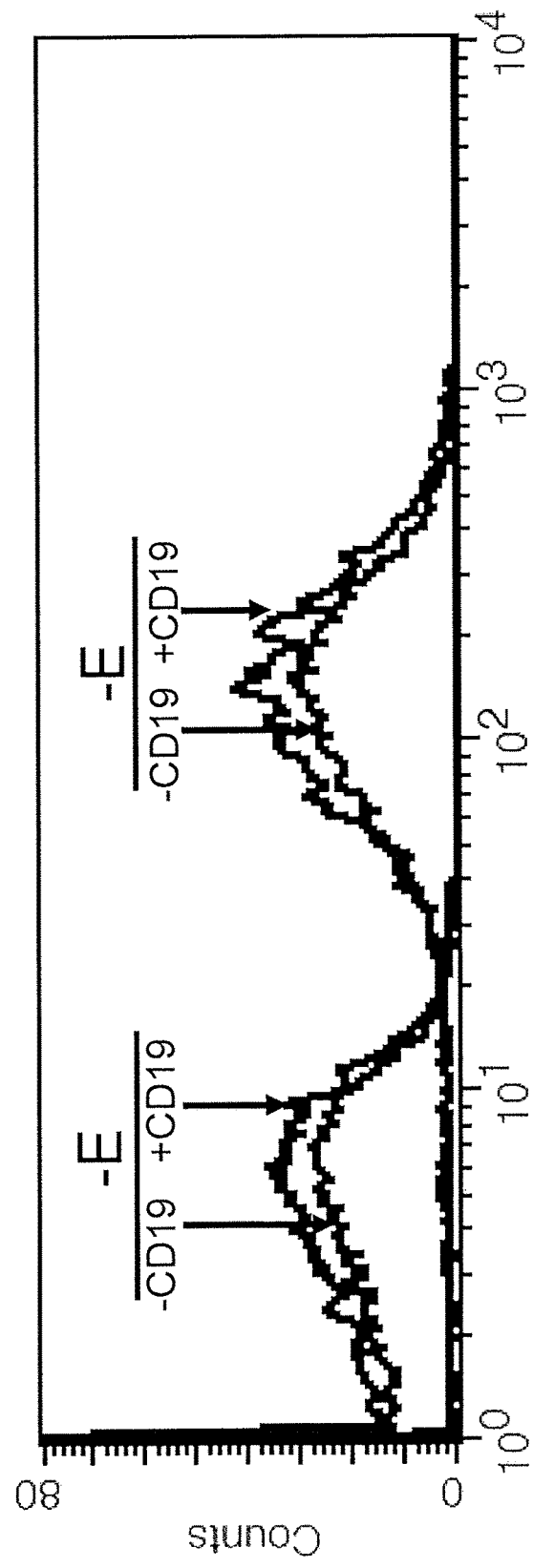
Figure 12A:
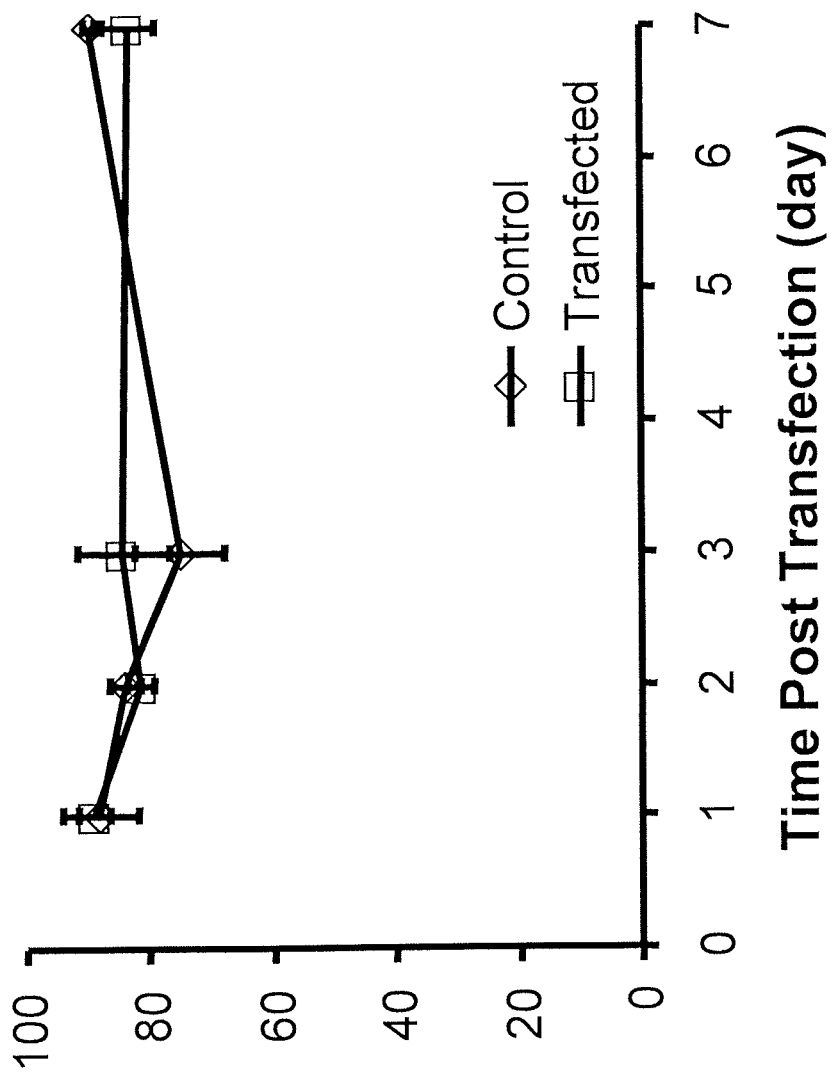
FIG. 12A-12D. Characteristics of transfected resting PBL with αCD19 chimeric receptor.
Figure 12B:
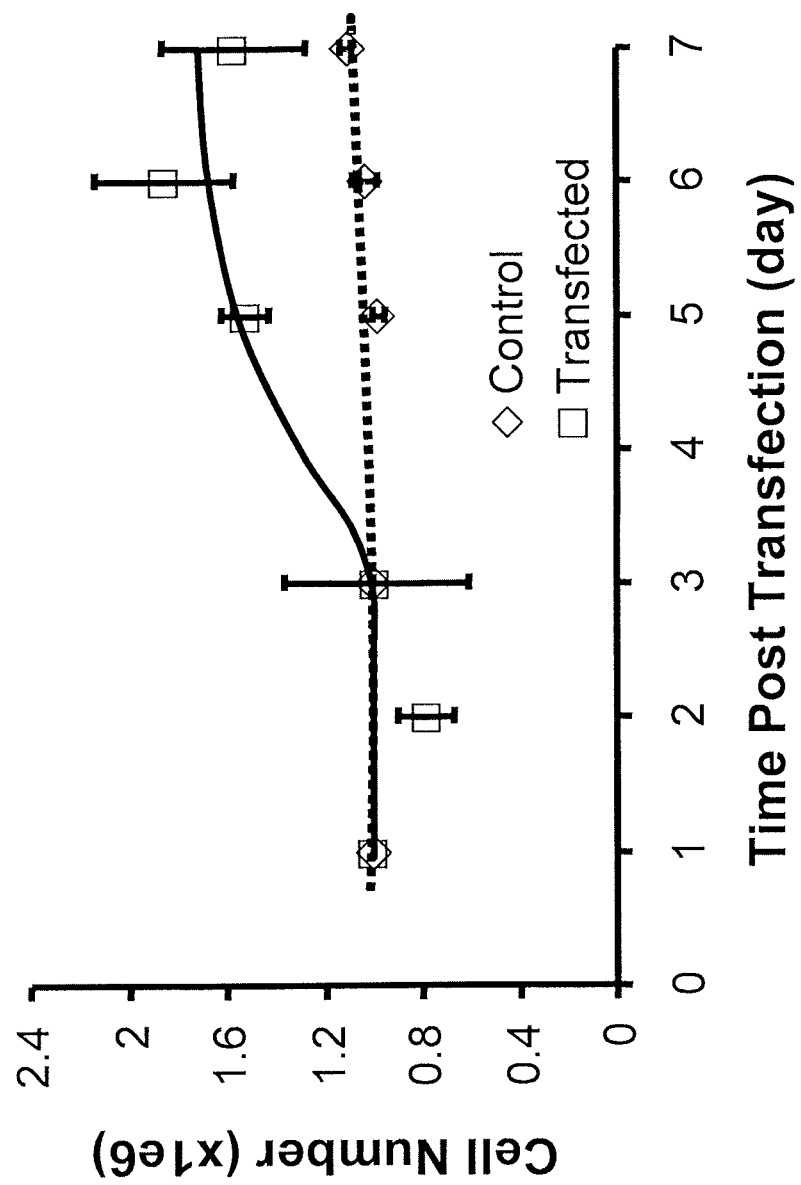
Figure 12C:
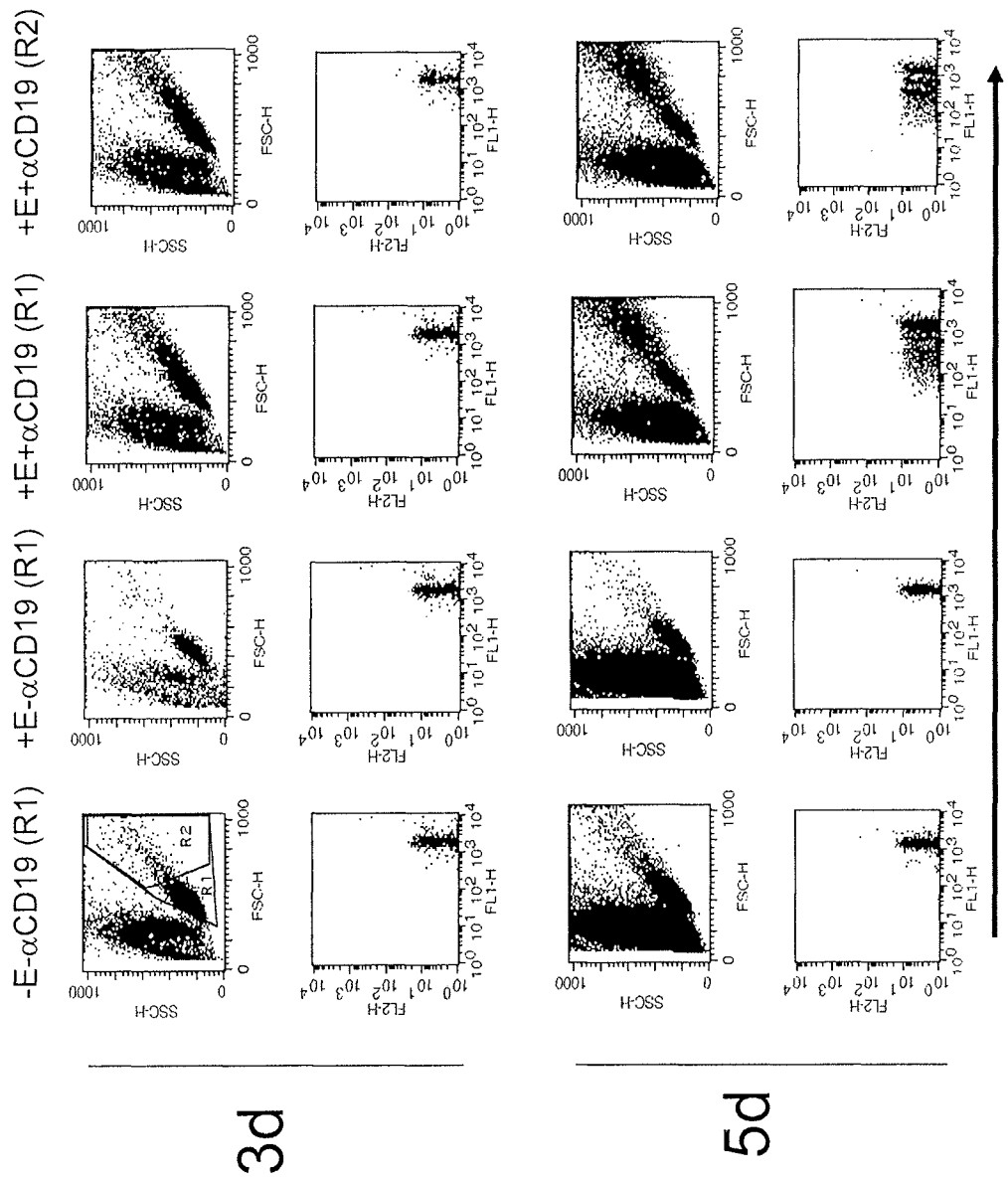
Figure 12D:
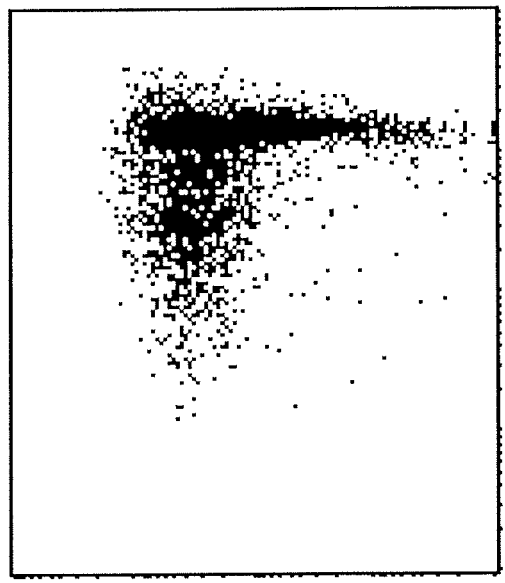
Figure 12D:

Chimeric Receptor Expression in Resting PBMCs, NK Cells, PBLs from Healthy Donors and Resting PBMC and CD3+ T Cells from CLL Patient αCD19 chimeric expression was evaluated in resting PBMCs (FIG. 11A), resting NK cells (FIG. 11B), resting PBLs (FIG. 11C) from healthy donors and resting PBMC (FIG. 11D) and CD3+ cells (FIG. 11E) from CLL patient. FIG. 12A shows high viability of PBLs transfected with an mRNA encoding a αCD19 chimeric receptor for at least 7 days post transfection. FIG. 12B shows dependence of viable cell recovery on time post transfection. FIG. 12C shows expansion of transfected PBL analyzed with CFSE. FIG. 12D shows expansion of CD3+ cells analyzed with CFSE.

EXAMPLE 9

Figure 13A:
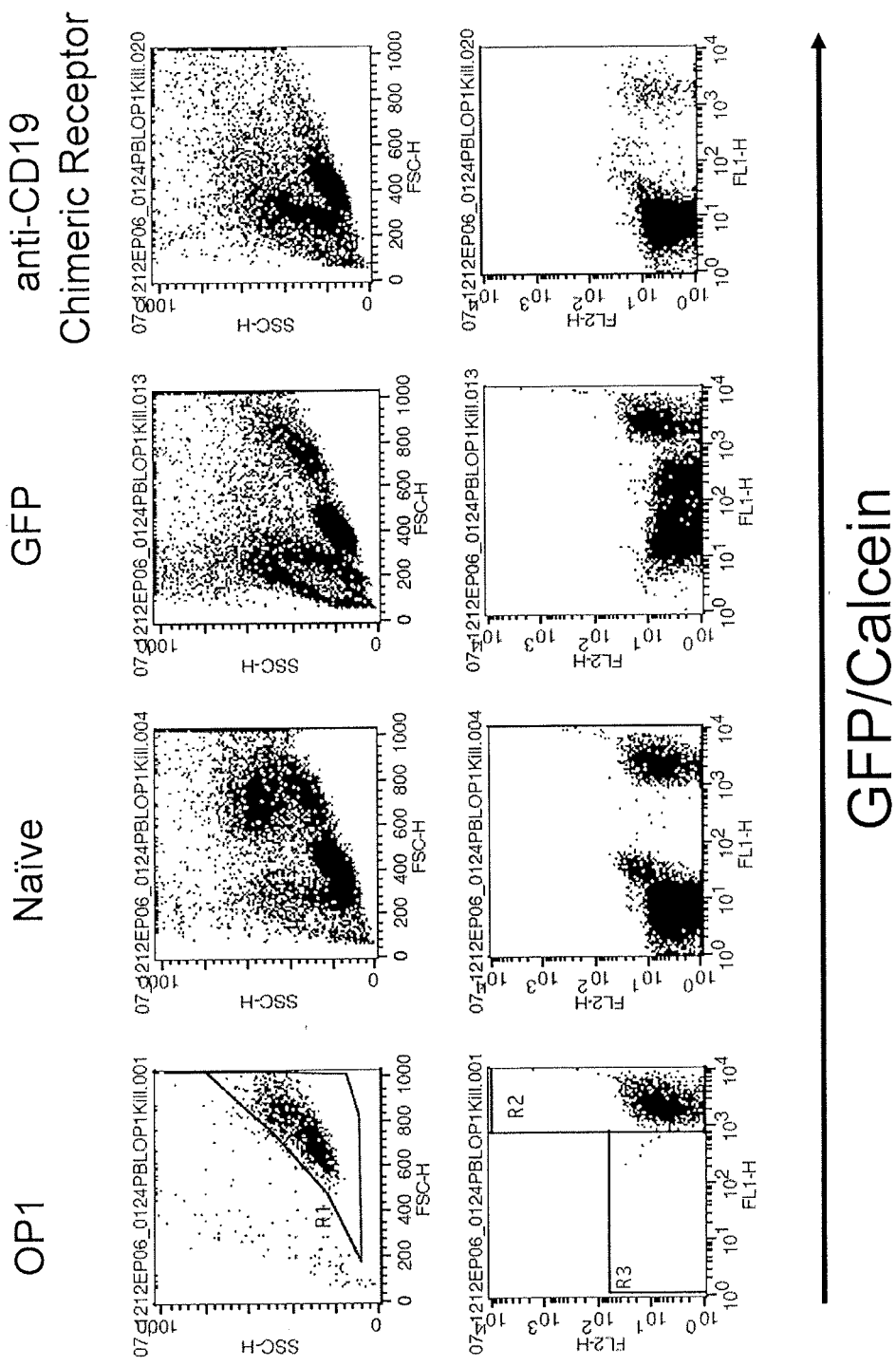
FIG. 13A-13D. Specificity of allogeneic target cell/cell line killing by αCD19 chimeric receptor-transfected resting PBL.
Figure 13B:
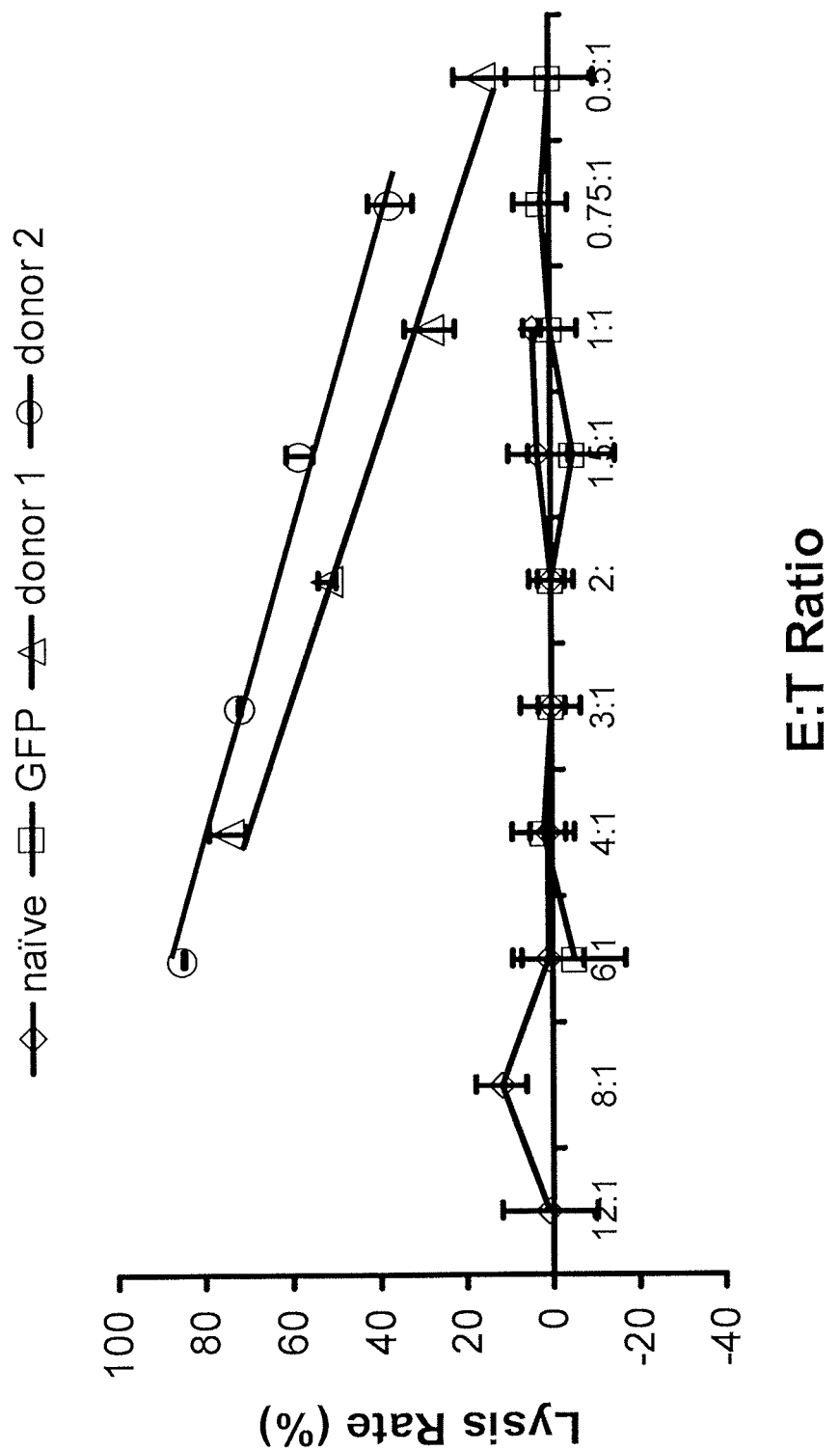
Figure 13C:
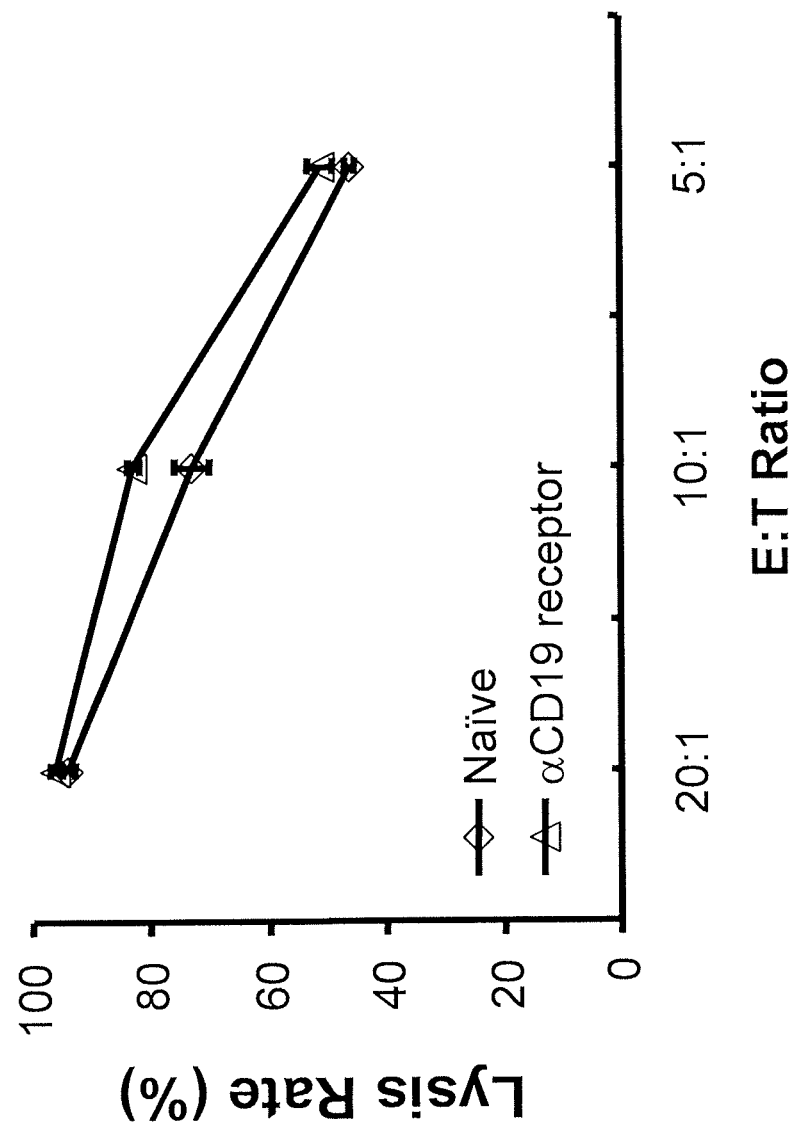
Figure 13D:
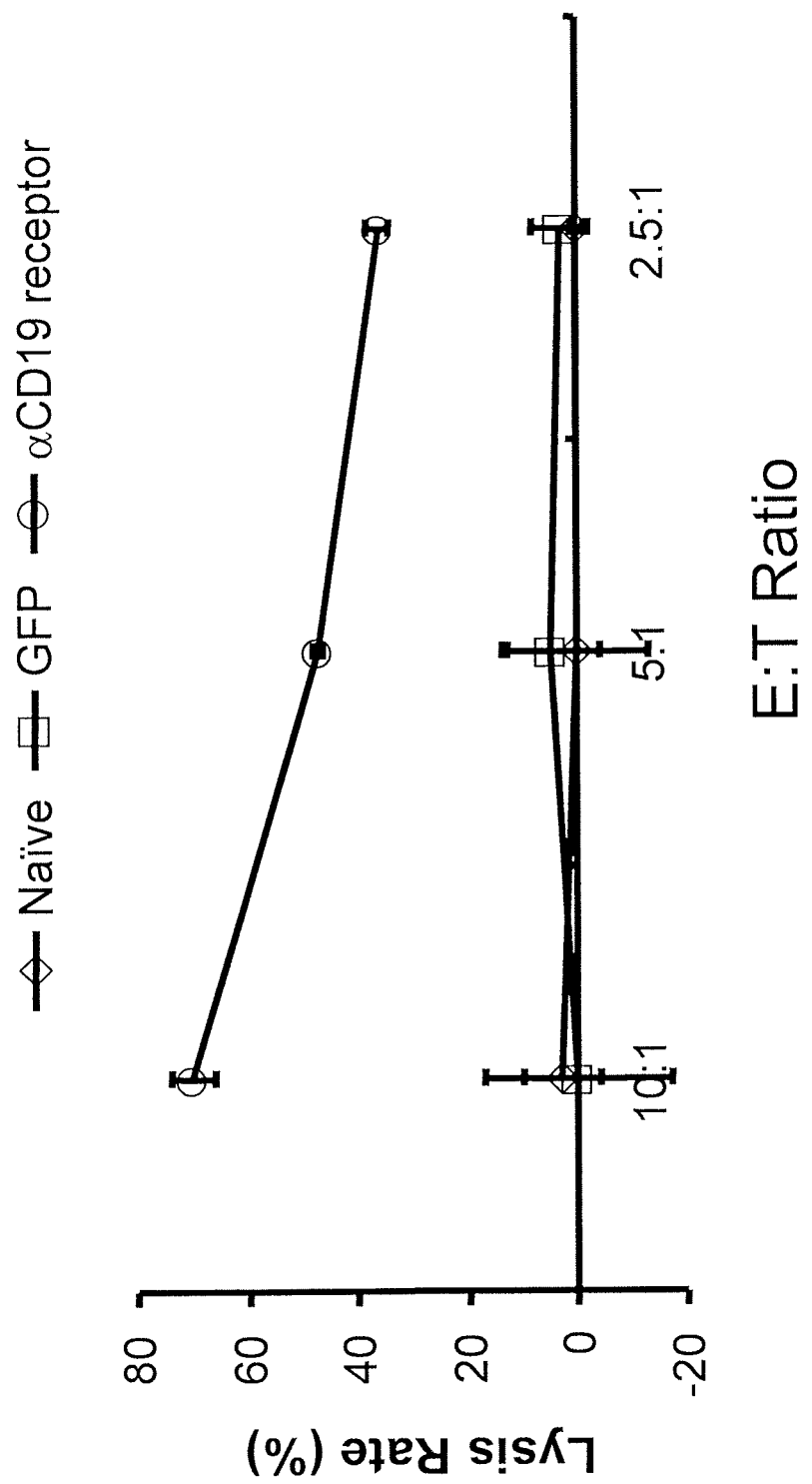

Specificity of Allogenic Target Cell/Cell Line Killing by αCD19 Chimeric Receptor Transfected Resting PBLs In this study, the specificity of allogeneic target cell/cell line killing by αCD19 chimeric receptor transfected resting PBLs was evaluated. FIG. 13A shows typical FACS analysis result of OP-1 cell line killing. FIG. 13B shows specific OP-1 killing by 2 donors of transfected PBLs, whereas naïve or GFP-transfected PBLs did not specifically kill OP-1 cells. FIG. 13C shows non-specific K562 cell killing by transfected PBLs. FIG. 13D shows specific CLL cell killing.

EXAMPLE 10

Figure 14A:
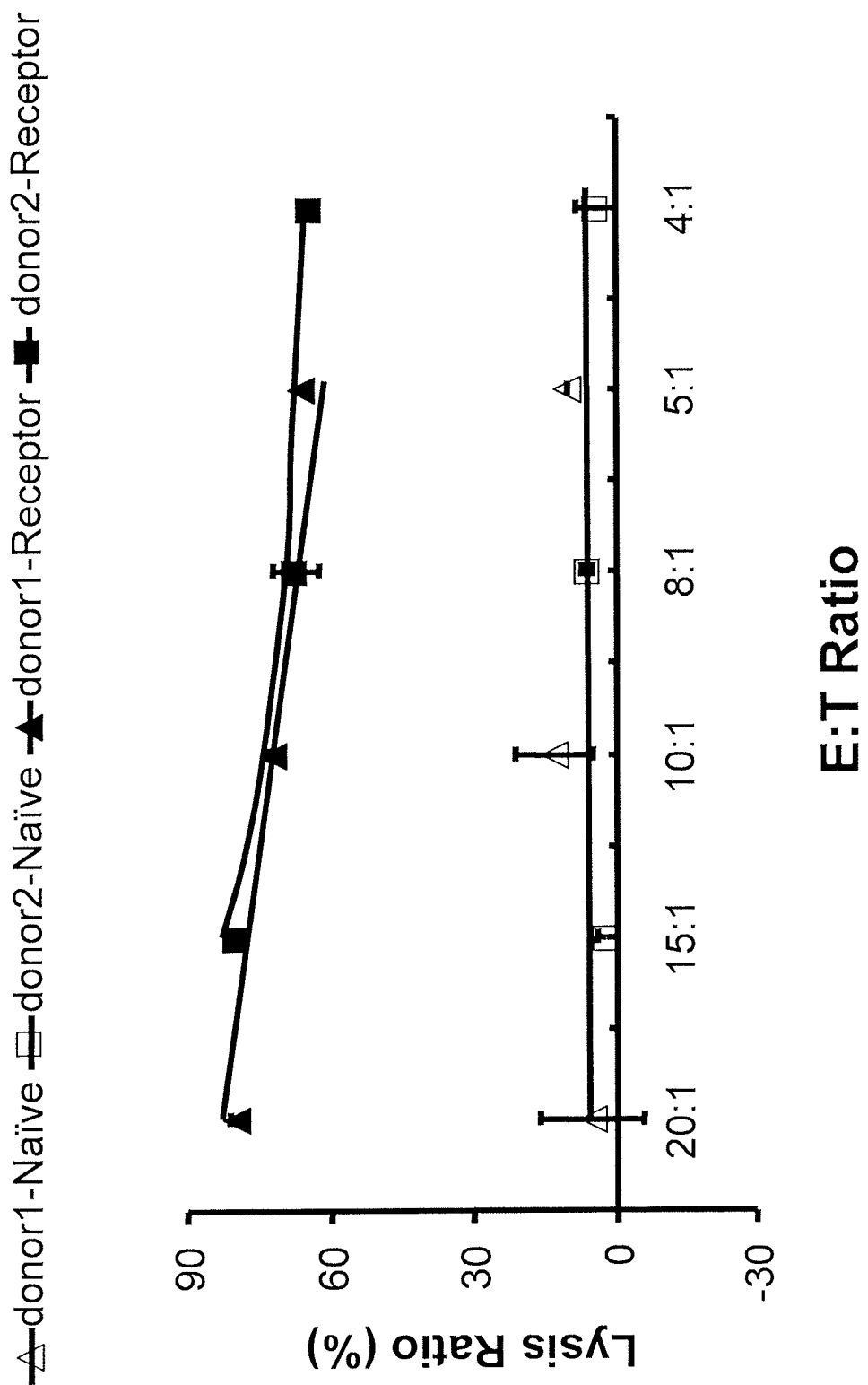
FIG. 14A-14E. Specific autologous B (FIG. 14A-C) or purified-CD19+ CLL (FIGS. 14D and E) cell killing by Resting NK cells (1 d post transfection) (FIG. 14A); resting PBMC (3 d post transfection) (FIG. 14B); Resting PBL (FIG. 14C, 1 d post transfection); resting PBMC from CLL patient (FIG. 14D, 2 d post transfection) and resting CD3+ cells from CLL patient (FIG. 14E, 3 d post transfection) after transfection with αCD19 chimeric receptor.
Figure 14B:
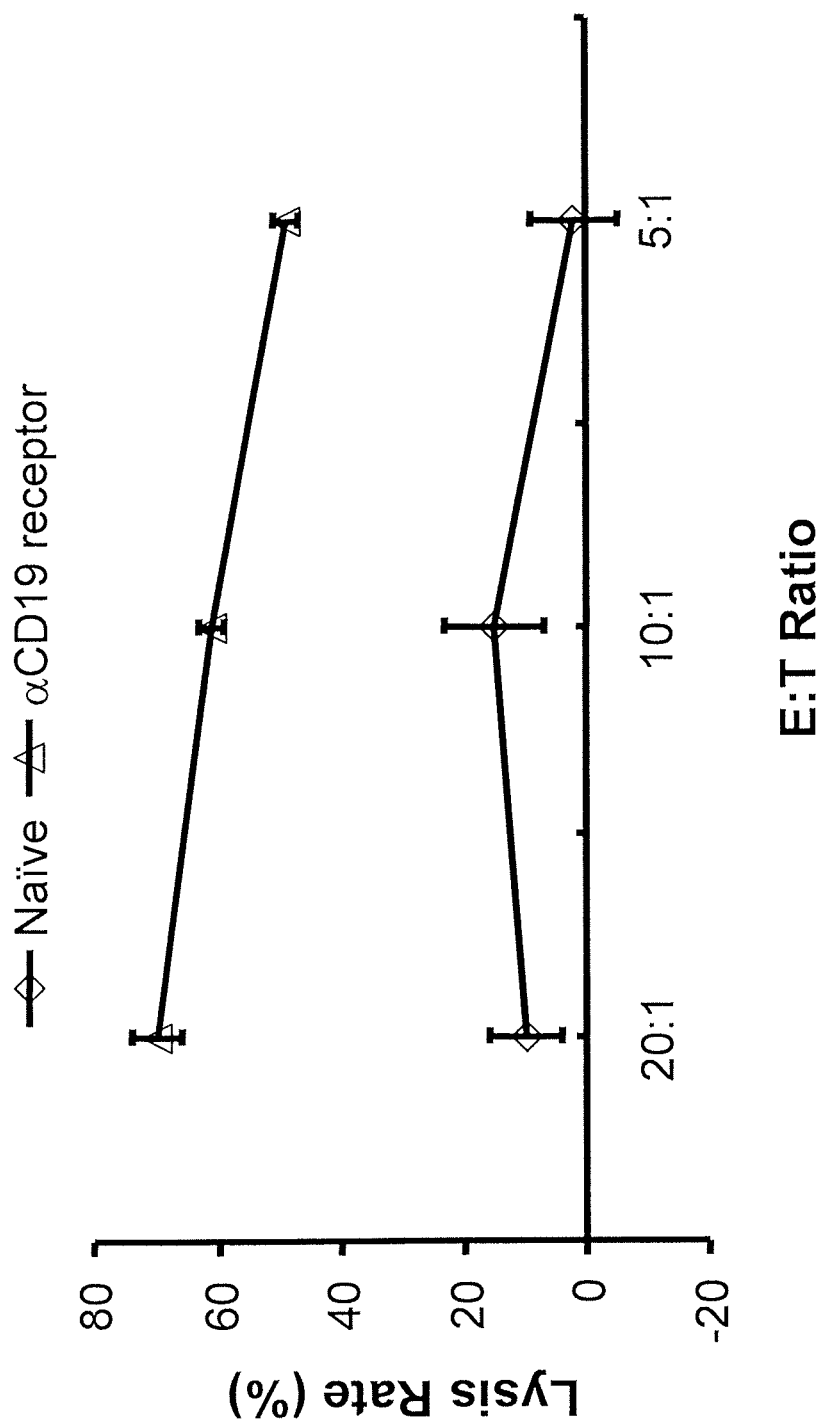
Figure 14C:
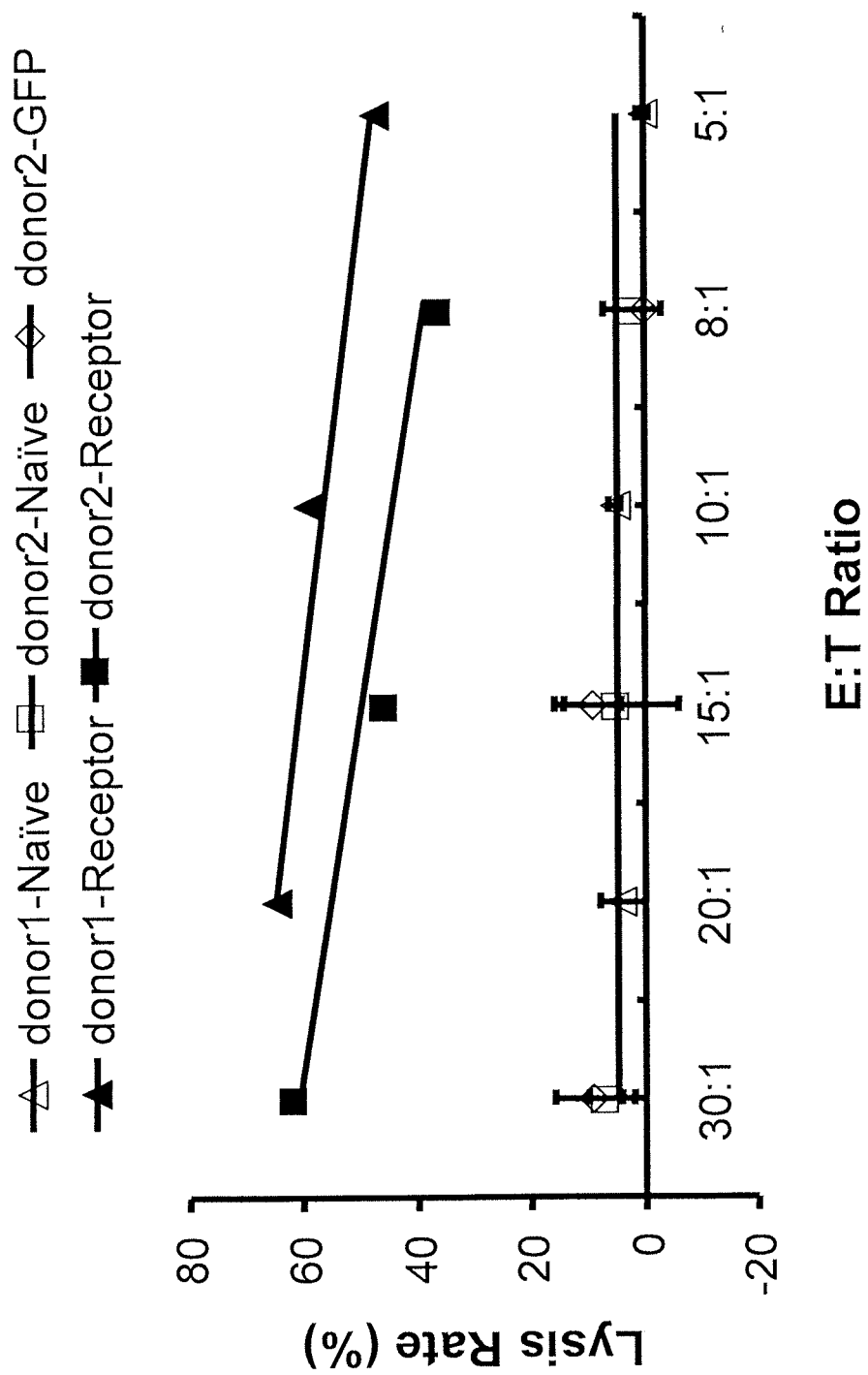
Figure 14D:
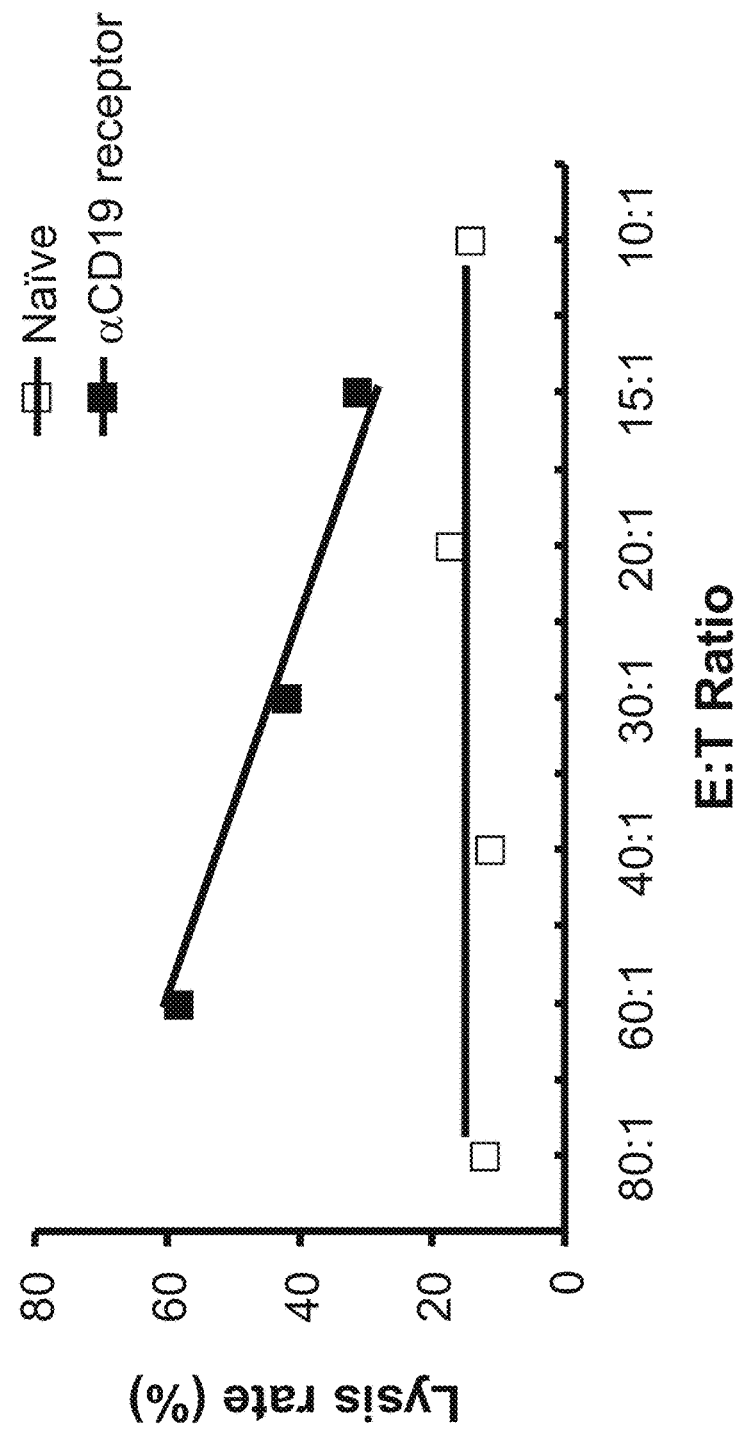
Figure 14E:
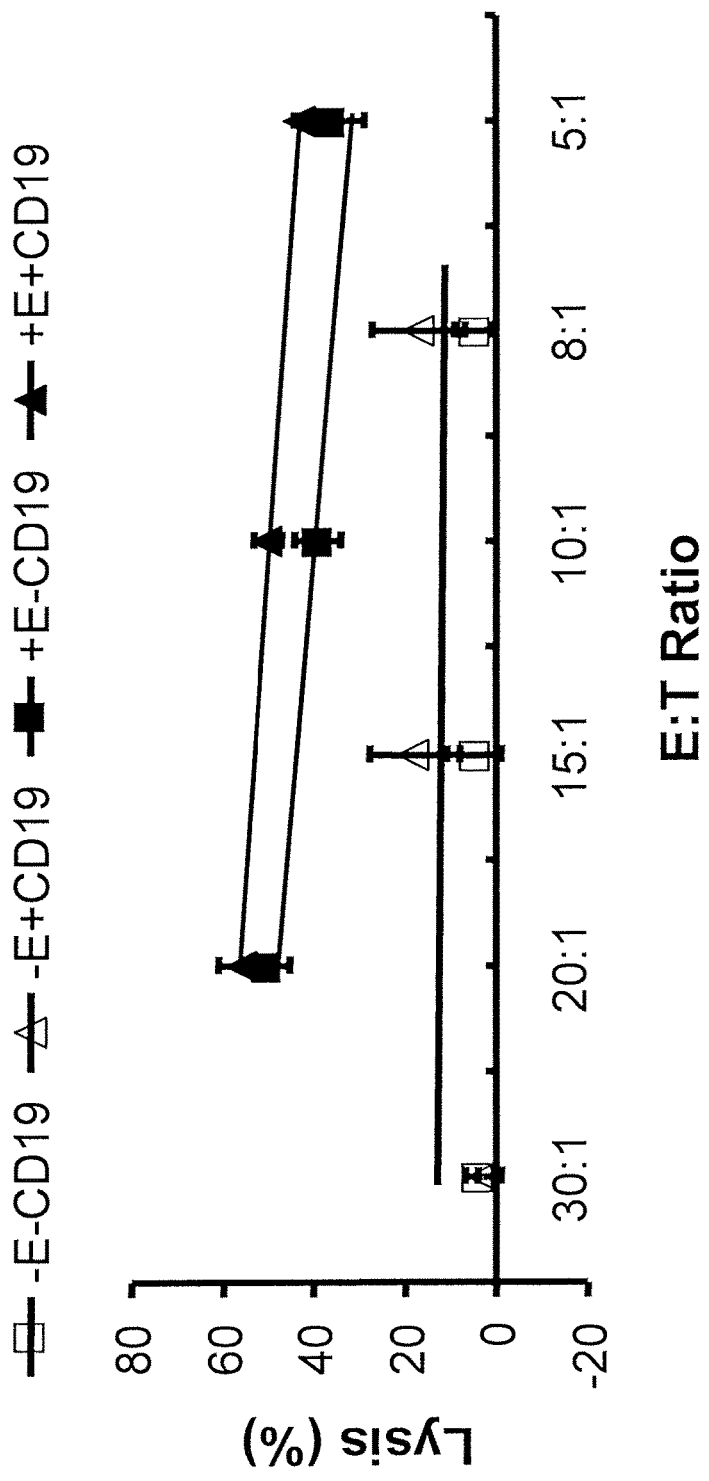
Figure 15A:
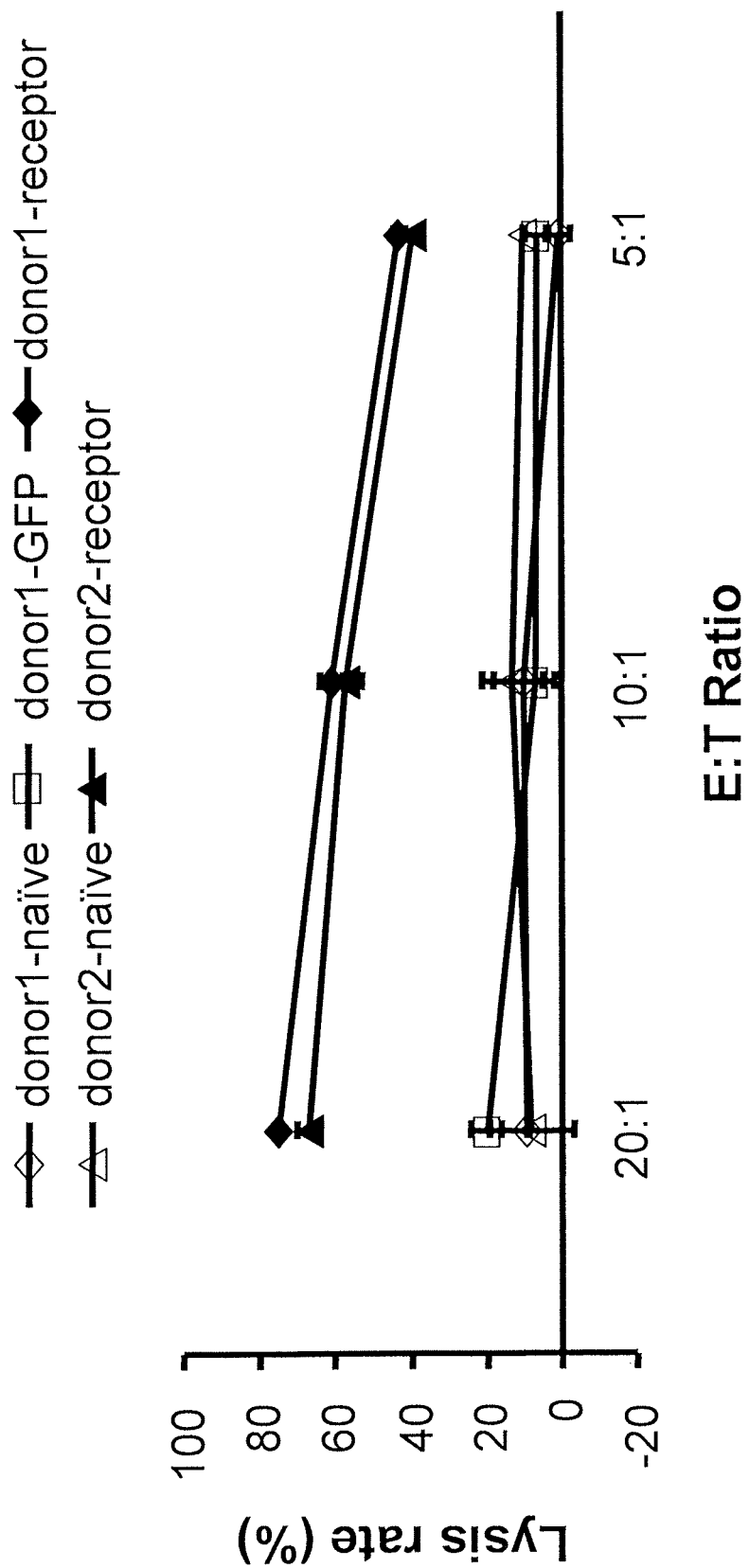
FIG. 15A-15D. Duration of specific killing of autologous B cells by transfected resting PBL with αCD19 chimeric receptor. The four-hour killing assay was performed at 1 d post transfection (FIG. 15A), 2 d post transfection (FIG. 15B), 3 d post transfection (FIG. 15C), and 7 d post transfection (FIG. 15D).
Figure 15B:
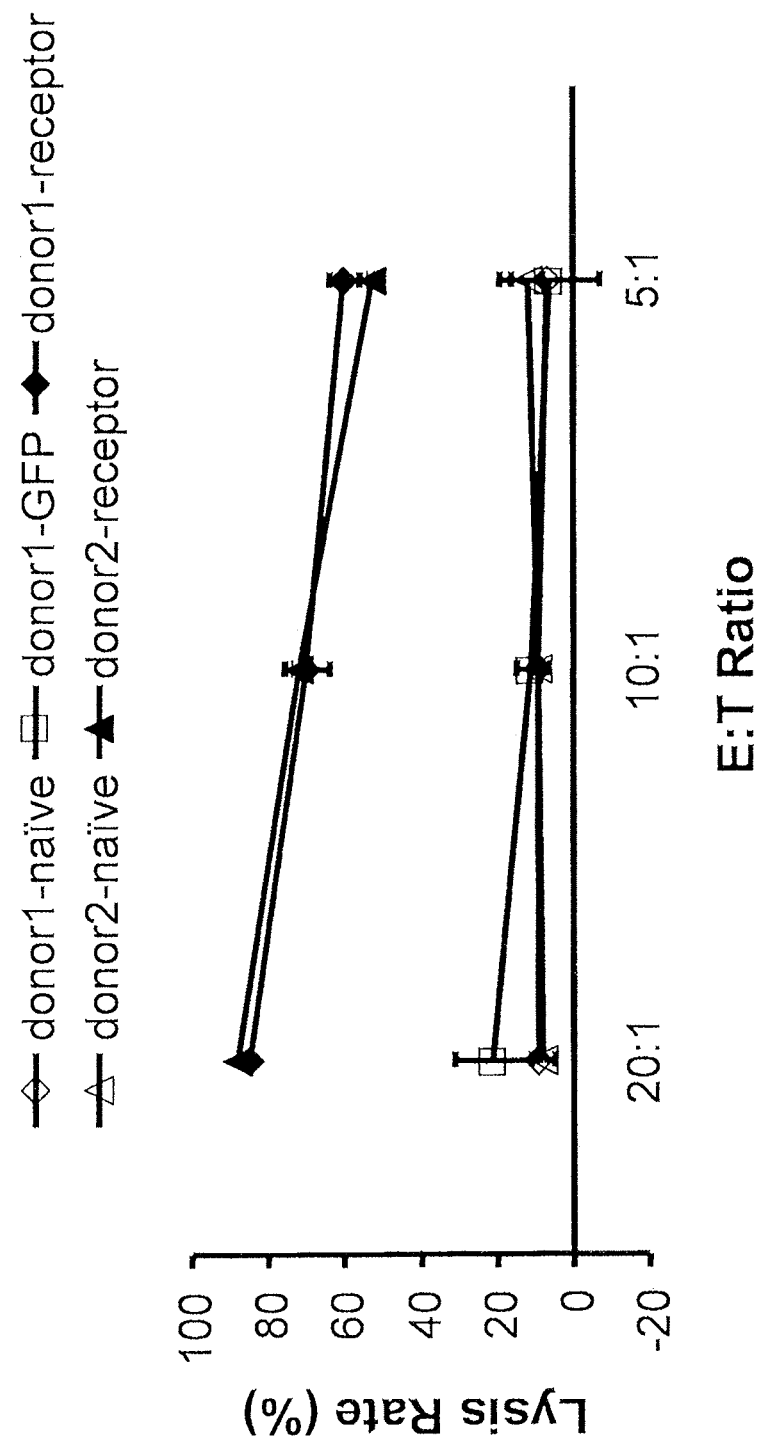
Figure 15C:
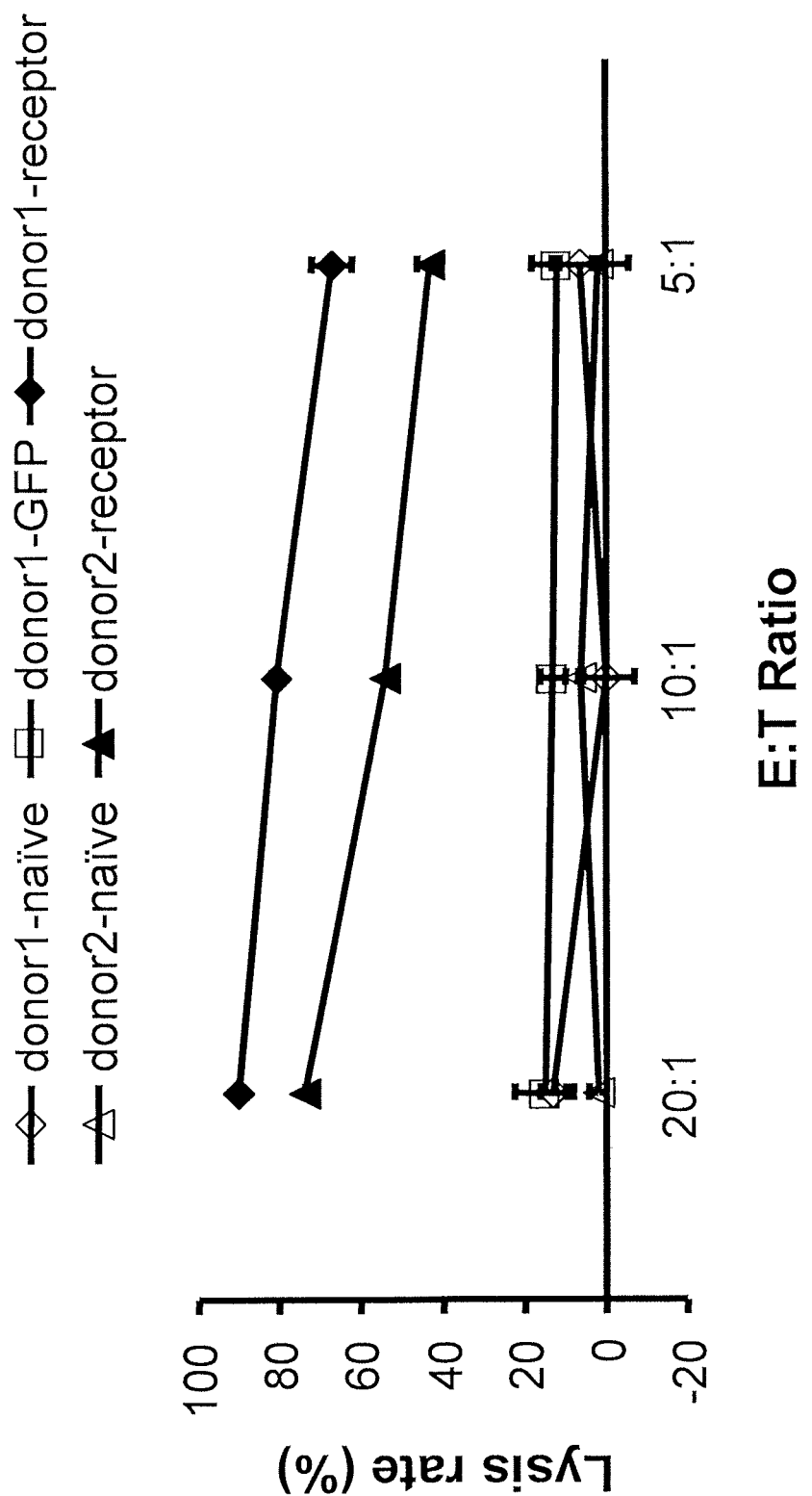
Figure 15D:
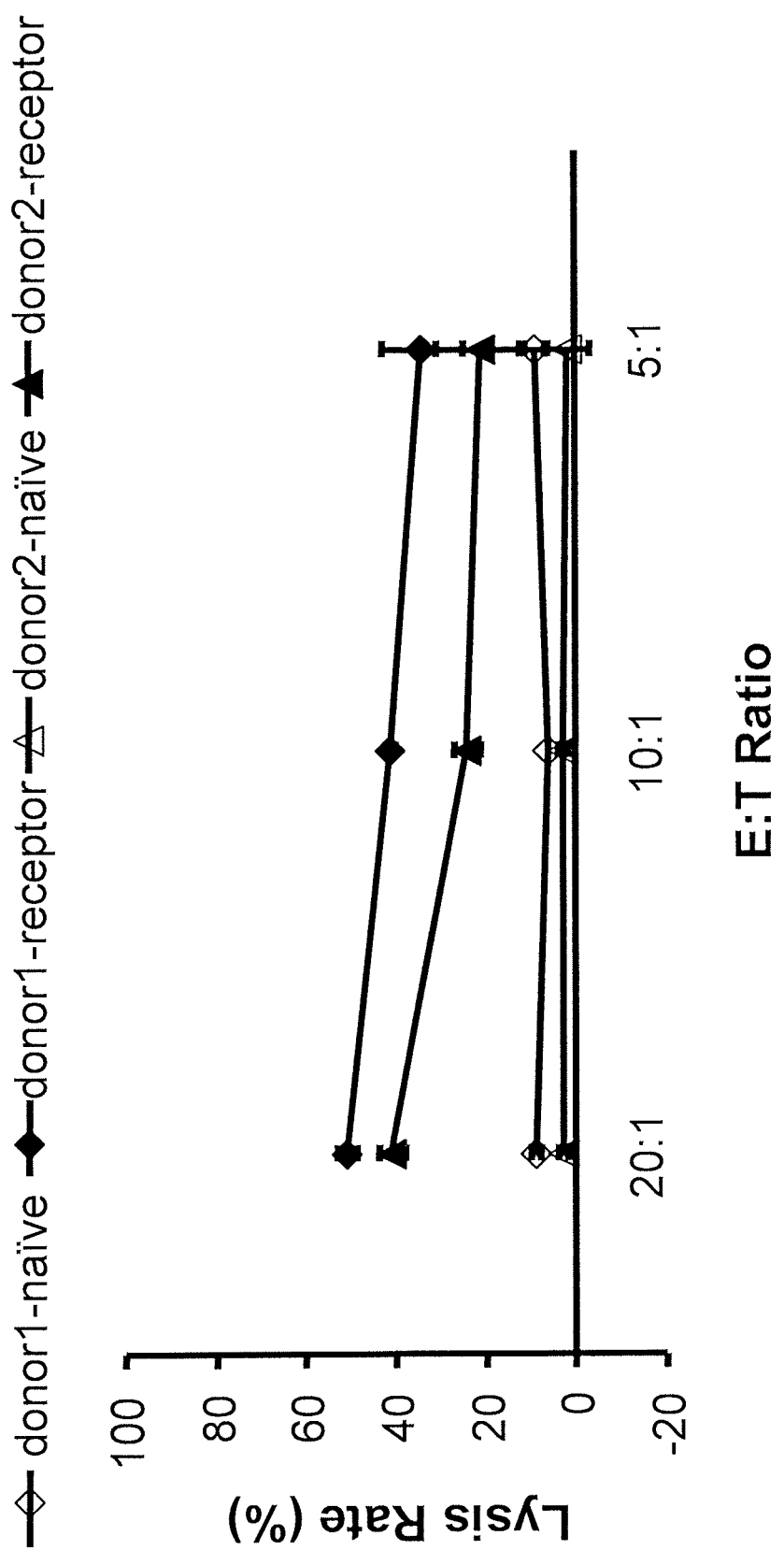

Specificity of Autologous B or Purified CD19+ CLL Cell Killing by αCD19 Chimeric Receptor Transfected Resting NK Cells, Resting PBMCs, Resting PBLs from Healthy Donors and Resting PBMC and CD3+ Cells from CLL Patient FIGS. 14A-14D show specific autologous B or purified CD19+ CLL cell killing by resting NK cells (1 d post transfection) (FIG. 14A); resting PBMCs (3d post transfection) (FIG. 14B); resting PBLs (1 d post transfection) (FIG. 14C); resting PBMC from CLL patient (FIG. 14D) and resting CD3+ T cells from CLL patient (FIG. 14E) after transfection with αCD19 chimeric receptor. FIGS. 15A-15D show the duration of specific killing of autologous B cells by transfected resting PBLs with αCD19 chimeric receptor. The four-hour killing assay was performed at 1 day post transfection (FIG. 15A), 2 days post transfection (FIG. 15B), 3 days post transfection (FIG. 15C), and 7 days post transfection (FIG. 15D).

Materials and Methods

Cells. The CD19+ human B-lineage ALL cell line, OP-1 (developed at St. Jude Children's Research Hospital), and the genetically engineered myeloid leukemia cell line, K562, co-expressing 4 1BB ligand and membrane bound IL-15 (K562-4-15), also developed at St. Jude Children's Research Hospital, were maintained in RPMI-1640 supplemented with 10% fetal bovine serum and antibiotics. Primary leukemic cells from two patients with B-CLL were obtained by directly collecting the cells in the interfacial layer after Ficoll plaque density gradient centrifugation, frozen after two rounds of PBS wash until use. Primary peripheral blood mononuclear cells (PBMC) from healthy donors were prepared from leukapheresis product purchased from BRT Laboratories, Inc. (Baltimore, Md.). PBMCs were obtained directly from the interfacial layer in standard Ficoll density gradient centrifugation, washed twice with phosphate buffered saline (PBS), and frozen and stored in liquid nitrogen until use. The primary cells, whenever used, were cultured in RPMI-1640 supplemented with 10% fetal bovine serum and antibiotics. CD3+ cells were obtained by negative purification using Miltenyi kit.

The resting NK cells were negatively selected by following the protocol supplied with the Miltenyi kit (Auburn, Calif.) and frozen in liquid nitrogen until use. Primary NK cells were expanded as previously described by Imai et al. Peripheral blood mononuclear cells were cultured with thawed K562 cells that express 4-1BB ligand and membrane-bound IL-15 (K562-4-15) provided by St. Jude Children's Research Hospital and which were irradiated with 10,000 to 20,000 rad prior to culturing with NK cells. Culturing of the NK cells with the target cells to allow for NK cell killing was performed in the presence of 10 IU/ml-100 U/ml IL-2, 10% FBS and antibiotics.

PBMCs were prepared by incubating the thawed PBMCs in a centrifuge tube for 30 minutes after thawing and collecting all cells by centrifugation. PBLs were prepared by culturing the thawed PBMC in tissue culture flask for 1-2 hours and only collecting the suspended cells.

Molecules for electroloading. The cloning of anti-CD19 chimeric receptor into pVAX1 (Invitrogen, Carlsbad, Calif.) vector was performed by digesting the parent plasmid pMSCVanti-CD19BBZ encoding a single chain antibody conjugated with the 4-1 BB intercellular domain and the CD3 domain (generated at St. Jude Children's Research Hospital) and the pVAX1 vector with EcoR I and Xho I and ligated using T4 DNA ligase. mRNA encoding for anti-CD19 chimeric receptor was in vitro transcribed with T7 polymerase using an Ambion mMESSAGE mMACHINE T7 Ultra kit (Ambion, Austin, Tex.) with the cloned template of the pVAX1 vector containing anti-CD19 chimeric receptor. mRNA quality and quantity was analyzed by 1% agarose gel after 15 minutes denaturation at 70° C. in mRNA denaturation buffer (Invitrogen, Carlsbad, Calif.) and OD260/280 measurement. The plasmid DNA encoding for eGFP on the pCI (Promega, Madison, Wis.) backbone under CMV promoter was used for DNA transfection. The mRNA encoding for GFP was produced using the pCI-eGFP and the same Ambion kit as mentioned above. FITC-dextran was purchased from Sigma (St. Louis, Mo.). The FITC-conjugated control siRNA was purchased from Qiagen (Valencia, Calif.).

Transfection. The resting NK cells in frozen medium (10% DMSO in FBS) were thawed in 37° C. water bath, incubated for 0.5-1 h at 37° C. in the prewarmed fresh full medium (RPMI-1640+10 % FBS+ antibiotics) with volume of 10× that of frozen medium and ready for transfection. The expanded NK cells were harvested at the indicated time points for transfection. Before transfection, the expanded NK cells were washed with MXCT EP buffer once. The unstimulated resting cells were washed 2× in PBS containing 0.5% FBS and 2 mM EDTA and 3× in MXCT EP buffer containing additionally 0.1% BSA. After washing, expanded NK and resting NK, PBL, PBMC. T, and CD8+ cells were suspended in MXCT EP buffer, mixed with molecules to be loaded/transfected, transferred into MXCT chamber, transfected with program "Expanded-NK Cell #3" and "Resting-NK#1" for expanded and resting NK cells respectively in MXCT GT system (Maxcyte, Gaithersburg, Md.), transferred into incubation tube, incubated for 20 minutes at 37° C., and returned to the culture medium. The loading or expression efficiency was analyzed by flow cytometry.

Detection of the expression of chimeric receptor and immunophenotyping. The transfected NK cells were stained with goat anti-mouse $(Fab)_2$ polyclonal antibody conjugated with biotin (Jackson immuno Research labs, West Grove, Pa.) followed by peridinin chlorophyll protein- (PerCp; Becton Dickinson, San Jose, Calif.) labeled streptavidin staining. The positive cells was gated according to the background cells with goat biotin-conjugated IgG followed by streptavidin-PerCp.

The following antibodies were used for immunophenotypic characterization of expanded and transfected NK cells: anti-CD3 conjugated with fluorescein isothiocyanate (FITC), anti-CD19 conjugated with phycoerythrin (PE), anti-CD16-PE, and anti-CD56-PE. Antibody staining was analyzed by a FACSCalibur (Becton Dickinson).

Cell Killing Assays. To facilitate the large number of cell killing studies, a cell killing assay was developed based on acetoxmethyl-calcein (calcein-AM, Molecular Probes, Eugene, Oreg.) staining and flow cytometry. Briefly, calcein-AM pre-labeled target cells (100 µl) were co-cultured with 100 µl of either transfected, non-transfected primary NK cells or just fresh medium at various effector to target (E:T) ratios in each well of a 96-well U-bottom tissue culture plate (Costar, Cambridge, Mass.). The 96-well plate was centrifuged at 400 g for 5 minutes prior to cell culture at a 37° C., 5% $CO_2$ incubator. The cells were resuspended in the original culture media, transferred to FACS tubes for FACS analysis at indicated time points.

In some studies, cell killing assays described in Imai, et al. were followed. Briefly, plain target cells $10^5$ cells in 100 µl were co-cultured with 100 µl of either transfected, non-transfected primary NK cells or just fresh medium at various effector to target (E:T) ratios in each well of a 96-well U-bottom tissue culture plate (Costar, Cambridge, Mass.). After 400 g×5 minutes centrifugation, the cells were cultured for desired cell-killing time. The cells were harvested and co-stained with anti-CD19-FITC and anti-CD56-PE antibodies for 20 minutes on ice. After washing in PBS, the cells were resuspended with 200 µl of PBS and analyzed by flowcytometry.

The cultures were performed in the absence of exogenous IL-2. FACS analysis was performed using a FACSCalibur with 15 second collection. The specific cell lysis rate (%) was calculated by $100 - N_{target}/N_{Control} \times 100$, where $N_{target}$ is the number of viable target cells co-cultured with NK cells and the $N_{control}$ is the number of viable target cells cultured alone.

EXAMPLE 11

CAR-Expressing PBMCs Kill HS-Sultan Cells In Vitro and In Vivo

Figure 16:
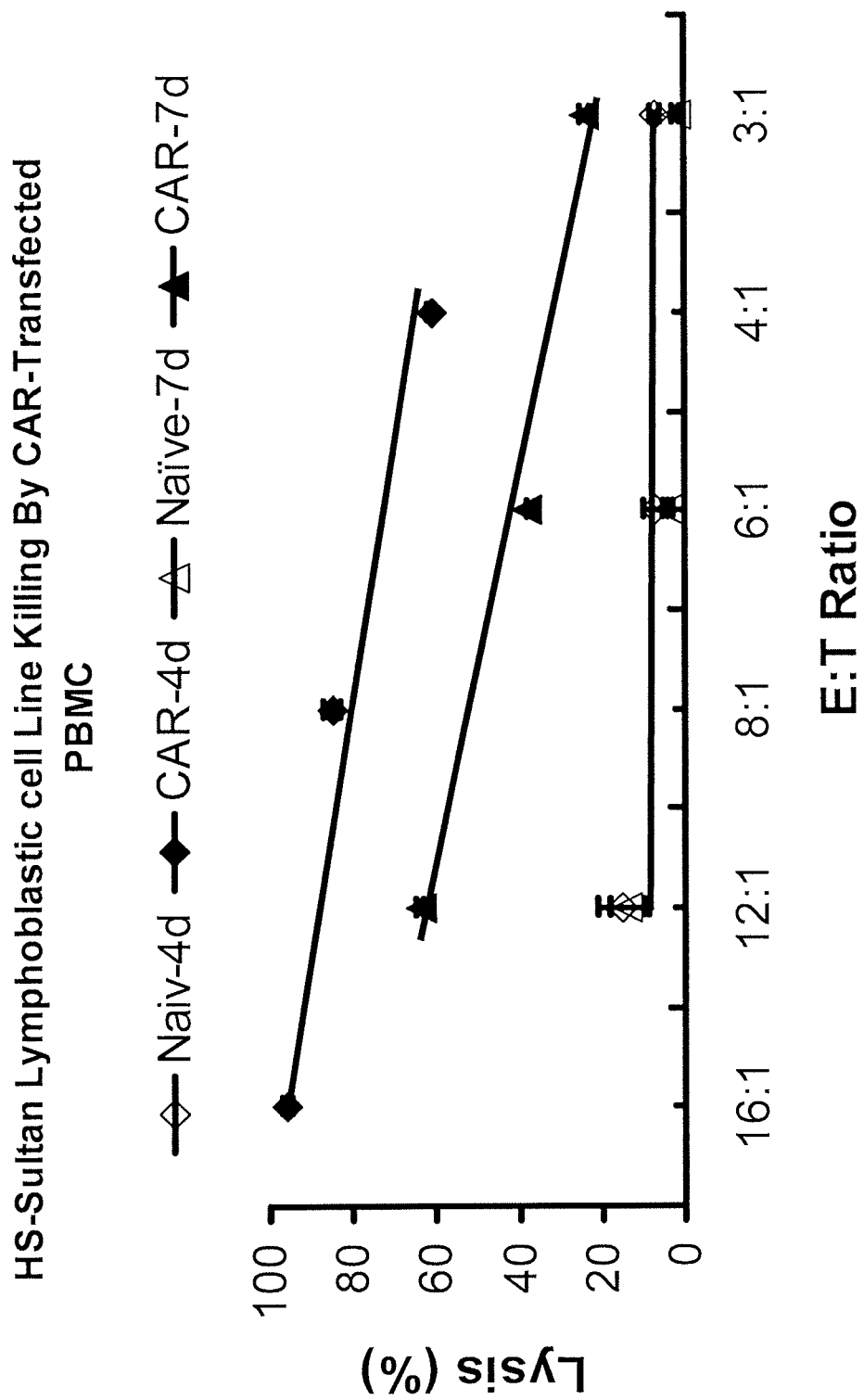
FIG. 16. HS-Sultan lymphoblastic cell killing by CAR-transfected PBMCs in vitro.

Human PBMCs were electroloaded with mRNA encoding anti-CD19-BBz. Four or seven days post transfection, PBMCs (transfected or non-transfected (Naïve)) were mixed in vitro with calceinAM-prelabeled HS-Sultan cells, a leukemia cell line that is CD19+, at various effector:target (E:T) ratios. Cell cytotoxicity was performed by FACS 4 hours after mixing. As shown in FIG. 16, the transfected PBMCs were able to kill HS-Sultan cells at 4 days and 7 days at all E:T ratios tested, with the killing being more effective at 4 days than at 7 days. In addition, increased killing was achieved with higher E:T ratios.

To demonstrate that CAR-expressing PBMCs could kill tumor cells in vivo, a HS-Sultan subcutaneous co-mixing model in Beige SCID mice was used. PBMC 1 day post-mRNA transfection (transfected or non-transfected) with mRNA encoding anti-CD19-BBz were mixed with HS-Sultan cells at different ratios and subcutaneously injected into mice (5 mice/group) as indicated in Table 1.

TABLE 1

| Study group | purpose | E:T | Sultan # | PBMC # | PBMC-CAR # | Mouse # |
|---|---|---|---|---|---|---|
| 1 | control | 0 | 1e6 | 0 | 0 | 5 |
| 2 | control | 20:1 | 1e6 | 2e7 | 0 | 5 |
| 3 | treatment | 20:1 | 1e6 | 0 | 2e7 | 5 |
| 4 | | 6.7:1 | 1e6 | 0 | 6.7e6 | 5 |
| 5 | | 2.3:1 | 1e6 | 0 | 2.3e6 | 5 |
| 6 | | 0.7:1 | 1e6 | 0 | 0.7e6 | 5 |

Figure 17:
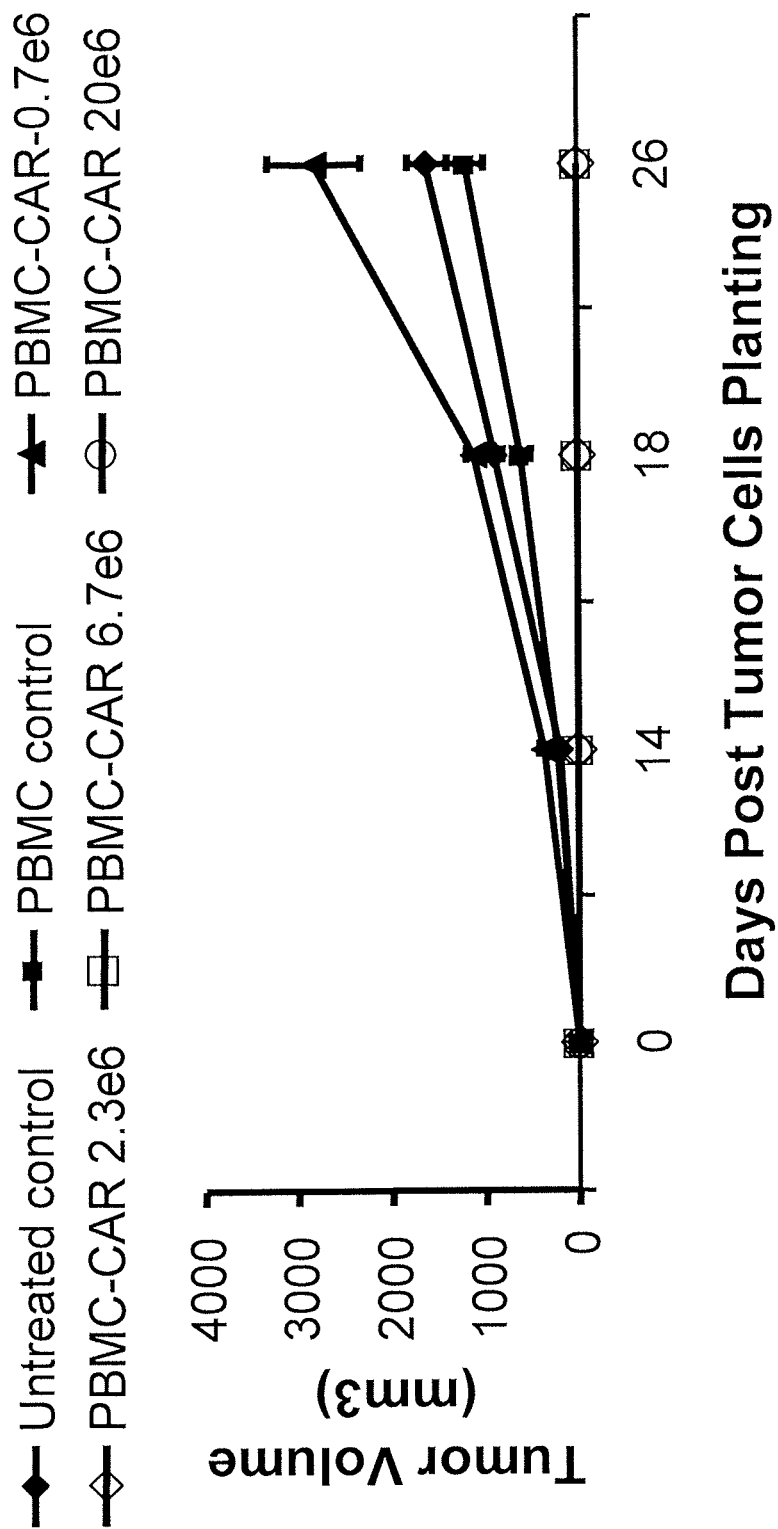
FIG. 17. HS-Sultan lymphoblastic cell killing by CAR-transfected PBMCs in vivo. HS-Sultan cells (1e6 cells) mixed with CAR-transfected PBMCs (0.7e6, 2.3e6, 6.7e6 and 20e6 respectively) were injected subcutaneously into beige SCID mice. The tumor volume was measured at indicated time points.

Tumor volume in the mice was measured at day 0, 14, 18, and 26. As shown in FIG. 17, no measurable tumor developed in study groups 3, 4, and 5. Measurable tumor similar to that in the PBMC control was found in the study group receiving the lowest dose of CAR-expressing PBMCs (0.7e6).

Figure 18:
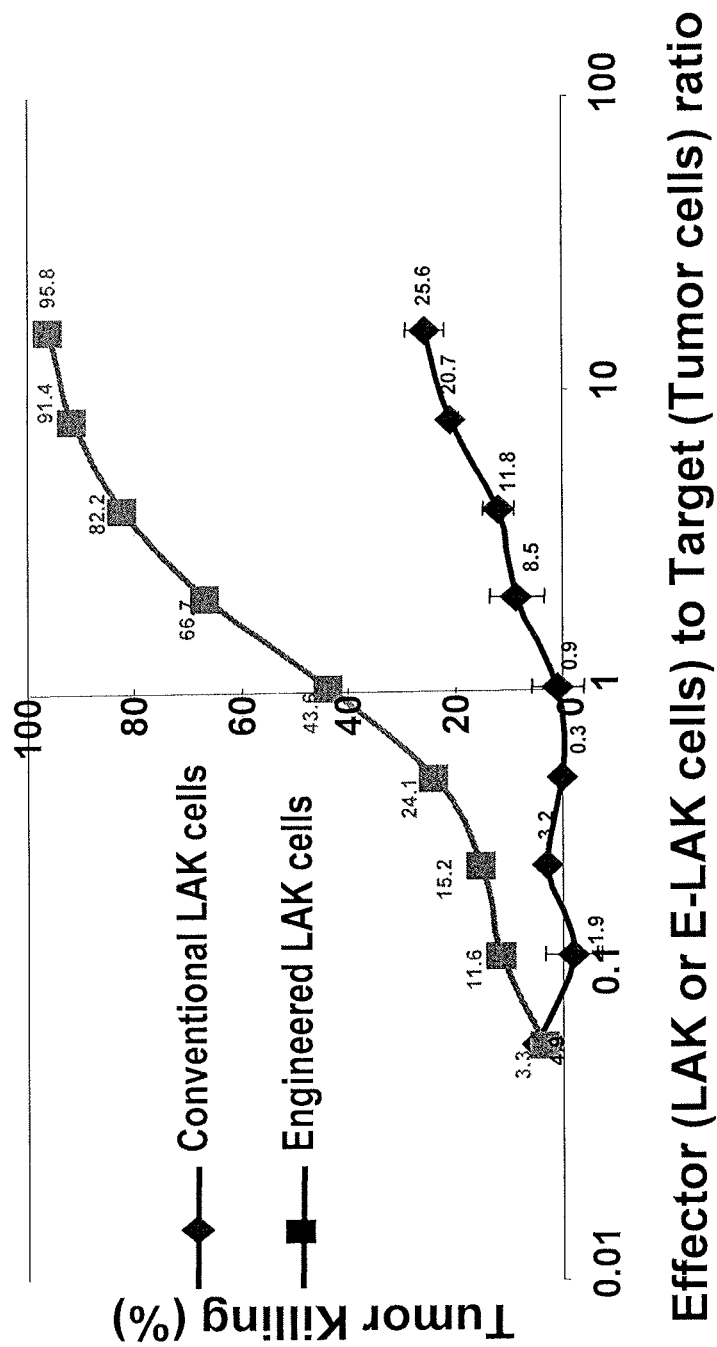
FIG. 18. Cytokine-induced NK cells (LAK) transfected with mRNA encoding anti-CD19-BBz exhibit greater cytotoxicity against HS-Sultan cells than stimulated LAK that were not transfected with mRNA encoding anti-CD19-BBz.

In a further in vitro study, cytokine-induced NK cells (LAK) were transfected with mRNA encoding anti-CD19-BBz and mixed with HS-Sultan cells for a cytotoxicity study. LAK cells are NK cells that have been stimulated to be cytotoxic to tumor cells by Interleukin-2. As shown in FIG. 18, while control LAK cells (conventional) were cytotoxic against HS-Sultan cells, the transfected LAK cells (Engineered LAK cells) were significantly more cytotoxic.

EXAMPLE 12

Effect of Intracellular Domains on CAR Expression

The effect of intracellular domains in the chimeric antigen receptor was evaluated with the following four anti-mesothelin CARs: ss1-28-BBz, ss1-28z, ss1-BBz, or ss1-z. RNA was prepared that encodes CAR composed of an anti-mesothelin (ss1) murine single-chain Fv binding domain with the combination of 3 intracellular activation domains derived from 41BB and CD28, and the cytoplasmic portion of the TcRz☐ chain.

Figure 19:
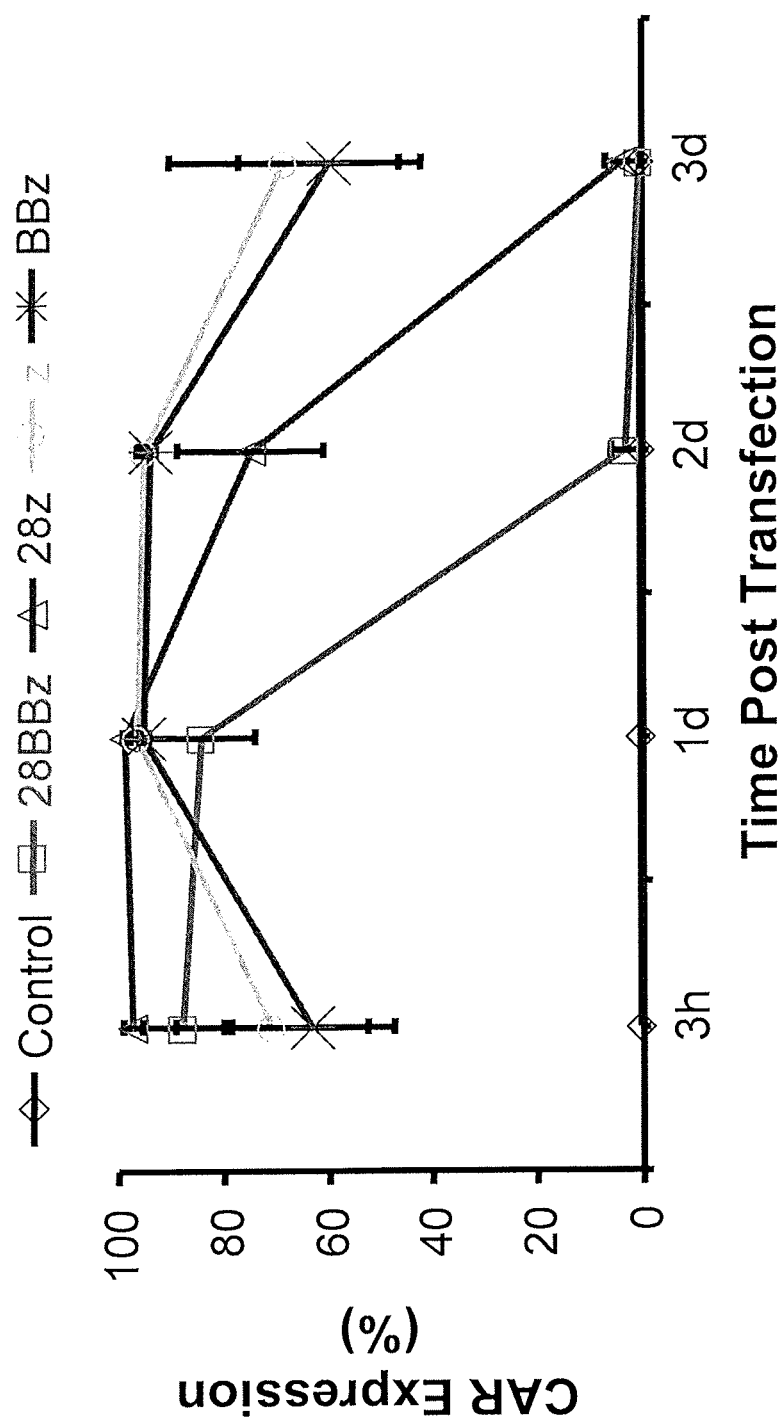
FIG. 19. The effect of intracellular domains on CAR expression in expanded T cells. The percent CAR expression is shown on the y axis. The time post transfection is shown on the x axis.
Figure 20:
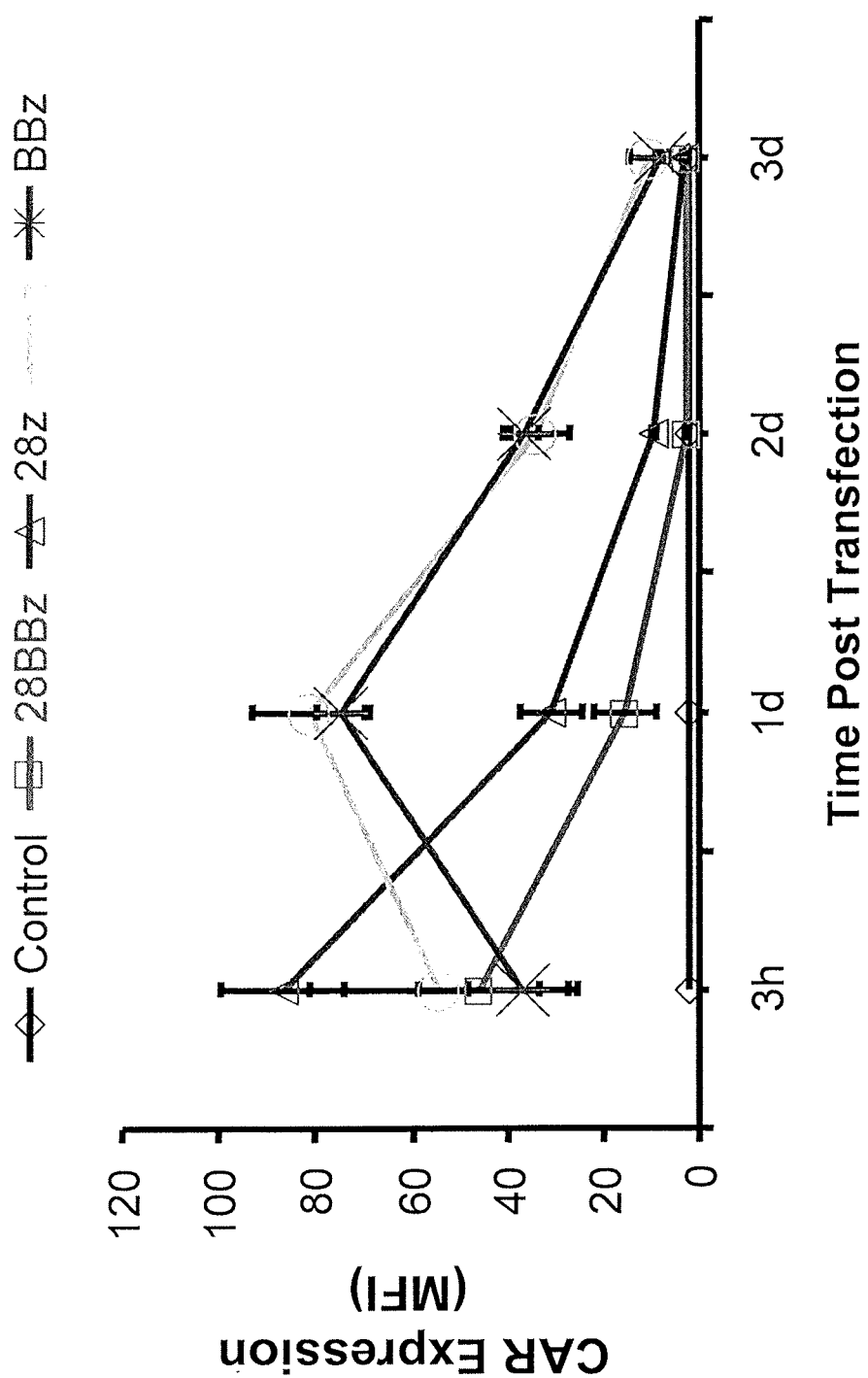
FIG. 20. The effect of intracellular domains on CAR expression in expanded T cells. The MFI is shown on the y axis. The time post transfection is shown on the x axis.
Figure 21:
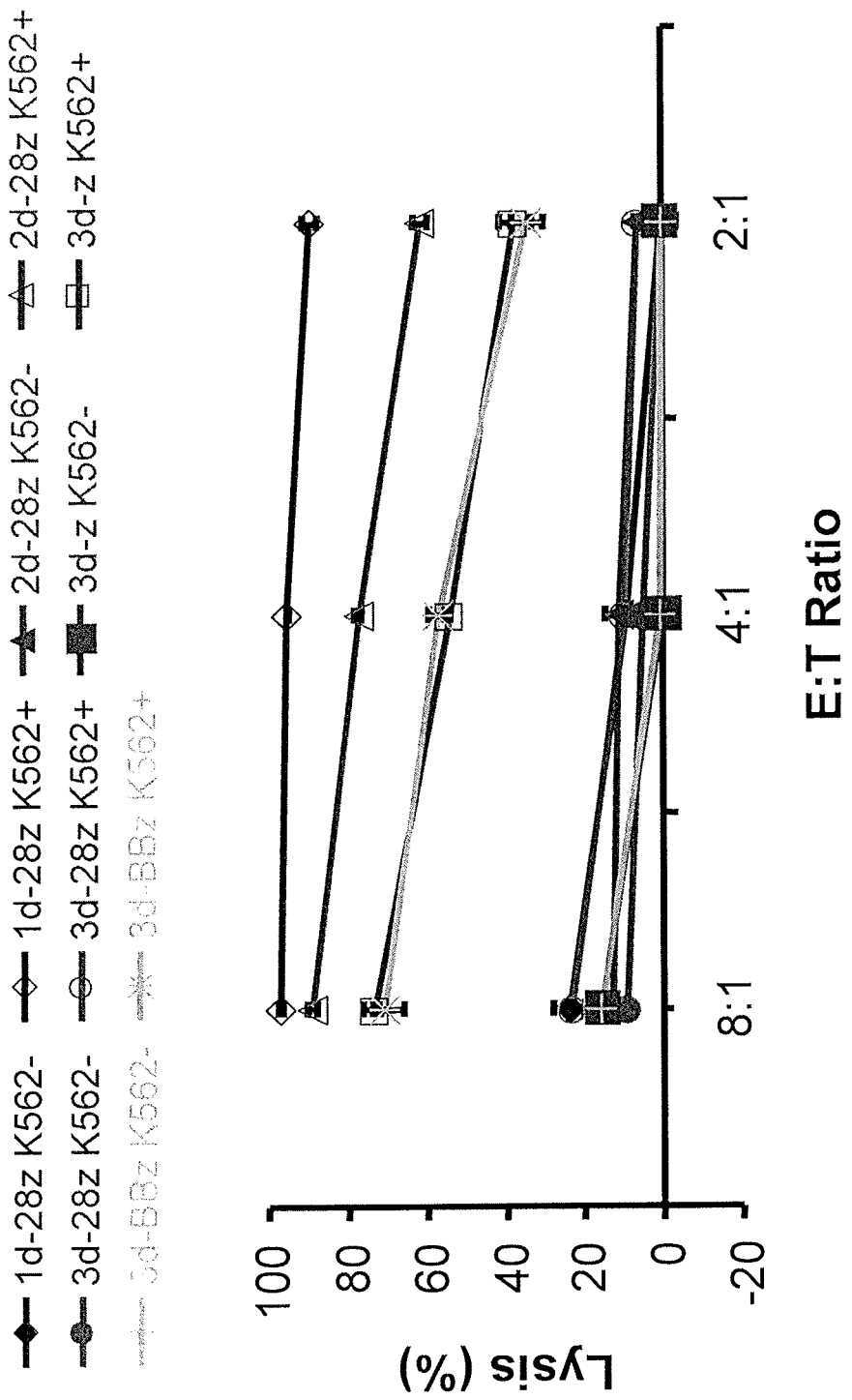
FIG. 21. K562 killing by expanded T cells transfected with CARs linked to different intracellular domains.

Expanded T cells were electroloaded with ss1-myc-28-BBz, ss1-28z, ss1-BBz, or ss1-z mRNAs. As shown in FIGS. 19 and 20, CAR expression decreased more quickly in the T cells transfected with mRNAs containing the CD28 intracellular domain (ss1-myc-28-BBz and ss1-28z). The decrease in CAR expression correlated with a decrease in the ability of the T cells to kill cancer cells. As shown in FIG. 21, only ss1-BBz and ss1-z (i.e., the mRNAs that did not have the CD28 intracellular domain) transfected T cells maintained K562 cell killing ability 3 days post transfection.

Figure 22:
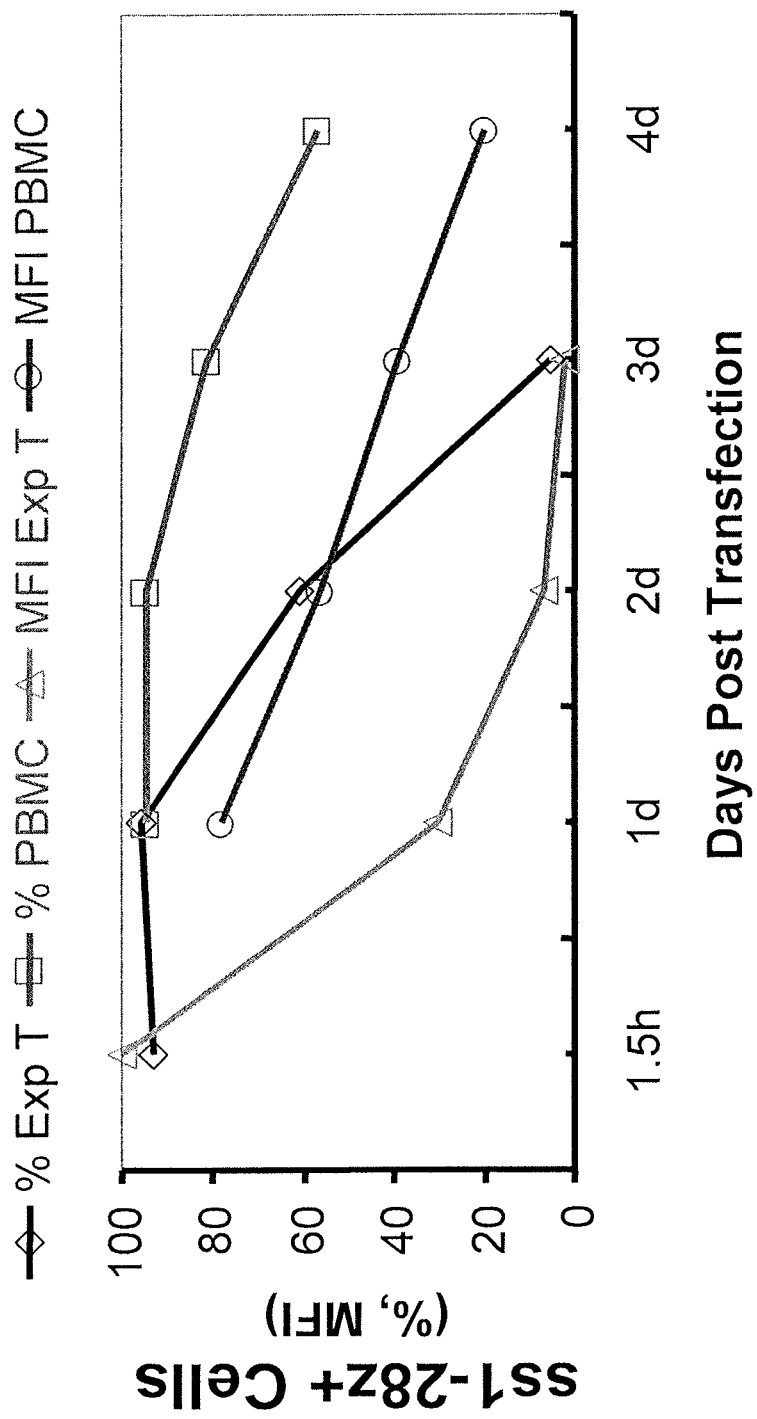
FIG. 22. The CD28 intracellular domain deceases expression of CARs faster in T cells than in unstimulated resting PBMCs.
Figure 23:
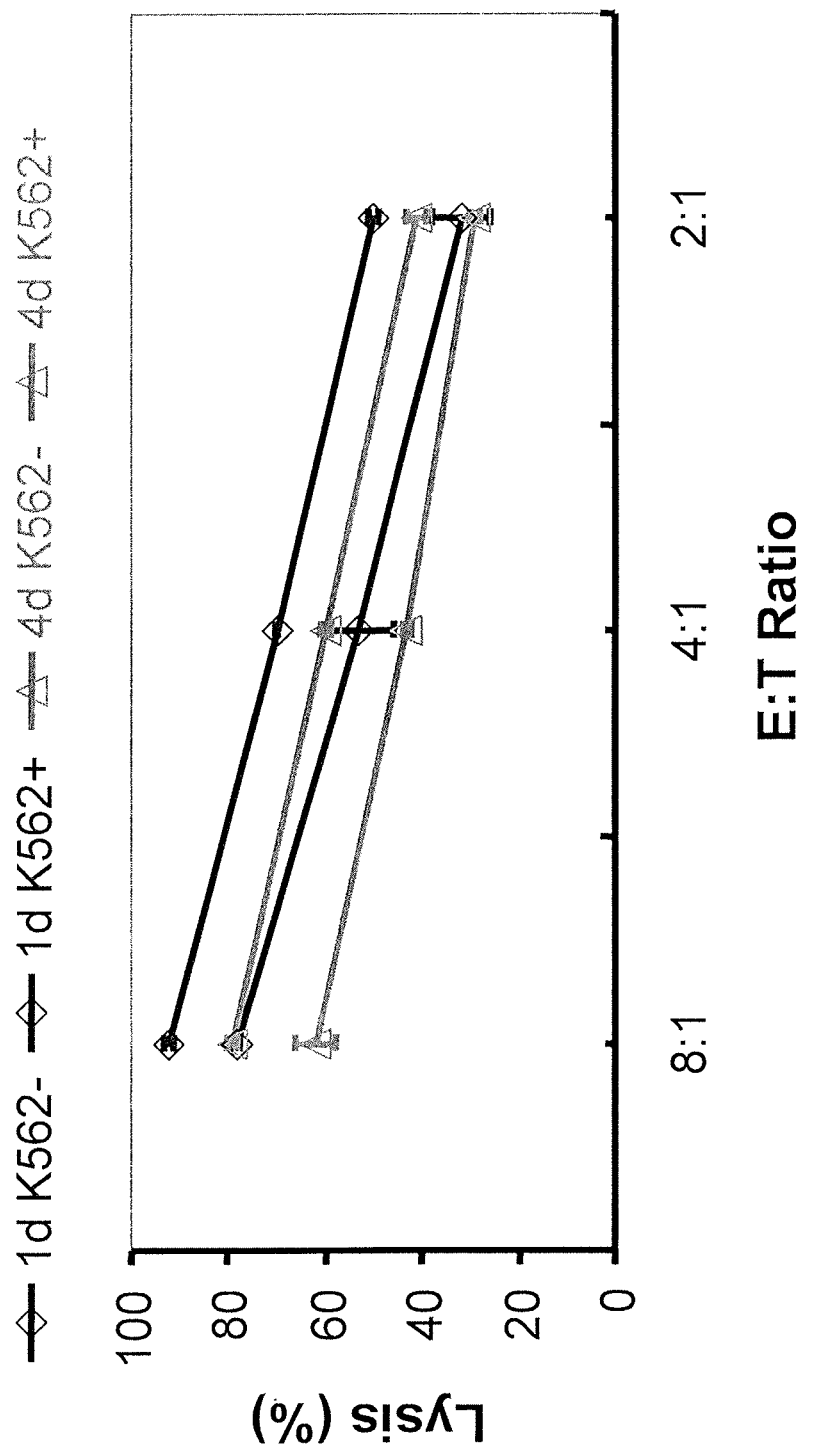
FIG. 23. Unstimulated resting PBMCs transfected with the ss1-28z CAR maintained K562+ cell killing at four days post transfection.

The expression of ss1-28z was compared in PBMCs and expanded T cells. As shown in FIG. 22, ss1-28z expression decreases faster in T cells than in PBMCs. This may be a result of the T cells doubling faster than the PBMCs. The ss1-28z transfected PBMCs maintained K562+ cell killing ability at 4 days post transfection (FIG. 23).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,683,202
U.S. Pat. No. 5,612,207
U.S. Pat. No. 5,720,921
U.S. Pat. No. 5,925,565
U.S. Pat. No. 5,928,906
U.S. Pat. No. 5,935,819
U.S. Pat. No. 6,074,605
U.S. Pat. No. 6,090,617
U.S. Pat. No. 6,090,617
U.S. Pat. No. 6,485,961
U.S. Pat. No. 6,617,154
U.S. Pat. No. 6,773,669
U.S. application Ser. No. 10/781,440
U.S. application Ser. No. 10/675,592
U.S. application Ser. No. 10/399,364
U.S. application Ser. No. 10/225,446
U.S. application Ser. No. 10/225,446
U.S. application Ser. No. 10/080,272
Almendro et al., *J. Immunol.*, 157(12):5411-5421, 1996.
Angel et al., *Mol. Cell. Biol.*, 7:2256, 1987a.
Angel et al., *Cell*, 49:729, 1987b.
Atchison and Perry, *Cell*, 46:253, 1986.
Atchison and Perry, *Cell*, 48:121, 1987.
Ausubel et al., In: *Current Protocols in Molecular Biology*, John, Wiley & Sons, Inc, New York, 1996.
Banerji et al., *Cell*, 27(2 Pt 1):299-308, 1981.
Banerji et al., *Cell*, 33(3):729-740, 1983.
Berkhout et al., *Cell*, 59:273-282, 1989.
Biagi et al., *Hum. Gen Ther.*, 14(6):545-559, 2003.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5(7):1615-1623, 1986.
Braddock et al., *Cell*, 58:269, 1989.
Bulla and Siddiqui, *J. Virol.*, 62:1437, 1986.
Califano et al., *Cancer Res.*, 56(11):2488-2492, 1996.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Carbonelli et al., *FEMS Microbiol. Lett.*, 177(1):75-82, 1999.
Celander and Haseltine, *J. Virology*, 61:269, 1987.
Celander et al., *J. Virology*, 62:1314, 1988.
Chandler et al., *Cell*, 33:489, 1983.
Chandler et al., *Proc. Natl. Acad. Sci. USA*, 94(8):3596-601, 1997.
Chang et al., *Mol. Cell. Biol.*, 9:2153, 1989.
Chatterjee et al., *Proc. Natl. Acad. Sci. USA*, 86:9114, 1989.
Chen et al., *Oncogene*, 8:2159-66, 1993.
Choi et al., *Cell*, 53:519, 1988.
Cocea, *Biotechniques*, 23(5):814-816, 1997.
Cohen et al., *J. Cell. Physiol.*, 5:75, 1987.
Connor et al., *Int. J. Gynecol. Cancer*, 3(2):103-109, 1993.
Connor et al., *J. Exp. Med.*, 177:1127-1134, 1993.
Costa et al., *Mol. Cell. Biol.*, 8:81, 1988.
Cripe et al., *EMBO J.*, 6:3745, 1987.
Culotta and Hamer, *Mol. Cell. Biol.*, 9:1376, 1989.
Dandolo et al., *J. Virology*, 47:55-64, 1983.
De Jager et al., *Semin. Nucl. Med.*, 23(2):165-179, 1993.
De Villiers et al., *Nature*, 312(5991):242-246, 1984.
Deschamps et al., *Science*, 230:1174-1177, 1985.
Dilloo et al., *Blood*, 90(5):1927-1933, 1997.
Doolittle and Ben-Zeev, *Methods Mol Biol*, 109:215-237, 1999.
Dranoff et al., *Proc. Natl. Acad. Sci. USA*, 90:3539-3543, 1993.
Edbrooke et al., *Mol. Cell. Biol.*, 9:1908, 1989.
Edlund et al., *Science*, 230:912-916, 1985.
Fearon and Vogelstein, *Cell*, 61(5):759-767, 1990.
Feng and Holland, *Nature*, 334:6178, 1988.
Firak and Subramanian, *Mol. Cell. Biol.*, 6:3667, 1986.
Foecking and Hofstetter, *Gene*, 45(1):101-105, 1986.
Fujita et al., *Cell*, 49:357, 1987.
Gabriel and Teissie, *Biophys. J.*, 76(4):2158-2165, 1999.
Gansbacher et al., *Cancer Res.*,50(24):7820-7825, 1990.
Gansbacher et al., *J. Exp. Med.*, 172:1217-1224, 1990.
Gilles et al., *Cell*, 33:717, 1983.
Gloss et al., *EMBO J.*, 6:3735, 1987.
Godbout et al., *Mol. Cell. Biol.*, 8:1169, 1988.
Goodbourn and Maniatis, *Proc. Natl. Acad. Sci. USA*, 85:1447, 1988.
Goodbourn et al., *Cell*, 45:601, 1986.
Greene et al., *Immunology Today*, 10:272, 1989
Grosschedl and Baltimore, *Cell*, 41:885, 1985.
Gulbis and Galand, *Hum. Pathol.*, 24(12):1271-1285, 1993.
Harding, *Eur. J. Immunol.*, 22(7):1865-1869, 1992.
Haslinger and Karin, *Proc. Natl. Acad. Sci. USA*, 82:8572, 1985.
Hauber and Cullen, *J. Virology*, 62:673, 1988.
Hen et al., *Nature*, 321:249, 1986.
Hensel et al., *Lymphokine Res.*, 8:347, 1989.
Herr and Clarke, *Cell*, 45:461, 1986.
Hibino et al., *Biophys. J.*, 64(6):1789-1800, 1993.
Hirochika et al., *J. Virol.*, 61:2599, 1987.
Hirsch et al., *Mol. Cell. Biol.*, 10:1959, 1990.
Holbrook et al., *Virology*, 157:211, 1987.
Horlick and Benfield, *Mol. Cell. Biol.*, 9:2396, 1989.
Huang et al., *Cell*, 27:245, 1981.
Hug et al., *Mol. Cell. Biol.*, 8:3065, 1988.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jain et al., *Ann. Surg. Oncology*, 10:810-820, 2003.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Kadesch and Berg, *Mol. Cell. Biol.*, 6:2593, 1986.
Kakorin et al., *Biophys. Chem.*, 58(1-2):109-116, 1996.
Karin et al., *Mol. Cell. Biol.*, 7:606, 1987.
Karp et al., *J. Immunol.*, 150(3):896-908, 1993.
Kasaian et al., *Immunity*, 16:559-569, 2002.

Katinka et al., *Cell*, 20:393, 1980.
Kawamoto et al., *Mol. Cell. Biol.*, 8:267, 1988.
Kiledjian et al., *Mol. Cell. Biol.*, 8:145, 1988.
Kim et al., *J. Virol.*, 76(4)1892-1903, 2002.
Kimura et al., *Arch. Otolaryngol Head Neck Surg.*, 129: 1181-1185, 2003.
Kishida et al., *Gene Therapy*, 8:1234-1240, 2001.
Kishida et al., *Mol. Ther.*, 8(4):552-558, 2003.
Klamut et al., *Mol. Cell. Biol.*, 10:193, 1990.
Knutson and Yee, *Anal. Biochem.*, 164(1):44-52, 1987.
Koch et al., *Mol. Cell. Biol.*, 9:303, 1989.
Kotnik et al., *Bioenerg.*, 43:281-291; 45:3-16, 1998.
Kraus et al. *FEBS Lett.*, 428(3):165-170, 1998.
Kriegler and Botchan, In: *Eukaryotic Viral Vectors*, Gluzman (Ed.), Cold Spring Harbor: Cold Spring Harbor Laboratory, NY, 1982.
Kriegler and Botchan, *Mol. Cell. Biol.*, 3:325, 1983.
Kriegler et al., *Cell*, 38:483, 1984.
Kriegler et al., *Cell*, 53:45, 1988.
Kuhl et al., *Cell*, 50:1057, 1987.
Kunz et al., *Nucl. Acids Res.*, 17:1121, 1989.
Lareyre et al., *J. Biol. Chem.*, 274(12):8282-8290, 1999.
Larsen et al., *Proc Natl. Acad. Sci. USA*, 83:8283, 1986.
Laspia et al., *Cell*, 59:283, 1989.
Latimer et al., *Mol. Cell. Biol.*, 10:760, 1990.
Lee et al., *DNA Cell Biol.*, 16(11):1267-1275, 1997.
Lee et al., *Nature*, 294:228, 1981.
Lee et al., *Nucleic Acids Res.*, 12:4191-206, 1984.
Levenson et al., *Hum. Gene Ther.*, 9(8):1233-1236, 1998.
Levinson et al., *Nature*, 295:79, 1982.
Li et al., In: *Am. Soc. Gene Therapy*, Abstract, 5$^{th}$ Annual Meeting, 2002.
Li et al., *J. Leukoc. Biol.*, 56(5):616-624, 1994.
Lin et al., *Mol. Cell. Biol.*, 10:850, 1990.
Luria et al., *EMBO J.*, 6:3307, 1987.
Lusky and Botchan, *Proc. Natl. Acad. Sci. USA*, 83:3609, 1986.
Lusky et al., *Mol. Cell. Biol.*, 3:1108, 1983.
Ma et al., *J. Immunol.*, 171(2):608-615, 2003.
Macejak and Sarnow, *Nature*, 353:90-94, 1991.
Majors and Varmus, *Proc. Natl. Acad. Sci. USA*, 80:5866, 1983.
McNeall et al., *Gene*, 76:81, 1989.
Mellman and Steinman, *Cell*, 106(3):255-258, 2001.
Miksicek et al., *Cell*, 46:203, 1986.
Mir, *Bioelectrochem.*, 53:1-10, 2000.
Mordacq and Linzer, *Genes and Dev.*, 3:760, 1989.
Moreau et al., *Nucl. Acids Res.*, 9:6047, 1981.
Muesing et al., *Cell*, 48:691, 1987.
Nakamura et al., In: *Handbook of Experimental Immunology* (4$^{th}$ Ed.), Weir et al. (Eds.), 1:27, Blackwell Scientific Publ., Oxford, 1987.
Neumann et al., *Proc. Natl. Acad. Sci. USA*, 96(16):9345-9350, 1999.
Ng et al., *Nuc. Acids Res.*, 17:601, 1989.
Nomoto et al., *Gene*, 236(2):259-271, 1999.
Ondek et al., *EMBO J.*, 6:1017, 1987.
Ornitz et al., *Mol. Cell. Biol.*, 7:3466, 1987.
Palmiter et al., *Nature*, 300:611, 1982.
PCT Appln. WO 03/018751
PCT Appln. WO 03/018751
PCT Appln. WO 04/031353
Pech et al., *Mol. Cell. Biol.*, 9:396, 1989.
Pelletier and Sonenberg, *Nature*, 334(6180):320-325, 1988.
Perez-Stable and Constantini, *Mol. Cell. Biol.*, 10:1116, 1990.
Picard and Schaffner, *Nature*, 307:83, 1984.
Pinkert et al., *Genes and Dev.*, 1:268, 1987.
Ponta et al., *Proc. Natl. Acad. Sci. USA*, 82:1020, 1985.
Porton et al., *Mol. Cell. Biol.*, 10:1076, 1990.
Queen and Baltimore, *Cell*, 35:741, 1983.
Quinn et al., *Mol. Cell. Biol.*, 9:4713, 1989.
Redondo et al., *Science*, 247:1225, 1990.
Reisman and Rotter, *Mol. Cell. Biol.*, 9:3571, 1989.
Resendez Jr. et al., *Mol. Cell. Biol.*, 8:4579, 1988.
Ripe et al., *Mol. Cell. Biol.*, 9:2224, 1989.
Rittling et al., *Nuc. Acids Res.*, 17:1619, 1989.
Rols and Teissie, *Biophys. J.*, 75(3):1415-1423, 1998.
Rosen et al., *Cell*, 41:813, 1988.
Sakai et al., *Genes and Dev.*, 2:1144, 1988.
Sambrook et al., In: *Molecular cloning*, Cold Spring Harbor Laboratory Press, Cold Spring Harbor, N.Y., 2001.
Satake et al., *J. Virology*, 62:970, 1988.
Schaffner et al., *J. Mol. Biol.*, 201:81, 1988.
Searle et al., *Mol. Cell. Biol.*, 5:1480, 1985.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Sleigh and Lockett, *J. EMBO*, 4:3831, 1985.
Spalholz et al., *Cell*, 42:183, 1985.
Spandau and Lee, *J. Virology*, 62:427, 1988.
Spandidos and Wilkie, *EMBO J.*, 2:1193, 1983.
Stephens and Hentschel, *Biochem. J.*, 248:1, 1987.
Strengall et al., *J. Immunology*, 170:5464-5469, 2003.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Takebe et al., *Mol. Cell. Biol.*, 8:466, 1988.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Thiesen et al., *J. Virology*, 62:614, 1988.
Treisman, *Cell*, 42:889, 1985.
Tronche et al., *Mol. Biol. Med.*, 7:173, 1990.
Trudel and Constantini, *Genes and Dev.* 6:954, 1987.
Tsumaki et al., *J. Biol. Chem.*, 273(36):22861-22864, 1998.
Tyndell et al., *Nuc. Acids. Res.*, 9:6231, 1981.
Van Meirvenne et al., *Cancer Gene Ther.*, 9(9):787-797, 2002.
van Schooten et al., *Mol Med Today*, 3(6):254-260, 1997.
Van Tendeloo et al., *Blood*, 98(1):49-56, 2001.
Vannice and Levinson, *J. Virology*, 62:1305, 1988.
Vasseur et al., *Proc Natl. Acad. Sci. U.S.A.*, 77:1068, 1980.
Wang and Calame, *Cell*, 47:241, 1986.
Weaver and Chizmadzhev, *Bioenerg.*, 41:135-160, 1996.
Weber et al., *Cell*, 36:983, 1984.
Weinberger et al. *Mol. Cell. Biol.*, 8:988, 1984.
Weiss et al. *Proc. Am. Assoc. Cancer Res.*, 44(5493):1094-1095, 2003.
Weiss et al. *Proc. Am. Assoc. Cancer Res.*, 44:1094-1095, 2003.
Wendtner, *Leuk. Lymphoma*, 45(5):897-904, 2004.
Wierda et al. *Blood*, 96(9):2917-2924, 2000.
Winoto and Baltimore, *Cell* 59:649, 1989.
Wu et al., *Biochem. Biophys. Res. Commun.*, 233(1):221-2266, 1997.
Yutzey et al. *Mol. Cell. Biol.*, 9:1397, 1989.
Zhao-Emonet et al., *Biochim. Biophys. Acta*, 1442(2-3):109-119, 1998.
Zhou et al., *J. Biol. Chem.*, 270(21)12665-12669, 1995.
Lanier L L. Activating and inhibitory NK cell receptors. Adv Exp Med Biol. 1998; 452:13-18.

Passweg J R, Tichelli A, Meyer-Monard S, et al. Purified donor NK-lymphocyte infusion to consolidate engraftment after haploidentical stem cell transplantation. Leukemia. 2004; 18:1835-1838.

McKenna D H, Jr., Sumstad D, Bostrom N, et al. Good manufacturing practices production of natural killer cells for immunotherapy: a six-year single-institution experience. Transfusion. 2007; 47:520-528.

Chiorean E G, Miller J S. The biology of natural killer cells and implications for therapy of human disease. J Hematother Stem Cell Res. 2001; 10:451-463.

Farag S S, Fehniger T A, Ruggeri L, Velardi A, Caligiuri M A. Natural killer cell receptors: new biology and insights into the graft-versus-leukemia effect. Blood. 2002; 100: 1935-1947.

Klingemann H G. Natural killer cell-based immunotherapeutic strategies. Cytotherapy. 2005; 7:16-22.

Miller J S, Soignier Y, Panoskaltsis-Mortari A, et al. Successful adoptive transfer and in vivo expansion of human haploidentical NK cells in patients with cancer. Blood. 2005; 105:3051-3057.

Ruggeri L, Mancusi A, Burchielli E, Aversa F, Martelli M F, Velardi A. Natural killer cell alloreactivity in allogeneic hematopoietic transplantation. Curr Opin Oncol. 2007; 19:142-147.

Imai C, Mihara K, Andreansky M, et al. Chimeric receptors with 4-1BB signaling capacity provoke potent cytotoxicity against acute lymphoblastic leukemia. Leukemia. 2004; 18:676-684.

Golzio M, Rols M P, Teissie J. In vitro and in vivo electric field-mediated permeabilization, gene transfer, and expression. Methods. 2004; 33:126-135.

Hui S, Li L. Electrically mediated delivery of molecules to cells: Human Press; 2000.

Xie T D, Sun L, Tsong T Y. Study of mechanisms of electric field-induced DNA transfection. I. DNA entry by surface binding and diffusion through membrane pores. Biophys J. 1990; 58:13-19.

Zimmermann U. Electrical breakdown, electropermeabilization and electrofusion. Rev Physiol Biochem Pharmacol. 1986; 105:176-256.

Li L H, Shivakumar R, Feller S, et al. Highly efficient, large volume flow electroporation. Technol Cancer Res Treat. 2002; 1:341-350.

Trompeter H I, Weinhold S, Thiel C, Wernet P, Uhrberg M. Rapid and highly efficient gene transfer into natural killer cells by nucleofection. J Immunol Methods. 2003; 274:245-256.

Li L H, Biagi E, Allen C, et al. Rapid and efficient nonviral gene delivery of CD154 to primary chronic lymphocytic leukemia cells. Cancer Gene Ther. 2006; 13:215-224.

Li L H, McCarthy P, Hui S W. High-efficiency electrotransfection of human primary hematopoietic stem cells. Faseb J. 2001; 15:586-588.

Li L H, Sen A, Murphy S P, Jahreis G P, Fuji H, Hui S W. Apoptosis induced by DNA uptake limits transfection efficiency. Exp Cell Res. 1999; 253:541-550.

Landi A, Babiuk L A, van Drunen Littel-van den Hurk S. High transfection efficiency, gene expression, and viability of monocyte-derived human dendritic cells after nonviral gene transfer. J Leukoc Biol. 2007.

Van De Parre T J, Martinet W, Schrijvers D M, Herman A G, De Meyer G R. mRNA but not plasmid DNA is efficiently transfected in murine J774A.1 macrophages. Biochem Biophys Res Commun. 2005; 327:356-360.

Rabinovich P M, Komarovskaya M E, Ye Z J, et al. Synthetic messenger RNA as a tool for gene therapy. Hum Gene Ther. 2006; 17:1027-1035.

Zhao Y, Zheng Z, Cohen C J, et al. High-efficiency transfection of primary human and mouse T lymphocytes using RNA electroporation. Mol Ther. 2006; 13:151-159.

Manabe A, Coustan-Smith E, Kumagai M, et al. Interleukin-4 induces programmed cell death (apoptosis) in cases of high-risk acute lymphoblastic leukemia. Blood. 1994; 83:1731-1737.

Ruggeri L, Capanni M, Urbani E, et al. Effectiveness of donor natural killer cell alloreactivity in mismatched hematopoietic transplants. Science. 2002; 295:2097-2100.

Leung W, Iyengar R, Turner V, et al. Determinants of antileukemia effects of allogeneic NK cells. J Immunol. 2004; 172:644-650.

Caligiuri M A, Velardi A, Scheinberg D A, Borrello I M. Immunotherapeutic approaches for hematologic malignancies. Hematology Am Soc Hematol Educ Program. 2004: 337-353.

Maasho K, Marusina A, Reynolds N M, Coligan J E, Borrego F. Efficient gene transfer into the human natural killer cell line, NKL, using the Amaxa nucleofection system. J Immunol Methods. 2004; 284:133-140.

Abbott B L. Recent advances in chronic lymphocytic leukemia. Cancer Invest. 2006; 24:302-309.

The invention claimed is:

1. A composition comprising a population of at least 80% viable electroloaded modified unstimulated T cells transiently transfected with mRNA to express a chimeric receptor on its surface, wherein said modified T cells are produced by the method comprising:
   (a) obtaining unstimulated mononuclear cells;
   (b) electroloading the mononuclear cells with a mRNA encoding a chimeric receptor comprising a nucleic acid sequence encoding an extracellular domain, a transmembrane domain, a costimulatory signaling region, and a CD3-zeta signaling domain;
   (c) transiently expressing the chimeric receptor encoded by said nucleic acid sequence; and
   wherein the viability of said composition of said electroloaded modified T cells 1 day after electroloading is at least 80% if normalized to un-electroloaded mononuclear cells.

2. The composition of claim 1, wherein the extracellular domain comprises an antigen-binding moiety.

3. The composition of claim 2, wherein the antigen-binding moiety binds to a tumor antigen.

4. The composition of claim 3, wherein the tumor antigen is an antigen associated with a cancer selected from the group consisting of breast cancer, lung cancer, prostate cancer, ovarian cancer, brain cancer, liver cancer, cervical cancer, colon cancer, renal cancer, skin cancer, head & neck cancer, bone cancer, esophageal cancer, bladder cancer, uterine cancer, lymphatic cancer, stomach cancer, pancreatic cancer, testicular cancer, leukemia, acute lymphocytic leukemia (ALL), acute myelogenous leukemia (AML), chronic lymphocytic leukemia (CLL), chronic myelogenous leukemia (CML), and mantle cell lymphoma (MCL).

5. The composition of claim 1, wherein the chimeric receptor is an anti-mesothelin chimeric receptor.

6. The composition of claim 5, wherein the anti-mesothelin chimeric receptor comprises an anti-mesothelin scFv.

7. The composition of claim 6, wherein the anti-mesothelin scFv is ss1.

8. The composition of claim 1, wherein the chimeric receptor comprises an intracellular domain selected from either 41 BB or CD28, and the cytoplasmic portion of the CD3-zeta chain.

9. The composition of claim 5, wherein the anti-mesothelin chimeric receptor comprises an anti-mesothelin scFv, a 4-1 BB intracellular domain, and a CD3-zeta domain.

10. A method comprising administering to a subject the composition of claim 1.

11. The method of claim 10, wherein the subject has a hyperproliferative disease.

12. The method of claim 10, wherein the extracellular domain comprises an antigen binding moiety.

13. The method of claim 12, wherein the antigen binding moiety binds to a tumor antigen.

14. The method of claim 11, wherein the hyperproliferative disease is cancer.

15. The method of claim 14, wherein the cancer is selected from the group consisting of breast cancer, lung cancer, prostate cancer, ovarian cancer, brain cancer, liver cancer, cervical cancer, colon cancer, renal cancer, skin cancer, head & neck cancer, bone cancer, esophageal cancer, bladder cancer, uterine cancer, lymphatic cancer, stomach cancer, pancreatic cancer, testicular cancer, leukemia, acute lymphocytic leukemia (ALL), acute myelogenous leukemia (AML), chronic lymphocytic leukemia (CLL), chronic myelogenous leukemia (CML), and mantle cell lymphoma (MCL).

16. The method of claim 10, wherein the chimeric receptor is an anti-mesothelin chimeric receptor.

17. The method of claim 16, wherein the anti-mesothelin chimeric receptor comprises an anti-mesothelin scFv.

18. The method of claim 17, wherein the anti-mesothelin scFv is ss1.

19. The method of claim 10, wherein the chimeric receptor comprises an intracellular domain selected from either 4-1 BB or CD28, and the cytoplasmic portion of the CD3-zeta chain.

20. The method of claim 16, wherein the anti-mesothelin chimeric receptor comprises an anti-mesothelin scFv, a 4-1 BB intracellular domain, and a CD3-zeta domain.

21. A composition comprising a population of at least 80% viable electroloaded modified unstimulated T cells transiently transfected with mRNA to express a protein, wherein said modified T cells are produced by the method comprising:

(a) obtaining unstimulated mononuclear cells; and
(b) electroloading the mononuclear cells with a mRNA comprising a nucleic acid sequence encoding the protein,
(c) transiently expressing the protein encoded by said nucleic acid sequence;
wherein the viability of said composition of said electroloaded modified T cells 1 day after electroloading is at least 80% if normalized to un-electroloaded mononuclear cells.

22. A method comprising administering to a subject the composition of claim 21.

23. The method of claim 22, wherein the subject has a hyperproliferative disease.

24. The method of claim 23, wherein the hyperproliferative disease is cancer.

25. The method of claim 24, wherein the cancer is selected from the group consisting of breast cancer, lung cancer, prostate cancer, ovarian cancer, brain cancer, liver cancer, cervical cancer, colon cancer, renal cancer, skin cancer, head & neck cancer, bone cancer, esophageal cancer, bladder cancer, uterine cancer, lymphatic cancer, stomach cancer, pancreatic cancer, testicular cancer, leukemia, acute lymphocytic leukemia (ALL), acute myelogenous leukemia (AML), chronic lymphocytic leukemia (CLL), chronic myelogenous leukemia (CML), and mantle cell lymphoma (MCL).

26. The composition of claim 21, wherein protein is a chimeric receptor.

27. A method comprising administering to a subject the composition of claim 26.

28. The method of claim 27, wherein the subject has a hyperproliferative disease.

29. The method of claim 28, wherein the hyperproliferative disease is cancer.

30. The method of claim 29, wherein the cancer is selected from the group consisting of breast cancer, lung cancer, prostate cancer, ovarian cancer, brain cancer, liver cancer, cervical cancer, colon cancer, renal cancer, skin cancer, head & neck cancer, bone cancer, esophageal cancer, bladder cancer, uterine cancer, lymphatic cancer, stomach cancer, pancreatic cancer, testicular cancer, leukemia, acute lymphocytic leukemia (ALL), acute myelogenous leukemia (AML), chronic lymphocytic leukemia (CLL), chronic myelogenous leukemia (CML), and mantle cell lymphoma (MCL).

* * * * *